US005686250A

United States Patent [19]
Salomon

[11] Patent Number: 5,686,250
[45] Date of Patent: Nov. 11, 1997

[54] ANTIBODIES TO LGE$_2$-PROTEIN ANTIGENS

[75] Inventor: Robert G. Salomon, Mayfield Village, Ohio

[73] Assignee: Case Western Reserve University, Cleveland, Ohio

[21] Appl. No.: 509,180

[22] Filed: Jul. 31, 1996

[51] Int. Cl.$^6$ .......................... G01N 33/53; G01N 33/92; C07K 16/00
[52] U.S. Cl. .................. 435/7.1; 435/7.92; 530/387.1; 436/13; 436/71; 436/88
[58] Field of Search .................... 435/7.1, 7.92; 530/387.1; 436/13, 71, 88

[56] References Cited

FOREIGN PATENT DOCUMENTS

WO 89/04486  5/1989  WIPO.

OTHER PUBLICATIONS

Goldyne, Prostaglandins & Other Eicosanoids, Appelton & Lange, Los Altos, CA, 1987, 211–221.
Zubay, Biochemistry, 1983, Addison–Wesley, Reading, Mass p. 555.
Leninger et al, Principles of Biochemistry, 1993, Worth Pub, NY, pp. 258 & 656.
J.T. Shepherd, et al., "Report of the Task Force on Vascular Medicine," *Circulation* 89(1):532–35 (1994).
D. Driscoll et al. "Guidelines for Evaluation and Management of Common Congenital Cardiac Problems in Infants, Children, and Adolescents," *Circulation* 90(4):2180–88 (1994).
M.S. Remetz and R.A. Matthay, "Cardiac Evaluation," *Disease-a-Month* 38(6):338–503 (1992).
K.M. Coy et al., "Intravascular Ultrasound Imaging: A Current Perspective," *J. Am. Coll. Cardiol.* 18(7):1811–23 (1991).
S. Sirna et al., "Cardiac Evaluation of the Patient With Stroke," *Stroke* 21(1):14–23 (1990).
C.B. Higgins and G.R. Caputo, "Role of MR Imaging in Acquired and Congenital Cardiovascular Disease," *AJR* 161:13–22 (1993).
M. Tervahauta et al., "Prevalence Of Coronary Heart Disease and Associated Risk Factors Among Elderly Finnish Men in the Seven Countries Study," *Atherosclerosis* 104:47–59 (1993).
J.L. Breslow, "Genetics of Lipoprotein Disorders," *Circulation* 87:(supp. III):III–16—III–21 (1993).
E.J. Schaefer et al. "Familial lipoprotein disorders and premature coronary artery disease," *Atherosclerosis* 108(Supp):S41–S54 (1994).
B.A. Nassar, "Familial defective apolipoprotein B–100: a cause of hypercholesterolemia and early coronary heart disease," *Can. Med. Assoc. J.* 148(4):579–80 (1993).
A. Tybjaerg–Hansen et al., "Familial defective apolipoprotein B–100: detection in the United Kingdom and Scandinavia, and clinical characteristics of ten cases," *Atheroscelerosis* 80:235–42 (1990).

J. Woo et al., "Lipids, lipoproteins and other coronary risk factors in Chinese male survivors of myocardial infarction," *Intl. J. Card.* 39:195–202 (1993).
W.B. Kannel and P.W.F. Wilson, "Efficacy of lipid profiles in prediction of coronary disease," *Am. Heart J.* 124(3):768–74 (1992).
M.E. Goldyne, "Prostaglandins & Other Eicosanoids," in *Basic And Clinical Pharmacology*, Ch. 17, pp. 211–221; B.G. Katzung, ed., (Appleton & Lange, Los Altos, CA) (3rd Ed., 1987).
D. Steinberg et al., "Beyond Choleterol: Modifications of Low–Density Lipoprotein That Increase Its Atherogenicity," *N. Eng. J. Med.* 320:915–24 (1989).
S. Parthasarathy et al., "The Role of Oxidized Low–Density Lipoproteins in Pathogenesis of Atherosclerosis," *Annu. Rev. Med.* 43:219–25 (1992).
H. Easterbauer et al., "Autoxidation of human low density lipoprotein: loss of polyunsaturated fatty acids and vitamin E and generation of aldehydes," *J. Lipid Res.* 28:495 (1987).
A.M. Fogelman et al., "Malondialdehyde alteration of low density lipoproteins leads to cholesteryl ester accumulation in human monocyte–macrophages," *Proc. Natl. Acad. Sci. USA* 77:2214–18 (1980).
G.J. Jürgens et al., "Modification of human low–density lipoprotein by the lipid peroxidation product 4–hydroxynonenal," *Biochim. Biophys. Acta* 875:103–14 (1986).
F. Hayase et al., "Aging of Proteins: Immunological Detection Of A Glucose–Derived Pyrrole Formed During Maillard Reaction In Vivo," *J. Biol. Chem.* 263:3758–64 (1989).
S. Miyata and V. Monnier, "Immunohistochemical Detection Of Advanced Glycosylation End Products In Diabetic Tissues Using Monoclonal Antibody To Pyrraline," *J. Clin. Invest.* 89:1102–12 (1992).
S. Kim, "Part 1. Halichondrin B: Synthesis Of An H–Ring Intermediate; Part 2. Levuglandin–Protein Adducts: Synthesis Of An Antigen For Immunoassay", Thesis, Case Western Reserve University (1992).
K.K. Murthi, "Chapter 2. Levuglandins: Detection And Biological Chemistry," Thesis, Case Western Reserve University (1992).
E. DiFranco, "Part II. An Immunoassay For Protein–Bound Levuglandin–Derived Pyrroles," Thesis, Case Western Reserve University (1994).
R.A. Fishman and P.H, Chan, "Hypothesis: Membrane Phospholipid Degradation and Polyunsaturated Fatty Acids Play a Key Role in the Pathogenesis of Brain Edema", *Trans. Am. Neuro. Assoc.* 106:1 (1981).

(List continued on next page.)

Primary Examiner—Lila Feisee
Assistant Examiner—Susan Ungar
Attorney, Agent, or Firm—Medlen & Carroll, LLP

[57] ABSTRACT

Levuglandin (LG) derivatives are used as antigens for raising antibodies useful in diagnostic assays. The antibodies produced by LG-carrier protein adducts can be used to detect adducts of LGE$_2$ with human low density lipoprotein (LDL). LGE$_2$-protein adduct immunoreactivity may be generated during in vitro free-radical oxidation of LDL. An enzyme-linked immunosorbent assay for detecting adducts of LGE$_2$ with human LDL is also described.

20 Claims, 16 Drawing Sheets

OTHER PUBLICATIONS

M. Hamberg and B. Samuelsson, "Detection and Isolation of an Endoperoxide Intermediate in Protaglandin Biosynthesis," *Proc. Natl. Acad. Sci. USA* 70:899–903 (1973).

M. Hamberg et al., "Isolation and Structure of Two Prostaglandin Endoperoxides That Cause Platelet Aggregation," *Proc. Natl. Acad. Sci. USA* 71:345–49 (1974).

A. Raz et al., "Effect of Organic Sulfur Compounds on the Chemical Enzymatic Transformation of Prostaglandin Endoperoxide $H_2$," *Biochim. Biophys. Acta* 488:322–29 (1977).

D.H. Nugteren and E. Christ–Hazelhof, "Chemical and Enzymic Conversions of the Prostaglandin Endoperoxide $PGH_2$," *Adv. Prostaglandin Thromboxane Res.* 6:129–37 (1980).

R.G. Salomon et al., "Solvent–Induced Fragmentation of Prostaglandin Endoperoxides. New Aldehyde Products from $PGH_2$ and a Novel Intramolecular 1,2–Hydride Shift during Endoperoxide Fragmentation in Aqueous Solution," *J. Am. Chem. Soc.* 106:6049–60 (1984).

R.G. Salomon et al., "Prostaglandins Endoperoxides 21. Covalent Binding Of Levuglandin $E_2$ With Proteins," *Prostaglandins* 34:643–56 (1987).

R. Iyer et al., "Generation Of Pyrroles In The Reaction Of Levuglandin $E_2$ With Proteins," *J. Org. Chem.* 59:6038–6043 (1994).

S.M. Lynch et al., "Formation of Non–cyclooxygenase–derived Prostanoids ($F_2$–Isoprostanes) in Plasma and Low Density Lipoprotein Exposed to Oxidative Stress in Vitro," *J. Clin. Invest.* 93:998–1004 (1994).

J.D. Morrow et al., "Noncyclooxygenase Oxidative Formation of a Series of Novel Prostaglandins: Analytical Ramifications for Measurement of Eicosanoids," *Anal. Biochem.* 184:1–10 (1990).

U.P. Steinbrecher et al., "Modification of low density lipoprotein by endothelial cells involves lipid peroxidation and degradation of low density lipoprotein phospholipids," *Proc. Natl. Acad. Sci. USA* 81:3883–87 (1984).

U.P. Steinbrecher et al., "Decrease in Reactive Amino Groups during Oxidation or Endothelial Cell Modification of LDL," *Atherosclerosis* 7:135–43 (1987).

U.P. Steinbrecher, "Oxidation of Human Low Density Lipoprotein Results in Derivatization of Lysine Residues of Apolipoprotein B by Lipid Peroxide Decomposition Products," *J. Biol. Chem.* 262:3603–08 (1987).

U.P. Steinbrecher and P.H. Pritchard, "Hydrolysis of phosphatidylcholine during LDL oxidation is mediated by platelet–activating factor acetylhydrolase," *J. Lipid Res.* 30:305–15 (1989).

S. Parthasarathy and J. Barnett, "Phospholipase $A_2$ activity of low density lipoprotein: Evidence for an intrinsic phospholipase $A_2$ activity of apoprotein B–100," *Proc. Natl. Acad. Sci. USA* 87:9741–45 (1990).

N. Reisfeld et al., "Aplipoprotein B exhibits phospholipase $A_1$ and phospholipase $A_2$ activities," *FEBS Lett.* 315:267–70 (1993).

J.D. Morrow et al., "A series of prostaglandin $F_2$–like compounds are produced in vivo in humans by a non–cyclooxygenase, free radical–catalyzed mechanism," *Proc. Natl. Acad. Sci. USA* 87:9383–87 (1990).

M.F. White, et al., "The Insulin Signaling System," *J. Biol. Chem.* 269:1–4 (1994).

R.G. Salomon, *Accounts Chem. Res.* 18:294 (1985).

E. DiFranco et al., *Chem. Res. Toxicol.* 8:61–67 (1995).

A. Voller and D. Bidwell, in *Manual of Clinical Laboratory Immunology* (N.R. Rose et al., eds.; American Society For Microbiology, Washington D.C.) pp. 99–109 (3rd Ed. 1986).

D.B. Miller et al., "Levuglandin $E_2$: Enantiocontrolled Total Synthesis of a Biologically Active Rearrangement Product from the Prostaglandin Endoperoxide $PGH_2$," *J. Org. Chem.* 55:3164–75 (1990).

Baker, "Carbohydrate Thioacetals. I. Lead Tetraacetate Oxidation of D–Arabinose Derivatives," *J. Am. Chem. Soc.* 74:827 (1952).

M.E. Kobierski et al., "Synthesis of a Pyrazole Isostere of Pyrroles Formed by the Reaction of the ε–Amino Groups of Protein Lysyl Residues with Levuglandin $E_2$," *J. Org. Chem.* 59:6044–50 (1994).

W. Palinski et al., "Antisera and Monoclonal Antibodies Specific for Epitopes Generated during Oxidative Modification of Low Density Lipoprotein," *Arteriosclerosis* 10:325–335 (1990).

F.T. Hatch and R.S. Lees, "Practical Methods for Plasma Lipoprotein Analysis," *Adv. Lipid Res.* 6:2–63 (1968).

N. Hébert et al., "A New Reagent for the Removal of the 4–Methoxybenzyl Ether: Application to the Synthesis of Unusual Macrocyclic and Bolaform Phosphatidylcholines," *J. Org. Chem.* 57:1777–83 (1992).

M.A. Wells and D.J. Hanahan in *Meth. Enzymol.* (J.M. Lowenstein, ed.) 14:178–84 (1969).

P.K. Smith et al., "Measurement of Protein Using Bicinchoninic Acid," *Anal. Biochem.* 150:76–85 (1985).

D. Steinbrecher et al., "Decrease in Rective Amino Groups during Oxidation or Endothelial Cell Modification of LDL," *Arteriosclerosis* 7:135 (1987).

P. Avogaro et al., "Presence of a Modified Low Density Lipoprotein in Humans," *Arteriosclerosis* 8:79 (1988).

W. Palinski et al., "Low Density Lipoprotein Undergoes Oxidative Modification in vivo," *Proc. Natl. Acad. Sci. USA* 86:1372–76 (1989).

J.T. Salonen et al., "Autoantibody against oxidised LDL and progression of carotid atherosclerosis," *Lancet* 339:883–87 (1992).

K.K. Murthi et al., "Formation of DNA–Protein Cross–Links in Mammalian Cells by Levuglandin $E_2$," *Biochemistry* 32:4090–97 (1993).

R.S. Iyer et al., "Levuglandin $E_2$ Crosslinks Proteins," *Prostaglandins* 37:471–480 (1989).

F.A. Fitzpatrick and G.L. Bundy, "Hapten Mimic Elicits Antibodies Recognizing Prostaglandin $E_2$," (1978), Proc. Natl. Acad. Sci. 75:2689–2693 (1978).

H. Wehr et al., "Acetaldehyde Adducts And Autoantibidoes Against VLDL And LDL In Alcoholics," *J. Lipid Res.* 34:1237–44 (1993).

K. Uchida et al., "Michael Addition–Type 4–Hydroxy-2–Nonenal Adducts In Modified Low Density Lipoproteins: Markers For Atherosclerosis," *Biochemistry* 33:12487–12493 (1994).

G. Jürgens et al., "Immunstaining of Human Autopsy Aortas With Antibodies to Modified Apolipoprotein B and Apoprotein(a)," *Arterioscler. Thromb.* 13:1689–99 (1993).

M.R. Jirousek et al., "Electrophillic Levuglandin $E_2$–Protein Adducts Bind Glycine: A Model For Protein Crosslinking," *Prostaglandins* 40(2):187–203 (1990).

S. Toyokuni et al., "The Monoclonal Antibody Specific For The 4–Hydroxy–2–Nonenal Histidine Adduct," *FEBS Letters* 359:189–91 (1995).

M.T. Quinn et al., "Immunocytochemical Detection of Lipid Peroxidation in Phagosomes of Human Neutrophils: Correlation with Expression of Flavocytochrome b," *J. Leukoc. Biol.* 57:415–21 (1995).

U. Singh, "Part II. Studies On The Detection Of Levuglandins," (Aug. 1994).

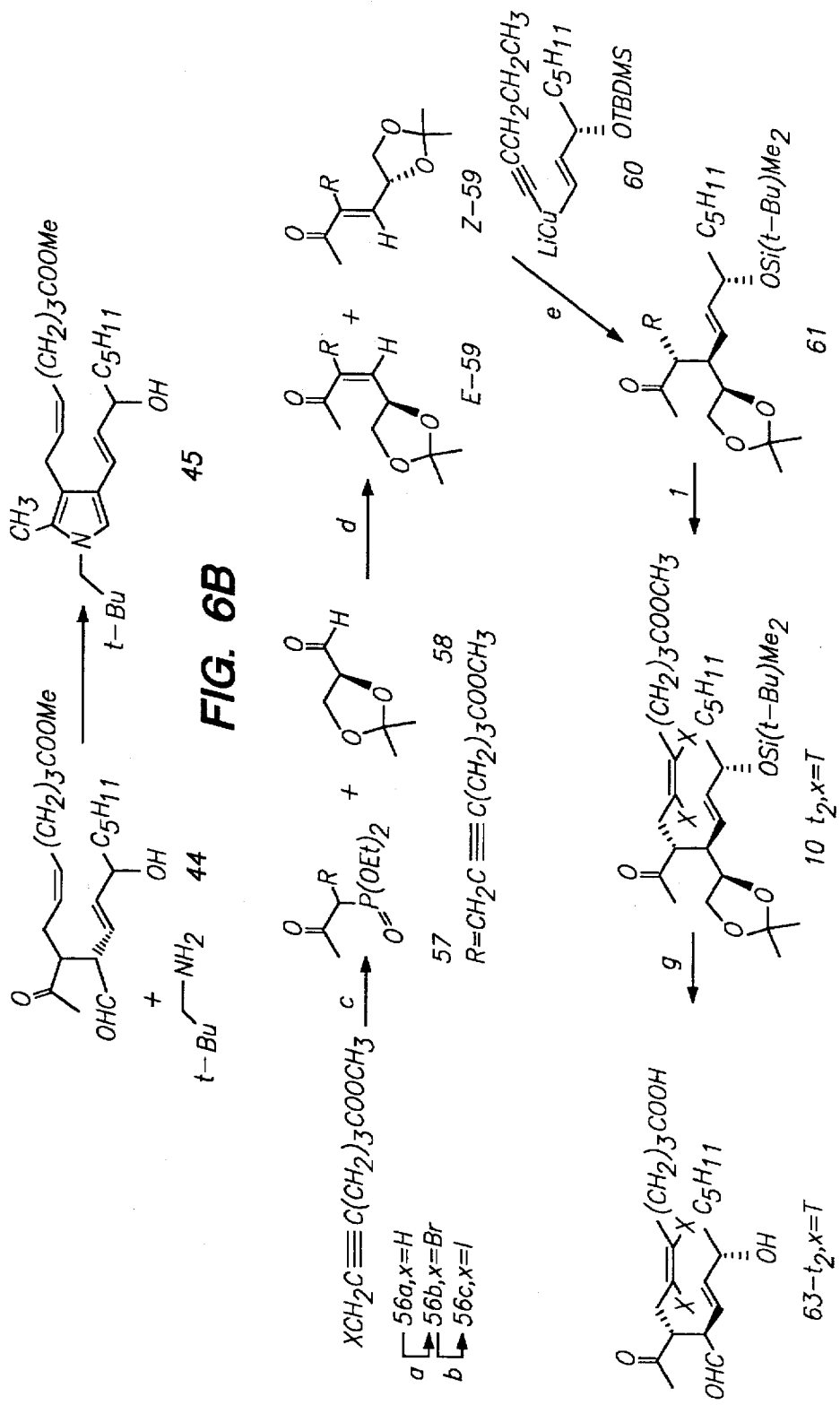

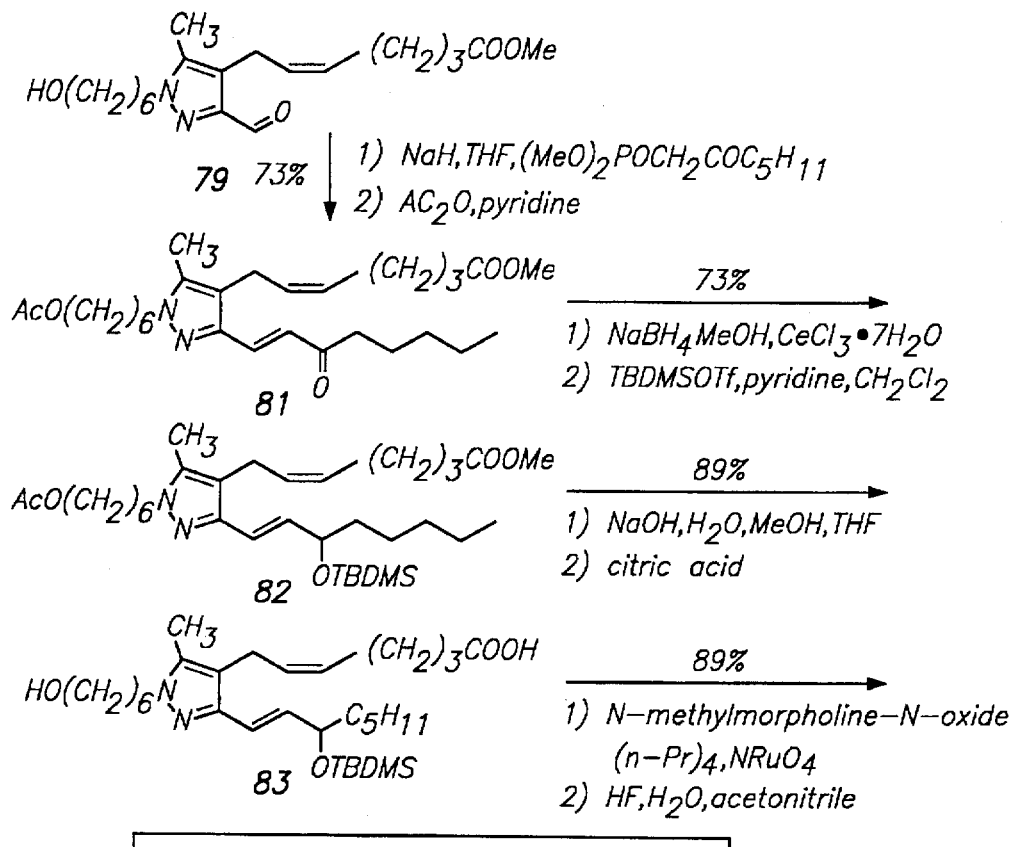
FIG. 8B
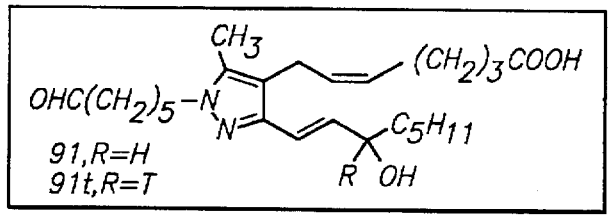
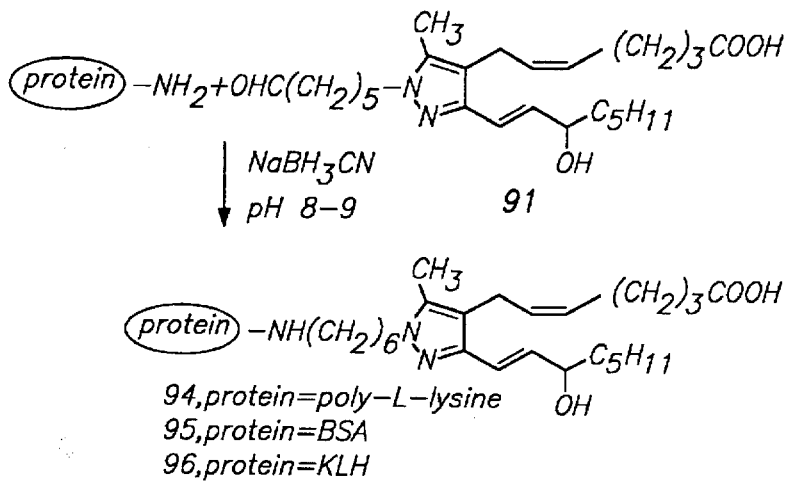
FIG. 8C

ANTIBODIES TO LGE$_2$-PROTEIN ANTIGENS

FIELD OF THE INVENTION

The present invention relates to levuglandin derivatives as antigens for raising antibodies useful in diagnostic assays.

BACKGROUND OF THE INVENTION

Cardiovascular disease is a broad term encompassing many pathologies of the heart and vascular system, including hypertension, stroke, aneurysm, angina, myocardial infarction, and Raynaud's disease. During 1990, cardiovascular disease caused about 43% of the deaths—more than 900,000 people—in the United States. Thus, the number of deaths from cardiovascular disease was nearly as high as the number of deaths from all other causes combined. [J. T. Shepherd, et al., "Report of the Task Force on Vascular Medicine," Circulation 89 (1): 532–35 (1994)].

Cardiovascular disease is also a leading cause of morbidity. Both patients and their families suffer a great deal from the effects of cardiovascular disease. Furthermore, there is a tremendous economic impact associated with such illness. Both the high incidence and the often-severe manifestations of cardiovascular disease necessitate that a large portion of health care workers' time be devoted to the care of patients suffering from the disease state. Moreover, sufferers of cardiovascular disease lose countless numbers of productive hours each year due to their illness. It is important to remember that cardiovascular disease affects many people besides the elderly or those having a familial predisposition. Indeed, the establishment of detailed guidelines directed solely to the evaluation of congenital cardiac problems in pre-adults illustrates that the young are not immune from cardiovascular disease. [D. Driscoll et al. "Guidelines for Evaluation and Management of Common Congenital Cardiac Problems in Infants, Children, and Adolescents," Circulation 90 (4): 2180–88 (1994)].

Currently used techniques for diagnosing cardiovascular disease include electrocardiography, imaging, and measurement of risk factors. However, each of these techniques is plagued by significant drawbacks.

A. Electrocardiography

The traditional approach to diagnosing cardiovascular disease is electrocardiography, a relatively safe and easy method. However, the method, which records electrical currents traversing the heart muscle, has been associated with false-negatives and false-positives in particular patient populations. Though a good initial indicator of various disease states, electrocardiography is an indirect and imperfect measurement of the heart's electrical activity. [M. S. Remetz and R. A. Matthay, "Cardiac Evaluation," Disease-a-Month 38 (6): 338–503 (1992)].

B. Imaging

Intravascular imaging is helpful as a diagnostic tool; however, many of the routinely used imaging methods are quite invasive. In addition, the imaging techniques are expensive, requiring costly equipment and extensively trained personnel to conduct the studies. Three currently used intravascular imaging techniques that provide information about plaque, the vessel wall, and the vessel lumina are fiberoptic angioscopy, contrast angiography, and intravascular ultrasound. [K. M. Coy et al., "Intravascular Ultrasound Imaging: A Current Perspective," J. Am. Coll. Cardiol. 18 (7): 1811–23 (1991)].

Fiberoptic angioscopy allows, among other things, detection of thrombus in acute ischemic syndrome; however, the technique has several limitations, including the amount of information it can provide regarding plaque composition. The technique is quite invasive, necessitating the insertion of a modified microscope into the blood vessel. Indeed, cardiac catheterization involves the insertion of a catheter into a vein or artery, and then the passage of the catheter through the vascular system to the heart.

Contrast angiography is a preferred method for quantitative assessment of atherosclerotic vascular disease; however, it is not very helpful in detecting early or minimal atherosclerotic disease. The method entails the introduction of a radiopaque material into the vessel, followed by radiography to visualize the characteristics of the vessel.

Intravascular ultrasoud devices, recently approved by the FDA, do not have completely defined indications as of yet. Currently being used as an adjunct to contrast angiography, the devices will likely be used extensively in both the qualitative and quantitative assessment of atherosclerotic vascular disease. [K. M. Coy et al., "Intravascular Ultrasound Imaging: A Current Perspective," J. Am. Coll. Cardiol. 18: 1811–23 (1991)].

There are newer imaging techniques. These include scintigraphy, radionuclide ventriculography, and magnetic resonance imaging (MRI). [S. Sirna et al., "Cardiac Evaluation of the Patient With Stroke," Stroke 21 (1): 14–23 (1990)].

Stress thallium-201 myocardial scintigraphy and [$^{201}$Tl] dipyridamole scintigraphy allow obtaining a photographic recording of a labeled pharmaceutical preparation by means of as intillation detector device. [$^{201}$Tl]dipyridamole scintigraphy is preferred when patients with limited exercise capacity are being tested because of dipyridamole's vasodilatory effect. Sensitivities of 75–95% have been reported, but the results depend on the patient population and the criteria that are used in deciding whether or not disease is present.

Radionuclide ventriculography visualizes the cardiac chambers, thereby allowing left ventricular function to be evaluated during exercise. Although the technique is cheaper than stress thallium-201, it has inferior specificity. [S. Sirna et al., "Cardiac Evaluation of the Patient With Stroke," Stroke 21 (1): 14–23 (1990)].

Though also non-invasive, magnetic resonance imaging is not in widespread use because it is generally expensive, and time-consuming than the above-mentioned non-invasive techniques. Clinical use of magnetic resonance imaging primarily involves morphological observations, and the technique is most often associated with the diagnosis of thoracic aortic diseases, paracardiac and intracardiac masses, congenital heart and pericardial disease. [C. B. Higgins and G. R. Caputo, "Role of MR Imaging in Acquired and Congenital Cardiovascular Disease," AJR 161: 13–22 (1993)].

C. Risk Factors

Numerous risk factors are routinely cited as being predictive of the development and exacerbation of cardiovascular disease. These risk factors include lipid disorders, coagulation disorders, diabetes melitis, hypertension, and smoking. [M. Tervahauta et al., "Prevalence Of Coronary Heart Disease and Associated Risk Factors Among Elderly Finnish Men in the Seven Countries Study," Atherosclerosis 104: 47–59 (1993); J. T. Shepherd, et al., "Report of the Task Force on Vascular Medicine," Circulation 89 (1): 532–35 (1994)]. Unfortunately, the "risk factors" are merely that— factors that ostensibly correlate to the risk of developing one of the several forms of cardiovascular disease. Indeed, absence of the risk factors does not preclude cardiovascular disease.

To illustrate, lipid profiles have been studied as predictors of cardiovascular disease. One study identified four types of "lipoprotein abnormalities" and noted that one or more of the abnormalities were present in 50–80% of myocardial infarction survivors. [J. L. Breslow, "Genetics of Lipoprotein Disorders," Circulation 87: (supp. III): III-16–III-21 (1993)]. One of the four "abnormalities," increased low density lipoprotein (LDL) cholesterol levels, has been deemed a significant risk factor for cardiovascular disease. [E. J. Schaefer et al. "Familial lipoprotein disorders and premature coronary artery disease," Atherosclerosis 108 (Supp): S41–S54 (1994)].

In regards to LDL, apolipoprotein B-100 is a 4536 amino acid protein component of LDL that functions as a ligand for the LDL receptor. [B. A. Nassar, "Familial defective apolipoprotein B-100: a cause of hypercholesterolemia and early coronary heart disease," Can. Med. Assoc. J. 148 (4): 579–80 (1993)]. Familial defective apolipoprotein B-100 has recently been identified as a dominantly inherited genetic disorder that causes increased LDL levels with reduced affinity for the LDL receptor. [A. Tybjaerg-Hansen et al., "Familial defective apolipoprotein B-100: detection in the United Kingdom and Scandinavia, and clinical characteristics of ten cases," Atherosclerosis 80: 235–42 (1990)]. Thus, there is a direct relationship between apolipoprotein B-100 and LDL, and, in fact, high levels of apolipoprotein B have been determined to be a risk factor for myocardial infarction on an order comparable to smoking, hypertension and obesity. [J. Woo et al., "Lipids, lipoproteins and other coronary risk factors in Chinese male survivors of myocardial infarction," Intl. J. Card. 39: 195–202 (1993)]. Interestingly, however, the average LDL cholesterol value of subjects (participants in the Farmingham Study who were followed for between 12 and 14 years) who had coronary disease was found to be at or below so-called dangerous levels! [W. B. Kannel and P. W. F. Wilson, "Efficacy of lipid profiles in prediction of coronary disease," Am. Heart J. 124 (3): 768–74 (1992)]. Drs. Kannel and Wilson concluded that more specific and sensitive lipid profiles were needed, indicating that factors currently used as predictors of cardiovascular disease are less than ideal.

What is needed is a non-invasive, sensitive, and specific technique that can be used for both diagnosing the presence of cardiovascular disease and for determining the propensity of a particular person for developing cardiovascular disease. The technique should not rely on predictive factors, but instead should be based on a definitive indicator related to abnormal cardiovascular function. Moreover, the technique should be relatively inexpensive and easy to use, and the results obtained should be easy to interpret. Finally, the usefulness of the technique should not be limited to a specific patient population, nor by the characteristics of a particular patient.

SUMMARY OF THE INVENTION

The present invention is directed at levuglandin (LG) derivatives or adducts as antigens for generating antibodies useful in diagnostic assays. Specifically, the present invention contemplates the use of levuglandin-derived protein-bound pyrrole adducts to raise antibodies that can be used to detect physiological abnormalities, such as certain forms of cardiovascular disease.

The adducts contemplated by the present invention may be generated by the reaction of a levuglandin, generally levuglandin $E_2$ ($LGE_2$), with a free amino group of a protein; this reaction leads to the formation of a five-membered heterocyclic structure, a pyrrole moiety, containing the amino nitrogen as the sole heteroatom. In this manner, a carrier protein can be complexed with a levuglandin to form a LG-carrier protein-bound pyrrole adduct that serves as an immunogen. The immunogen can then be injected into an animal to raise antibodies.

The antibodies generated by the LG-carrier protein-bound pyrrole adducts can be used to detect adducts of $LGE_2$ with human low density lipoprotein (LDL), or adducts with other moieties like lipoprotein (a), by means of an enzyme-linked immunosorbent assay; these adducts are thought to be indicative of lipid-related abnormalities. The adducts detected, which may be deemed LG-specific protein adducts, are believed to be generated through either an enzymatic or a non-enzymatic modification of arachidonic acid or a derivative thereof. Thus, LG-carrier protein-bound pyrrole adducts are used to generate antibodies that react with LG-specific protein adducts.

$LGE_2$-protein adduct immunoreactivity was generated during in vitro free-radical oxidation of human low-density lipoprotein (LDL). The level of immunoreactivity increased with the time of oxidation, reaching a maximum within 3–6 hours and showing no decrease over 23 hours. The epitopes detected in oxidized LDL (oxLDL), but not in native LDL, may arise by the generation of LG-phospholipids from arachidonyl phospholipids; however, hydrolysis of the phospholipid moiety must occur to generate a fully-immunoreactive LG-protein adduct. LG-protein immunoreactivity was linked to the diagnosis of specific disease states, as elevated levels of immunoreactivity were found in the plasma of patients with atherosclerosis and renal failure.

The present invention contemplates a method of producing antibodies, comprising: a) reacting a levuglandin with a carrier protein to form a levuglandin-carrier protein-bound pyrrole adduct; b) injecting said levuglandin-carrier protein-bound pyrrole adduct into an animal under conditions such that antibodies are produced; and c) collecting said antibodies from said animal. In particular embodiments said animal is a rabbit.

In some embodiments, the present invention further comprises the step, after step c), of purifying said antibodies. Moreover, in particular embodiments, said purifying step comprises contacting said antibodies with Protein A.

In certain embodiments of the present invention, said levuglandin is levuglandin $E_2$ ($LGE_2$). When said levuglandin is $LGE_2$, said levuglandin-carrier protein-bound pyrrole adduct may be, but is not limited to, $LGE_2$-human serum albumin, $LGE_2$-bovine serum albumin, or $LGE_2$-keyhole limpet hemocyanin.

Furthermore, the present invention contemplates said antibodies being capable of detecting a levuglandin-specific protein adduct. In particular embodiments, said levuglandin-specific protein adduct is levuglandin $E_2$-apolipoprotein B.

The present invention also contemplates a method of performing a diagnostic assay, comprising: a) providing: (i) antibodies to a levuglandin-carrier protein-bound pyrrole adduct, said adduct containing a levuglandin component and a protein component, and (ii) a sample to be tested for the presence of antigens reactive with said antibodies; b) combining said sample and said antibodies to from a reaction solution; and c) screening said reaction solution for the presence of a reaction between said antigens and said antibodies.

In some embodiments of the method, said antibodies are capable of detecting a levuglandin-specific protein adduct. In particular embodiments, said levuglandin-specific protein adduct is $LGE_2$-LDL; in other embodiments, said levuglandin specific protein adduct is $LGE_2$-lipoprotein (a).

In particular embodiments, said sample is human plasma. Moreover, said human plasma sample may be dialyzed plasma in particular embodiments. This may be important because, while the antibodies could weakly cross-react with prostaglandins (PGs) and isoPGs, this reactivity can be removed by dialysis. By contrast, the immunoreactivity arising from LG-LDL is non-dialyzable, thus allowing isolation of the immunoreactivity generated by levuglandin adducts.

Additionally, the present invention contemplates a method of performing a diagnostic assay, comprising the following steps in the order presented: a) providing: (i) a first solution comprising immunoglobulin-containing antibodies to a specific protein, said antibodies produced in a first species, (ii) a sample suspected of containing levuglandin-specific protein adducts, said adducts containing a levuglandin component and a protein component, (iii) a plurality of test wells containing protein-binding sites; b) adding said first solution to said plurality of test wells under conditions such that said antibodies are immobilized via said protein binding sites; c) adding said sample to said plurality of test wells; and d) screening for the presence of levuglandin-specific protein adduct.

In some embodiments, said screening step comprises: a) adding a second solution containing (i) antibodies to a specific protein and (ii) a labeling component, said antibodies from said second solution produced in said first species; and b) quantifying the amount of levuglandin-specific protein adduct in said sample after adding said second solution. It is not intended that the invention be limited by the nature of the labeling component. The labeling component may constitute any marker, characteristic, or factor by which the screening step may be enhanced. For example, in certain embodiments, the labeling component may be $^{125}$iodine.

In contrast, in other embodiments said screening step comprises the following steps in the order presented: a) adding antibodies raised in a second species; b) adding a second solution containing (i) anti-immunoglobulin to said second species and (ii) a labeled component; and c) quantifying the mount of levuglandin-specific protein adduct in said sample. Again, the invention is not limited by the nature of the labeling component.

In some embodiments of the present invention, after step b), a blocking buffer is incubated with said test wells, thereby allowing said blocking buffer to bind to any protein binding sites not bound by said first solution. Moreover, other embodiments comprise the steps, after steps b) and c), of washing said test wells with a washing buffer.

DEFINITIONS

To facilitate understanding of the invention and the terminology used in the description of the invention, a number of terms are described below.

The term "levuglandins" ("LGs") refers generally to a class of compounds related to the prostaglandins. [See M. E. Coldyne, "Prostaglandins & Other Eicosanoids," in *Basic And Clinical Pharmacology*, Ch. 17, pp. 211–221; B. G. Katzung, ed., (Appleton & Lange, Los Altos, Calif.) (3rd Ed., 1987)]. Like the prostaglandins, levuglandins are derived from arachidonic acid, a linear 20-carbon polyunsaturated fatty acid. More specifically, levuglandins may be formed in vivo from the unstable, bicyclic prostaglandin $H_2$ ($PGH_2$); $PGH_2$ is an endoperoxide wherein the peroxide moiety (—O—O—) bridges carbons 9 and 11. As depicted below, $PGH_2$ can rearrange under aqueous conditions to form γ ketoaldehydes, levuglandin $E_2$ ($LGE_2$) and levuglandin $D_2$ ($LGD_2$). The nomenclature of these levuglandins is derived from their chemical relationship to $PGE_2$ and $PGD_2$, which can hypothetically be formed through aldol condensation of the respective levuglandins.

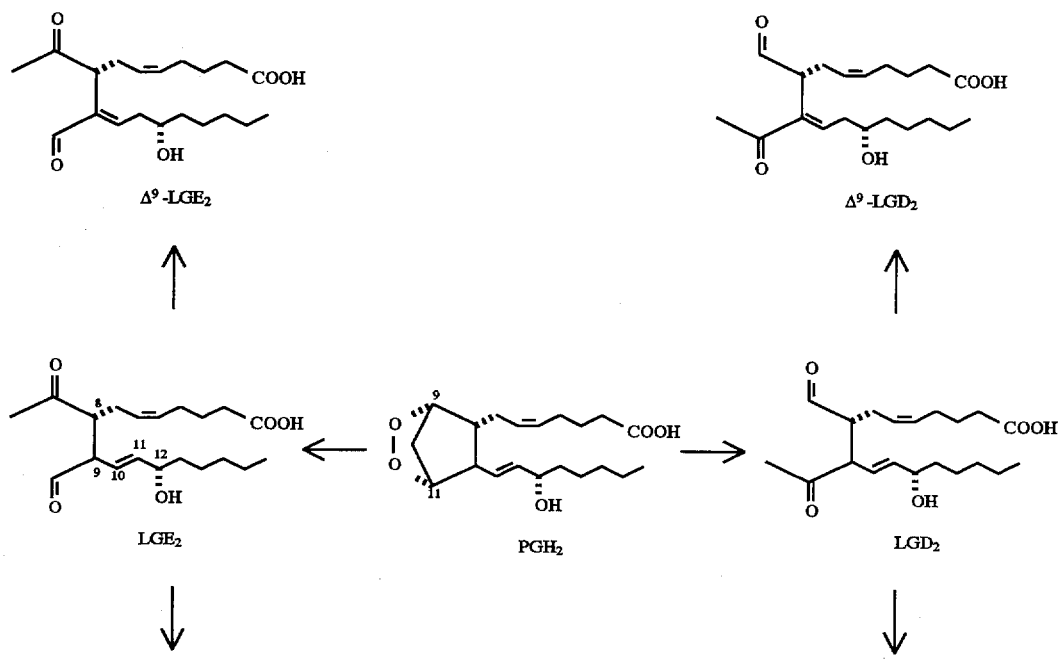

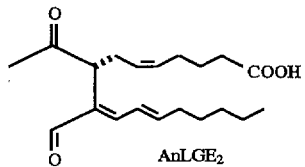

AnLGE₂

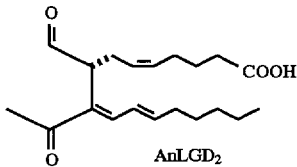

AnLGD₂

In terms of their stability, levuglandins are sensitive vinylogous β-hydroxy carbonyl compounds that readily dehydrate to form the anhydro analogs AnLGE2 and AnLGD$_2$. Moreover, the C10–C11 double bond (i.e., the double bond connecting carbon-10 and carbon-11) may also migrate to form the more stable conjugated isomers $\Delta^9$-LGE$_2$ and $\Delta^9$-LGD$_2$.

The present invention is not limited to any particular levuglandin. Indeed, antibodies may be produced from any levuglandin stereoisomer (i.e., compounds differing in the spatial arrangement of bonded groups around an asymmetric carbon), including diastereoisomers (i.e., compounds that are not mirror images of one another) and enantiomers (i.e., compounds that are mirror images of one another). As depicted in the schematic above, levuglandins have three stereocenters: C8, C9, and C12. Initially, it should be noted that antibodies generated by levuglandin-carrier protein-bound pyrrole adducts recognize the pyrrole moiety of levuglandin-specific protein adducts. However, the C8 and C9 positions of levuglandins become part of the pyrrole moiety during adduct formation, thus losing their status as stereocenters. On the other hand, the C12 position remains a stereocenter after adduct formation. Furthermore, it is believed that the enzymatic pathway (e.g., cyclooxygenase) generally forms 12(S) isomers, whereas the free-radical pathway is non-stereospecific, forming both 12(S) and 12(R) isomers. Therefore, the present invention specifically contemplates the use of LGE$_2$ [8(R)-acetyl-9(R)-formyl-12(S)-hydroxyl-5(Z),10(E)-heptadecadienoic acid] or isomers with any combination of configurations at the C8, C9, and C12 positions.

The term "lipoprotein" refers broadly to complexes or compounds containing lipid and protein. The lipoproteins that are associated with atherosclerosis, coronary artery disease, and other lipid-related disorders include low-density lipoprotein (LDL), very low-density lipoprotein (VLDL), intermediate-density lipoprotein (IDL), and high-density lipoprotein (HDL). The term "lipoprotein (a)" ("Lp (a)") refers to a lipoprotein-associated antigen located in human plasma; it is an altered form of LDL with a large glycoprotein, apolipoprotein (a), complexed with the apolipoprotein B-100 moiety of LDL by a disulfide bond. [J. L. Breslow, "Genetics of Lipoprotein Disorders," Circulation 87: (supp. III): III-16–III-21 (1993)].

The term "apolipoprotein" ("apo") refers broadly to the group of proteins involved in the direct control of lipoprotein transport; this group includes apo A-I, A-II, A-IV, B, C-I, C-II, C-III, D, E, and (a). The term "apolipoprotein B" ("apo B"), also termed "apoliprotein B-100" ("apo B-100"), refers to the sole protein found in the LDL particle. Apo B-100, which is synthesized in the liver and secreted in VLDL, is a 4536 amino acid polypeptide. Apo B-100 functions as a ligand for the LDL receptor; binding of apo B-100 to the LDL receptor on a liver cell leads to internalization of the LDL particle, and, ultimately, lysosomal degradation. [See, generally, B. A. Nassar, "Familial defective apolipoprotein B-100: a cause of hypercholesterolemia and early coronary heart disease," Can. Med. Assoc. J. 148 (4): 579–80 (1993); J. L. Breslow, "Genetics of Lipoprotein Disorders," Circulation 87: (supp. III): III-16–III-21 (1993)].

The term "animal" refers broadly to any living organism capable of generating an immune response upon introduction of an immunogen. Animals include, but are not limited to, rabbits, goats, and sheep; humans are also encompassed by the term.

The term "immunogen" ("antigen") refers to any substance capable of generating antibodies when introduced into an animal. By definition, an immunogen must contain at least one epitope (the specific biochemical unit capable of causing an immune response), and generally contains many more. Proteins are most frequently used as immunogens, but lipid and nucleic acid moieties complexed with proteins may also act as immunogens. The later complexes are often useful when smaller molecules with few epitopes do not stimulate a satisfactory immune response by themselves.

The term "antibody" refers to immunoglobulin evoked in animals by an immunogen (antigen). It is desired that antibody demonstrate specificity to the immunogen, or, more specifically, to the epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The term "Protein A" refers to a ligand, produced by a strain of *Staphylococcus aureus*, containing multiple binding sites. Protein A binds to the Fc domain of immunoglobulin G of many species with high affinity and may be used in antibody affinity chromatography. Though not intended to be limited to any specific column or manufacturer, PROTEIN A SUPEROSE® columns produced by Pharmacia may be used with the present invention.

The term "carrier protein" refers to a protein without any medical relevance, employed merely for the convenience of generating antibodies or coating ELISA plates. Examples of carrier proteins include bovine serum albumin (BSA), human serum albumin (HSA); keyhole limpet hemocyanin (KLH), and poly-L-lysine. As explained above, the carrier protein may be complexed with another compound to create an immunogen.

The terms "levuglandin-carrier protein-bound pyrrole adduct", "levuglandin-carrier protein-bound pyrrole derivative", and the like refer to a general class of compounds used as immunogens to generate antibodies that are cross-reactive with levuglandin-specific protein adducts. These compounds are generated by reacting a levuglandin (or a complex containing a levuglandin and another moiety like a phospholipid) with a carrier protein; as described below and depicted in FIG. 1, the reaction of the levuglandin with the protein entails the formation of a pyrrole moiety, thus prompting the name levuglandin-carrier protein-bound pyrrole adduct. In the description that follows, it is important to note that the nomenclature used to describe specific levuglandin-carrier protein-bound pyrrole adducts has been simplified. Thus, reference to an adduct between a levuglandin and a carrier protein (e.g., LGE$_2$-HSA, LGE$_2$-BSA, and LGE$_2$-KLH) is meant to refer to the corresponding levuglandin-carrier protein-bound pyrrole adduct. Conversely, when a pyrazole isostere adduct is being referred to, the term "pyrazole" will be definitively stated in the description.

The term "specific protein" refers to a particular protein that forms adducts with levuglandin (LG) in vivo. An example of a specific protein is apolipoprotein B.

The term "levuglandin-specific protein adduct" refers to the formation of a levuglandin-protein adduct that is recognized by antibodies raised by a levuglandin-carrier protein-bound pyrrole adduct.

The terms "dialysis", "dialyzed" and the like refer broadly to the separation of substances in solution by means of their unequal diffusion through semipermeable membranes. The term "peritoneal dialysis" involves the separation and removal from the body of soluble substances and water across the peritoneum through the use of a fluid (dialysis solution). In peritoneal dialysis, fluid is introduced into the peritoneal cavity, remains in the peritoneal cavity for a period of time to allow for diffusion of soluble substances and water across the peritoneum and into the fluid, and then is removed from the peritoneal cavity. The term "fluid resulting from peritoneal dialysis" refers to this fluid that is removed from the peritoneal cavity.

The term "cerebrospinal fluid" refers to the fluid, secreted by the choroid plexuses of the ventricles of the brain, that fills the ventricles and the subarachnoid cavities of the brain and spinal cord.

The term "synovial fluid" refers to the fluid that functions as a lubricant in a joint, tendon sheath, or bursa.

The term "sample" is used in its broadest sense. On one hand, it is meant to include a specimen or culture; on the other hand, it is meant to include both biological and environmental samples. Biological samples may be animal, including human, fluid, solid (e.g., stool) or tissue, liquid and solid food products and ingredients such as dairy items, vegetables, meat and meat by-products, and waste. Biological samples include blood products, such as plasma, serum and the like. Environmental samples, include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

DESCRIPTION OF THE FIGURES

FIG. 6B is a schematic of the synthetic pathway of the methyl ester of structure 5a [3-(6-carbomethoxy-2(Z)-hexenyl)-4-(3-hydroxy-1(E)-octenyl)-2-methyl-1-neopentylpyrrole; structure 45] from an LGE$_2$-methyl ester.

FIG. 7 is a schematic of the synthetic pathway of structure 10-t2 [8-acetyl-12-t-butyldimethylsiloxy-5,6-ditritio-9-(1(S),2-isopropylidenedioxyethyl)-5(Z),10(E)-heptandecadienoic acid].

FIG. 8B is a schematic depicting the synthesis of structure 91 [4-(6-Carboxy-2(Z)-hexenyl)-3-(3-hydroxy-1(E)-octenyl)-5-methyl-1-(6-oxohexyl)pyrazole] from structure 79 [4-(6-Carbomethoxy-2(Z)-hexenyl)-1-(6-hydroxyhexyl)-5-methylpyrazole-3-carboxaldehyde].

FIG. 8C is a schematic depicting the synthesis of the BSA-pyrazole isostere conjugate from structure 91 [4-(6-Carboxy-2(Z)-hexenyl)-3-(3-hydroxy-1(E)-octenyl)-5-methyl-1-(6-oxohexyl)pyrazole].

DESCRIPTION OF THE INVENTION

Figure 1:
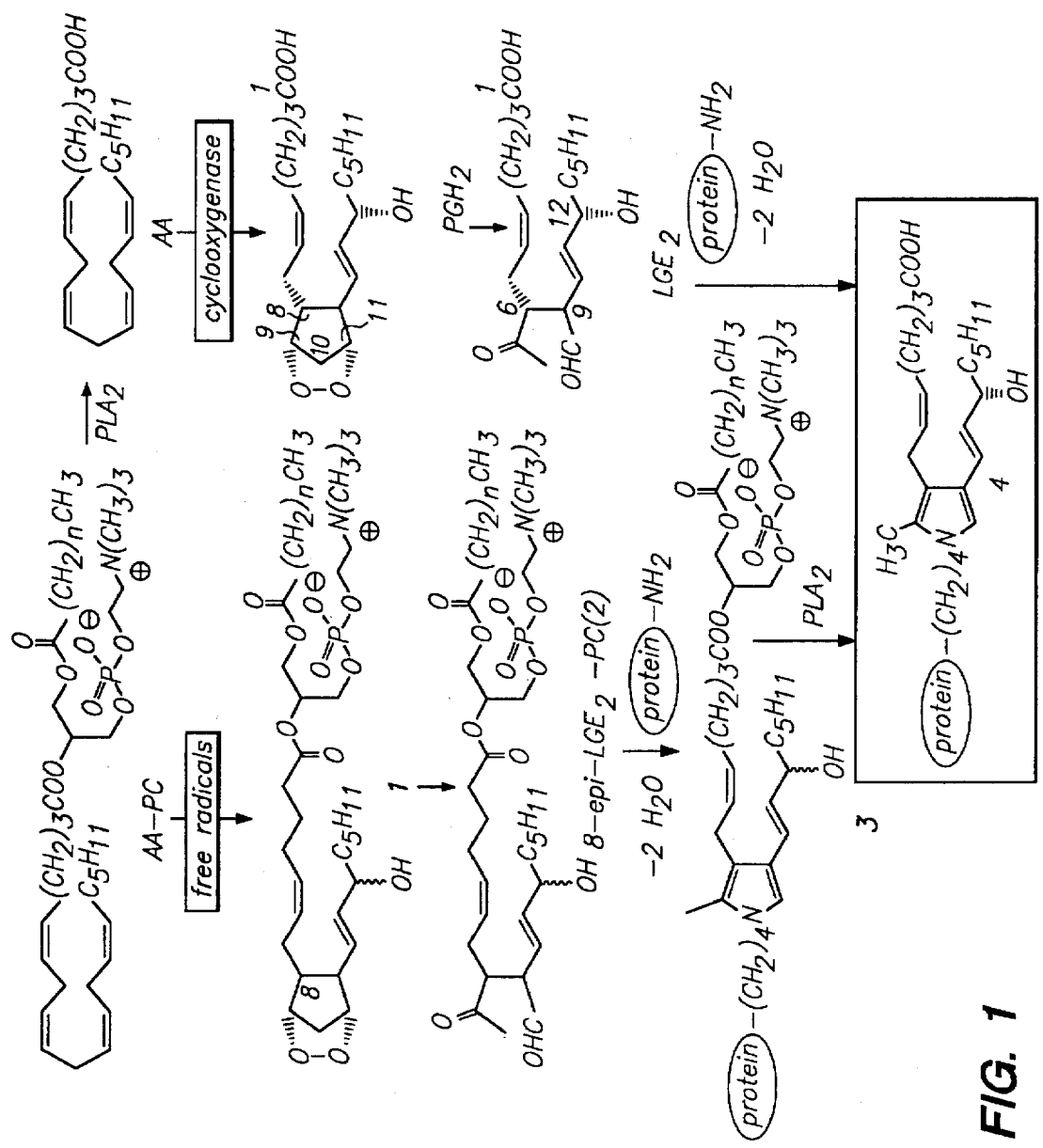
FIG. 1 is a schematic of the enzymatic and non-enzymatic pathways from an arachidonyl phospholipid to a levuglandin-derived protein-bound pyrrole derivative. The numbers in parenthesis refer to structure numbers (discussed in the specification).

The present invention relates to levuglandin derivatives as antigens for raising antibodies useful in diagnostic assays. In particular, the invention utilizes antibodies reactive with levuglandin-carrier protein adducts as reagents to measure and diagnose disease.

The Description Of The Invention is divided into four parts: I) Oxidative Injury; II) Adducts Of The Present Invention; III) LG-Protein Adducts As Immunogens And Preparation Of Antibodies; and IV) Diagnostic Assays.

I. Oxidative Injury

Oxidative injury is known to be a complex process that involves both enzymatic (e.g., cyclooxygenase) and nonenzymatic (e.g., free-radical) oxidative metabolism of unsaturated fatty acids. Mounting evidence supports the hypothesis that oxidative modification of low density lipoprotein (LDL) is fundamentally involved in the etiology of atherosclerosis. [D. Steinberg et al., N. Eng. J. Med. 320: 915–24 (1989)]. Therefore, a thorough understanding of the chemical structure of oxidized LDL (oxLDL) and the molecular mechanisms of its formation may provide a basis for the rational design of therapeutic counter-measures. However, the problem is complicated because oxLDL is not a single, defined chemical entity. Depending on the extent of oxidation and on the various oxidized products generated, oxLDL may exhibit a broad spectrum of biological effects. [S. Parthasarathy et al., Annu. Rev. Med. 43: 219–25 (1992)]. Oxidative modification of LDL involves: (1) the formation of reactive products by oxidation of lipid constituents, such as phosphatidylcholine esters of fatty acids, and (2) the formation of adducts between those products and proteins, especially apolipoprotein (apo) B. [D. Steinberg et al., N. Eng. J. Med. 320: 915–24 (1989)]. Prominent during the oxidation of LDL is the disappearance of linoleic and arachidonic esters and the formation of numerous aldehydic fragmentation products. [H. Easterbauer et al., J. Lipid Res. 28: 495 (1987)]. Two of these fragmentation products, malondialdehyde (MDA) and 4-hydroxynonenal (HNE), have been studied extensively because they conjugate with apo B and because the MDA-LDL and HNE-LDL adducts are atherogenic, in contrast with native LDL. [A. M. Fogelman et al., Proc. Natl. Acad. Sci. USA 77: 2214–18 (1980); G. J. Jürgens et al., Biochim. Biophys. Acta 875: 103–14 (1986)].

New modifications of LDLs have been discovered and are herein described using antibodies raised against protein adducts of levuglandin (LG) $E_2$; thus, the LG-protein adducts may be deemed "immunoreactive products." As will be discussed, generation of the immunoreactive products is believed to entail peroxidative free-radical conversion of arachidonyl phospholipids into endoperoxides. The endoperoxides then rearrange to form a diverse family of levulinaldehyde derivatives that avidly bind to proteins. The modifications to LDLs can be generated in vitro by promoting oxidative damage with $Cu^{+2}$.

Importantly, the antibodies that are generated to the immunoreactive products do not exhibit cross-reactivity with other naturally-occurring LDL adducts (i.e., MDA- or HNE-LDL adducts). While the antibodies do weakly cross-react with prostaglandins (PGs) and isoPGs, those fatty acid metabolites can be removed from oxLDL by dialysis, whereas the immunoreactivity arising from LG-LDL is non-dialyzable.

The immunoreactive products have been shown to occur in plasma, cerebrospinal fluid (CSF), synovial fluid, and the fluid resulting from peritoneal dialysis in several disease states. In vivo studies indirectly demonstrate the occurrence of high concentrations of immunoreactive products in patients with atherosclerosis and in patients with renal insufficiency. Moreover, abnormally high levels of immunoreactivity was detected in brain microvessels of a patient suffering from Alzheimer's Disease.

II. Adducts of the Present Invention

A. Background

The use of protein conjugates or adducts has previously been described in several contexts. For example, the Maillard Reaction is a well-studied non-enzymatic reaction between glucose and the free amino groups of amino acids (e.g., L-lysine) and proteins. The Maillard Reaction has been used to create glucose-derived pyrroles used as immunogens in rabbits. The resulting polyclonal antibody was shown to react with the albumin-rich fraction of human plasma, and this reactivity was correlated with a disease state. [F. Hayase et al., "Aging of Proteins: Immunological Detection Of A Glucose-Derived Pyrrole Formed During Maillard Reaction In Vivo," J. Biol. Chem. 263: 3758–64 (1989)]. Moreover, KLH-pyrraline conjugates have also been used as immunogens, and highly specific immunoreactivity was detected in the renal vasculature of mice with arteriolosclerosis. [S. Miyata and V. Monnier, Immunohistochemical Detection Of Advanced Glycosylation End Products In Diabetic Tissues Using Monoclonal Antibody To Pyrraline," J. Clin. Invest. 89: 1102–12 ( 1992)].

LG-carrier protein pyrazole isostere adducts are known in the art. Poly-L-lysine and BSA have been used as immunogens. [S. Kim, "Part 1. Halichondrin B: Synthesis Of An H-Ring Intermediate; Part 2. Levuglandin-Protein Adducts: Synthesis Of An Antigen For Immunoassay, Thesis, Case Western Reserve University (1992); K. K. Murthi, "Chapter 2. Levuglandins: Detection And Biological Chemistry," Thesis, Case Western Reserve University (1992)]. LG-carrier protein pyrazole isostere adducts, with KLH as the carrier protein, have also been used as immunogens. [E. DiFranco, "Part II. An Immunoassay For Protein-Bound Levuglandin-Derived Pyrroles," Thesis, Case Western Reserve University (1994)].

B. Chemical Basis For The Formation Of The Conjugates In Vivo

In the description that follows, reference to a structure number (e.g., structure 4) is to the indicated structure shown in the figures and in Table 1. As is evident from a review of the figures and Table 1, the structure number may refer to a particular compound (e.g., structure 6) or to a particular compound bound to a generic adduct like a protein (e.g., structure 4). Of course, the present invention is not limited to the particular structures set forth in the disclosure; the use of other structures is considered to be within the spirit and scope of the present invention.

TABLE 1

STRUCTURE 1
phospholipid endoperoxide:
2-lysophosphatidylcholine (PC) ester
formed from AA-PC

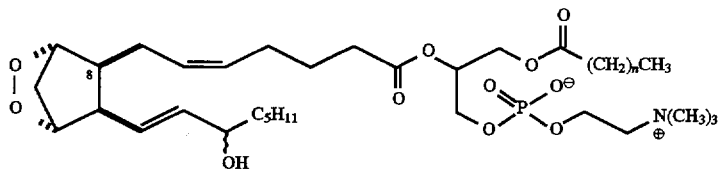

STRUCTURE 2
8-epi-LGE$_2$-PC

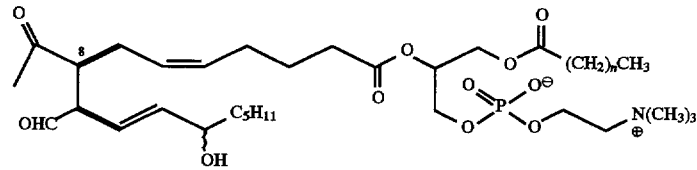

STRUCTURE 3
LG-derived pyrrole phospholipids

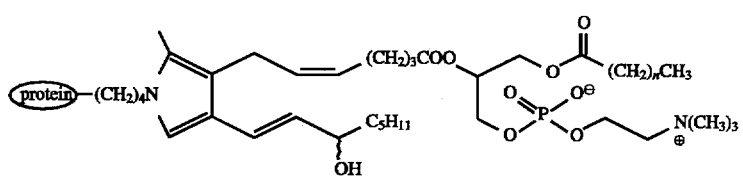

STRUCTURE 4
LG-derived protein-bound pyrrole
derivative/adduct

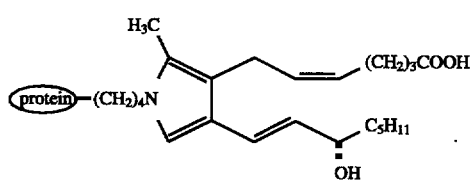

STRUCTURES 5a, 5b
5a: R = t-Bu-CH$_2$—
[3-(6-carboxy-2-Z-hexenyl)-1-neopentyl-4-
(3-hydroxy-1-E-octenyl)-2-methylpyrrole]
5b: R = HO(CH$_2$)$_6$—
[3-(6-carboxy-2-Z-hexenyl)-1-(6-
hydroxyhexyl)-4-(3-hydroxy-1-E-octenyl)-2-
methylpyrrole]

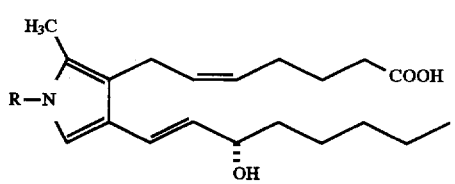

STRUCTURE 6
(Z)-7-hydroxy-5-heptenoic acid

STRUCTURE 7
(E)-1-chloro-1-octen-3-ol

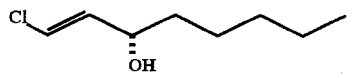

STRUCTURES 8a, 8b
8a: R$^1$= H, R$^2$= C$_5$H$_{11}$
[6-(-2-pentylpyrrol-1-yl)hexanoic acid]
8b: R$^1$= CHO, R$^2$= CH$_2$OH
[6-(2-formyl-5-hydroxymethylpyrrol-1-
yl)hexanoic acid]

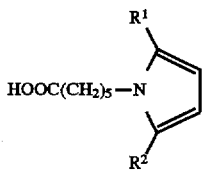

TABLE 1-continued

STRUCTURE 9
KLH-pyrazole isostere antigen

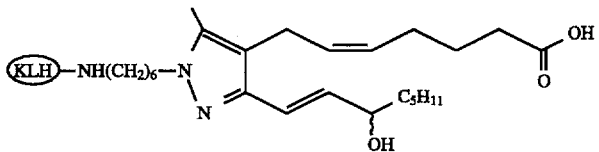

STRUCTURE 10
2-[8-acetyl-12-t-butyldimethylsiloxy-9-
(1(S),2-isopropylidenedioxyethyl)-
5(Z),10(E)-heptadecadienoic acid

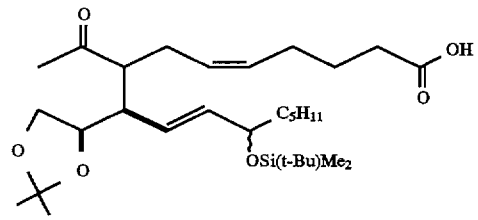

STRUCTURE 11
2-[8-(R)-Acetyl-12-t-butyldimethylsiloxy-9-
(1(S),2-isopropylidenedioxyethyl)-
5(Z),10(E)-heptadecadienoyl]-1-palmitoyl
Phosphatidylcholine

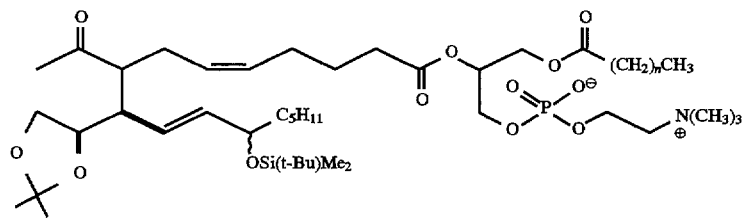

FIG. 1 depicts the major chemical steps involved in the formation of a LG-derived protein-bound pyrrole derivative (structure 4) from both cyclooxygenase and free-radical oxidative pathways. Because cyclooxygenase only converts free arachidonic acid (AA) to an endoperoxide intermediate, this pathway is regulated by enzymatic (e.g., phospholipase A$_2$ (PLA$_2$)) release of AA from AA-PC. [R. A. Fishman and P. H. Chan, Trans. Am. Neuro. Assoc. 106: 1 (1981); B. K. Siesjo and T. Wieloch, *Cerebrovascular Diseases* (M. Reivich and H. Hurtig, eds.; Raven, N.Y.) pp. 251–74 (1983)]. In contrast, the free-radical pathway oxidizes AA-PC directly and in preference to free AA.

An understanding of the cyclooxygenase pathway serves as a guide to an understanding of how structures 1–4 are generated in the free-radical pathway. Referring to FIG. 1, the endoperoxide PGH$_2$ is produced from arachidonic acid (AA) by the enzyme cyclooxygenase. Because it is unstable (t$_{1/2}$=5 min at 37° C.), PGH$_2$ rearranges nonenzymatically under the conditions of its cyclooxygenase-promoted biosynthesis. The rearrangement generates prostaglandins (not shown) [M. Hamberg and B. Samuelsson, Proc. Natl. Acad. Sci. USA 70: 899–903 (1973); M. Hamberg et al., Proc. Natl. Acad. Sci. USA 71: 345–49 (1974); D. H. Nugteren and E. Hazelhof, Biochim. Biophys. Acta 326: 488–93 (1973); A. Raz et al., Biochim. Biophys. Acta 488: 322–29 (1977); D. H. Nugteren and E. Christ-Hazelhof, Adv. Prostaglandin Thromboxane Res. 6: 129–37 (1980)] and secoprostanoic acid levulinaldehyde derivatives, e.g., levuglandin E$_2$ (LGE$_2$). [R. G. Salomon et al., J. Am. Chem. Soc. 106: 6049–60 (1984)]. Earlier studies have shown that LGE$_2$ binds covalently with proteins [R. G. Salomon et al., Prostaglandins 34: 643–56 (1987)] and that LG-derived protein-bound pyrrole derivatives (structure 4) are major products of this reaction. [R. Iyer et al., J. Org. Chem. 59: 6038–6043 (1994)].

Figure 2:
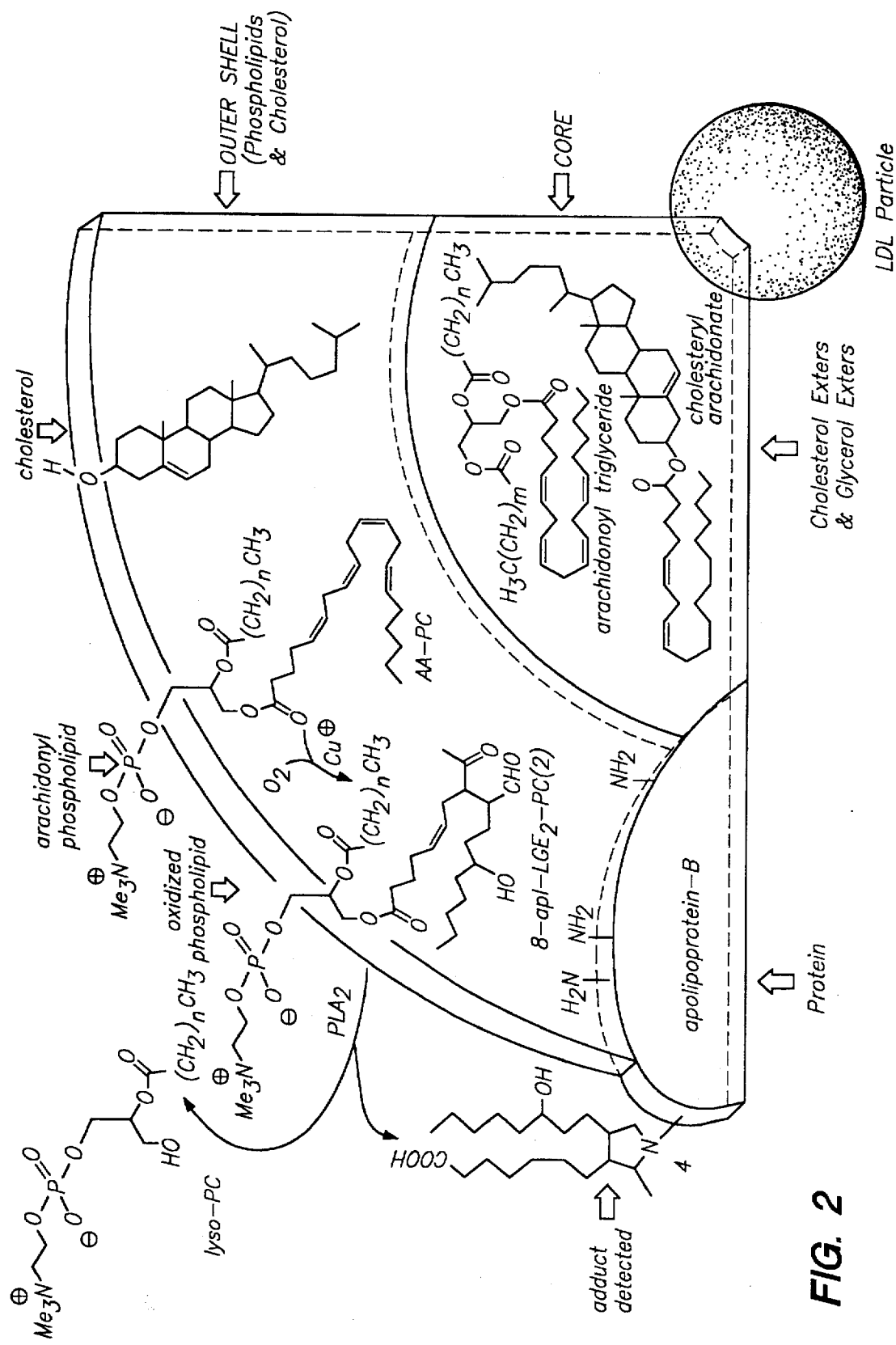
FIG. 2 diagrammatically shows oxidation of an LDL particle showing the anatomy of an expanded segment containing arachidonyl phosphatidylcholine (AA-PC), a derived levuglandin phosphatidylcholine ester (8-epi-LGE$_2$-PC), and an immunoreactive LG-derived pyrrole adduct (structure 4) of apo B.

It is believed that oxidative protein modifications are produced from phospholipid endoperoxides generated in LDL. [S. M. Lynch et al., J. Clin. Invest. 93: 998–1004 (1994)]. Again referring to FIG. 1, a nonenzymatic, free-radical oxidative pathway can be used to generate phospholipid endoperoxides (e.g., the 2-lysophosphatidylcholine (PC) ester (structure 1)) from arachidonyl phospholipids (e.g., AA-PC). [J. D. Morrow et al., Anal. Biochem. 184: 1–10 (1990)]. As noted above, the free-radical pathway oxidizes AA-PC directly. Thereafter, structural modification of structure 1 is parallel to that of the structurally-similar prostaglandin endoperoxide PGH$_2$. Thus, analogous to the conversion of PGH$_2$ into LGE$_2$, one would expect that nonenzymatic rearrangement of structure 1 would produce a LG-phospholipid, e.g., 8-epi-LGE$_2$-PC (structure 2), and that this γ-keto aldehyde would be rapidly sequestered by covalent adduction to proteins such as apo B. (See FIG. 2, which diagrammatically depicts oxidation of an LDL particle showing the anatomy of an expanded segment containing arachidonyl phosphatidylcholine (AA-PC), a derived levuglandin phosphatidylcholine ester (8-epi-LGE-$_2$-PC), and an immunoreactive LG-derived pyrrole adduct (structure 4) of apo B).

Parallel to LGE$_2$ covalently binding with proteins, Paal-Knorr condensation [A. H. Jackson in *Comprehensive Organic Chemistry*, (D. Barton and D. W. Ollis, eds.) Vol. 4, p. 276 (1980)] of LG phospholipids (structure 2) with protein amino groups would generate pyrrole phospholipids (structure 3). Hydrolysis of the ester linkage in structure 3 would release lyso-phosphatidylcholine and generate the same LG-derived pyrrole (structure 4) as that produced by the cyclooxygenase pathway. One could anticipate that such hydrolysis would occur, in conjunction with oxidative modification of LDL, because the release of 2-lyso-phosphatidylcholine was known to accompany the conversion of LDL to oxLDL. [U. P. Steinbrecher et al., Proc. Natl. Acad. Sci. USA 81: 3883 –87 ( 1984); U. P. Steinbrecher et al., Atherosclerosis 7: 135–43 ( 1987); U. P. Steinbrecher, J. Biol. Chem. 262: 3603–08 (1987)]. In fact, LDL as well as isolated apo B exhibit PLA$_2$-activity toward phospholipids containing an oxidized fatty acyl chain at position 2. [U. P.

Steinbrecher and P. H. Pritchard, J. Lipid Res. 30: 305–15 (1989); S. Parthasarathy and J. Barnett, Proc. Natl. Acad. Sci. USA 87: 9741–45 (1990); N. Reisfeld et al., FEBS Lett. 315: 267–70 (1993)].

Previous studies with LDL containing 2-(1-$^{14}$C-arachidonyl)phosphatidylcholine showed that, unlike MDA or HNE, some of the major lipid-derived products that become bound to protein as a consequence of LDL oxidation retain the carbonyl carbon of their fatty ester precursor. [U. P. Steinbrecher, J. Biol. Chem. 262: 3603–08 (1987)]. It is noteworthy, therefore, that the postulated protein modifications of structure 3 and structure 4 retain the carbonyl carbon of the arachidonyl precursor.

Both LGE$_2$ and 8-epi-LGE$_2$-PC (structure 2) produce the same product upon LG-pyrrole formation (i.e., upon formation of structure 4) because the stereocenter at position 8 is removed.

The immunoreactivity toward protein-LGE$_2$ adduct antibodies that is produced during free radical oxidation of LDLs provides evidence for the generation of structure 1, the endoperoxide, its rearrangement to structure 2, the levulinaldehyde derivative, and reaction of structure 2 with apo-B in oxLDL to produce structure 4, the LGE$_2$-derived pyrrole. (See FIG. 1) The immunoreactive structure 4 is believed to be only one of eight isomeric pyrroles present in oxLDL that are formed from a family of AA-derived levulinaldehydes. It is therefore believed that the free-radical pathway not only can produce levulinaldehydes with PG side-chains (i.e., "levuglandins" or "LGs"), but also levulinaldehyde derivatives with different side-chains that can be termed isoLevuglandins ("isoLGs") (See FIGS. 3A and 3B, structures 13a–f).

Figure 3A:
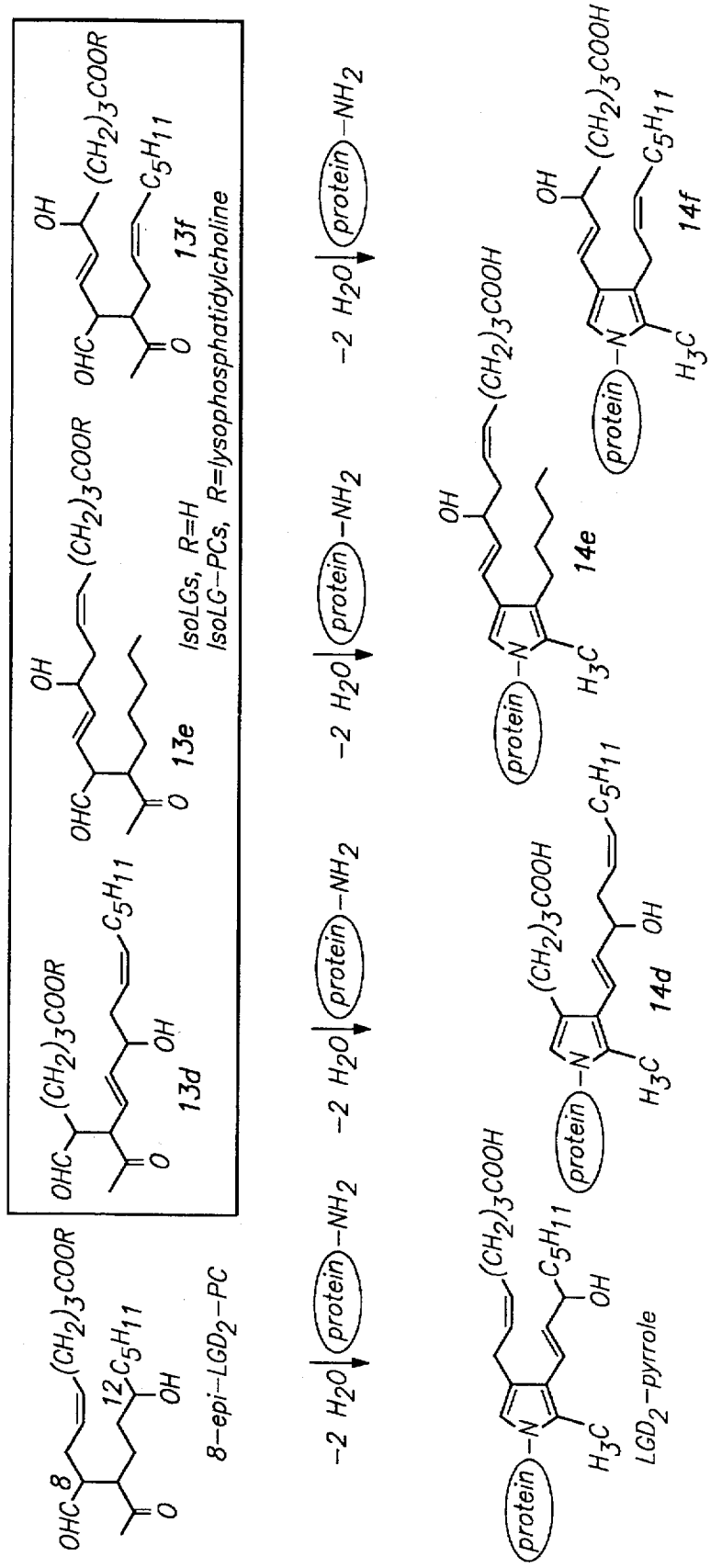
FIGS. 3A and 3B are schematics illustrating that the free-radical pathway can produce isolevuglandins in addition to levuglandins.
Figure 3B:
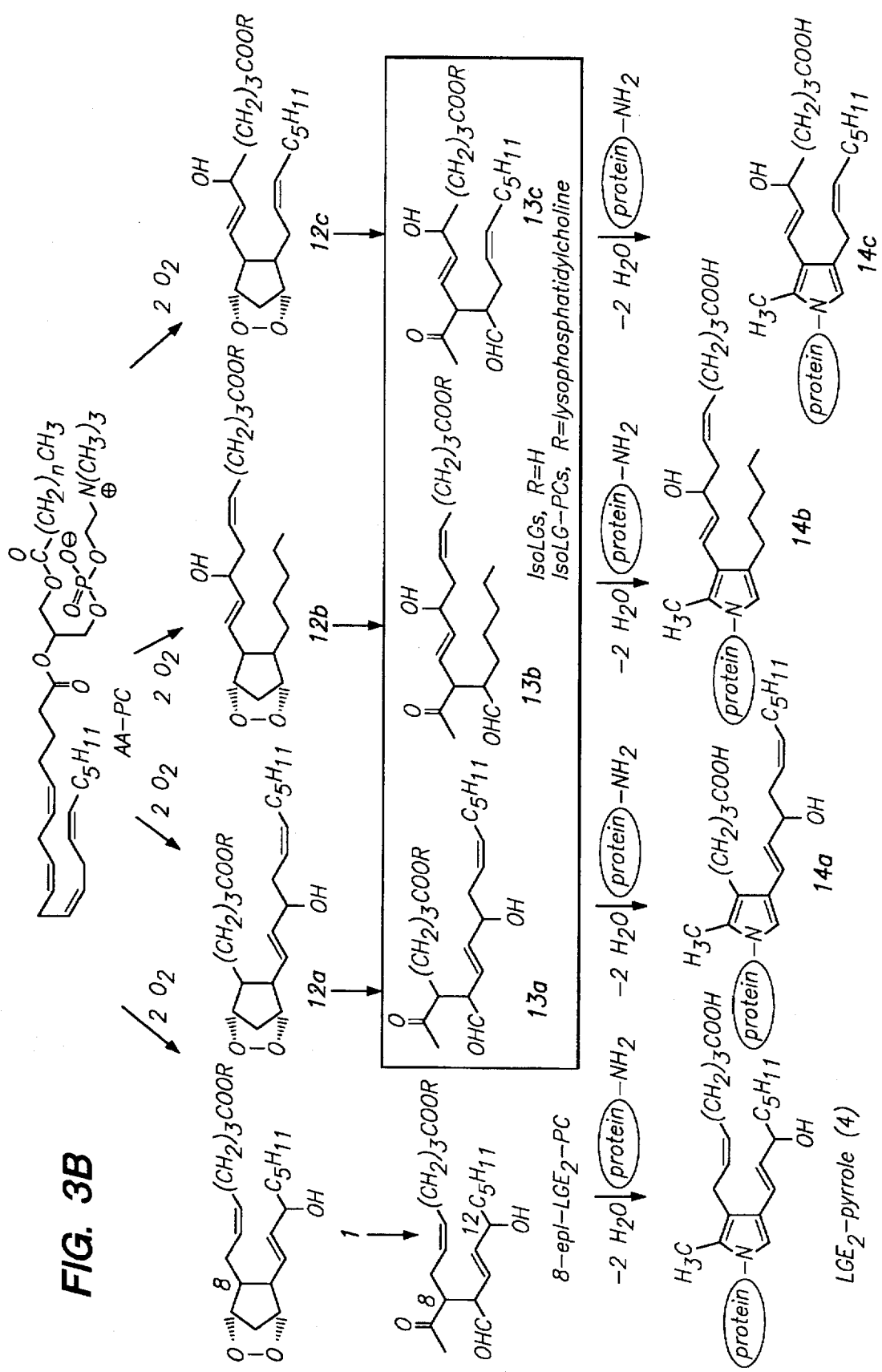

As will be discussed below, the formation of endoperoxides, structures 1 and 12a–c (see FIG. 3A) (where R=lysophosphatidylcholine), by a free-radical lipid peroxidative pathway explains the in vivo production of four isomeric PGF$_{2\alpha}$-like compounds that have been detected in human urine and blood. [J. D. Morrow et al., Proc. Natl. Acad. Sci. USA 87: 9383–87 (1990); J. D. Morrow et al., J. Biol. Chem. 269:1–11 (1994)]. It is likely that the rearrangements of the endoperoxides structures 12a–c will also generate the isoLGS structures 13a–f (see FIGS. 3A and 3B) because such rearrangements are a characteristic chemical reaction of the bicyclic peroxide ring system, and they occur readily in aqueous solution. [R. G. Salomon, Accounts Chem. Res. 18: 294 (1985)]. Finally, reaction of the levulinaldehyde moiety in the isoLG-phospholipids (structures 13a–f, where R=lysophosphatidylcholine) or the corresponding free acids (structures 13a–f, where R=H) with protein primary amino groups will produce the isoLG-derived protein-bound pyrroles in structures 14a–f (FIGS. 3A and 3B).

The present invention contemplates an immunoassay that provides a sensitive analytical method for detecting LG-derived pyrrole adducts (structure 4; see FIG. 1) in vivo. Moreover, the present invention sets forth evidence that a new family of oxidative lipid metabolites is generated by free-radical oxidation of LDL. Although direct detection is complicated because these reactive metabolites are rapidly sequestered by proteins, indirect detection as covalent adducts with proteins is feasible and supported by immunological evidence for the in vivo occurrence of such oxidatively modified proteins in human plasma.

III. LG-Protein Adducts as Immunogens and Preparation of Antibodies

A series of studies were performed involving the reaction of LGE$_2$ with proteins. In initial experiments, pyrroles generated from LGE$_2$ and simple amines readily decomposed to insoluble, presumably polymeric, products. However, an unexpected result of early studies involving the reaction of LGE$_2$ with KLH was that there was no detectable loss of immunoreactivity toward antibodies raised against LG-KLH pyrazole isostere over several weeks in a sample of KLH pyrrolyzed with LGE$_2$ (i.e., LGE$_2$-KLH). [E. DiFranco et al., Chem. Res. Toxicol. 8: 61–67 (1995)]. The paradoxical stability of protein-bound pyrrole may be the consequence of inhibition of pyrrole polymerization by the protein matrix. From a practical standpoint, this observation suggests that: (1) LG-protein adducts that are generated in vivo should accumulate, and (2) immunological detection of such oxidative protein modifications might be feasible with antibodies raised against LG-protein adducts. For that reason, antibodies were raised in rabbits against LGE$_2$-KLH (crude antibody serum was purified on a protein A column).

Characterization of protein modifications by immunological methods must recognize the possibility that structurally-nonspecific cross-reactivity might be responsible for binding inhibition observed in competitive inhibition studies. Therefore, to assess the structural specificity of the LGE$_2$-KLH antibodies, the ability of various compounds to competitively inhibit antibody binding to LGF$_2$-BSA was systematically examined (Table 2). Table 2 indicates the cross-reactivities of various PGs and LG-derived pyrroles.

TABLE 2

| | IC 50 (pmol/well) | % Cross-reactivity |
|---|---|---|
| R = HSA | 3.4 | 100 |
| 5a, R = t-Bu-CH$_2$— | 11.6 | 29 |
| 5b, R = HO(CH$_2$)$_6$— | 5.3 | 65 |

TABLE 2-continued

| | | IC 50 (pmol/well) | % Cross-reactivity |
|---|---|---|---|
| [structure] | 8-epi-PGF$_{2\alpha}$ | 457 | 0.74 |
| [structure] | PGB$_2$ | 1631 | 0.21 |
| [structure] | PGF$_{2\alpha}$ | 2356 | 0.14 |
| [structure] | AA | >10,000 | <0.01 |
| HSA, LDL, HNE-LDL, MDA-LDL [structures 6, 7, 8a, 8b] | | N.D. | 0.00 |

Referring to Table 2, the pyrrole structure 5b is closely related structurally to the protein-bound pyrrole that would be generated by Paal-Knorr condensation of LGE$_2$ with a protein lysyl residue. The immunoreactivity of structure 5b is 64% of that of an LGE$_2$-HSA standard (per mole of bound LG). This high cross-reactivity supports the conclusions that the reaction of LGF$_2$ with proteins can generate high yields of pyrrole derivatives (FIG. 1; structure 4) and that the LGE$_2$-KLH antibodies specifically recognize such pyrrole derivatives. To further define the molecular fragment required for antibody recognition, binding inhibition by the upper or lower side chain fragments (structures 6 and 7, respectively), the unoxidized fatty acid AA, as well as the HNE-derived pyrrole (structure 8a) and the sugar-derived pyrrole (structure 8b) were examined [See Table 1]. No significant cross-reactivity was detected. In contrast, molecules that incorporate both prostanoid side-chain fragments appended to vicinal carbons, i.e., 8-epi-PGF$_{2\alpha}$, PGB$_2$, and PGF$_{\alpha 2}$, do exhibit small but measurable cross-reactivity.

In prior studies, a pyrazole isostere antigen, structure 9 (see Table 1), was used to raise antibodies that recognize LGF$_2$-derived pyrroles. [E. DiFranco et al., Chem. Res. Toxicol. 8: 61–67 (1995)]. However, the present invention indicates that such pyrroles are recognized much more specifically by antibodies raised against LGE$_2$-KLH than by antibodies raised against the KLH-pyrazole isostere antigen (structure 9). This is evident from an ELISA comparison of the cross-reactivity of a prostaglandin relative to LG-derived pyrrole, structure 5b (see Table 1), toward the two different antibody preparations. With the antibodies raised against pyrazole isostere antigen (structure 9), the IC$_{50}$ for PGB$_2$ was only a factor of 7 greater than that for pyrrole structure 5b; in contrast, the difference is a factor of 305 with the LGE$_2$-KLH antibodies.

There are apparently rather stringent structural requirements for binding of the LGE$_2$-KLH antibodies with molecules that resemble portions of the LGE$_2$-derived region of LGE$_2$-protein adducts (structure 4; see FIG. 1). Nevertheless, there remained the possibility of nonspecific binding with proteins or with covalent protein adducts of other lipid oxidation products such as MDA or HNE. When examined, no cross-reactivity was detected for HSA, unoxidized LDL, or for MDA-LDL and HNE-LDL (See "Experimental" section, infra).

IV) Diagnostic Assays

A. Immunoassays For Detecting Antigens

Enzyme immunoassays for detecting antigens have been described. [A. Voller and D. Bidwell, in *Manual of Clinical Laboratory Immunology* (N. R. Rose et al., eds.; American Society For Microbiology, Washington D.C.) pp. 99–109 (3rd Ed. 1986)]. The "sandwich" or immunometric" method, which entails the use of excess labeled antibody, has been found to be particularly useful.

The basic sandwich method may be reduced to the following generic steps. First, specific antibody is bound to the solid phase. Second, the test sample that is to be assayed is incubated with the solid phase, then washed. Third, an enzyme-labeled specific-antibody conjugate is incubated with the solid phase, then washed to remove the unreacted conjugate. Fourth, the enzyme substrate solution is added, and the rate of the solution's degradation is proportional to the antigen concentration in the test sample. [A. Voller and D. Bidwell, in *Manual of Clinical Laboratory Immunology* (N. R. Rose et al., eds.; American Society For Microbiology, Washington D.C.) pp. 99–109 (3rd Ed. 1986)].

Several modifications to the basic sandwich method may be employed under particular circumstances. For example, the basic method can be modified to measure antibodies. In that situation, the second step involves testing a reference sample alone in one well; the reference sample is mixed with the test sample, believed to contain the antibody, in another well. Any antibody present will reduce the amount of antigen which is able to react with the solid phase; thus, less conjugate will be fixed and less substrate will be degraded. The antibody content in the test sample is proportional to the difference in substrate degradation between antigen by itself and antigen combined with test sample. [A. Voller and D. Bidwell, in *Manual of Clinical Laboratory Immunology* (N. R. Rose et al., eds.; American Society For Microbiology, Washington D.C.) pp. 99–109 (3rd Ed. 1986)].

Another modification of the basic sandwich method is used when the plate-coating antibody is from one species but the unlabeled antibody in the third step is from a different species. In that situation, a step is added following the third step in which an enzyme-labeled anti-species immunoglobulin is used. In this modification, only one antispecies reagent is needed. [A. Voller and D. Bidwell, in *Manual of Clinical Laboratory Immunology* (N. R. Rose et al., eds.; American Society For Microbiology, Washington D.C.) pp. 99–109 (3rd Ed. 1986)].

B. Detection of LG-LDL and LG-Lp(a) Adducts

As set forth above, oxidation of lipoproteins, predominantly LDL, has been linked to cardiovascular disease, and particularly to accelerated atherosclerosis leading to coronary artery disease (CAD). Previous studies have indicated that LDL in the circulation of specific patient populations is oxidized; however, the oxidized LDL had to be isolated by time-consuming separation techniques in order to be detected. In contrast, the present invention describes a much more efficient diagnostic assay for detecting oxidized LDL.

The present invention describes an ELISA procedure for measuring epitopes on proteins that are characteristic for oxidative events. Specifically, the ELISA procedure, a variation of the general method described above, uses a polyclonal antibody directed at an epitope (i.e., an antigenic determinant) formed when a highly reactive aldehydic-oxidation product of arachidonic acid, levuglandin, interacts with lysine side-chains on proteins. (See Example 1, infra.)

At low levels of oxidation (but not at high levels of oxidation), expression of this epitope correlated with the degree of oxidation of LDL. This is to be expected since extensively-oxidized LDL is removed in the liver via the scavenger receptor, but non-extensively oxidized LDL remains in the circulation. Indeed, the polyclonal antibody was found to be an excellent marker of oxLDL in the circulation when the degree of oxidation is low. What constitutes "extensive" and "non-extensive" oxidation is subject-specific, depending on factors like the amount of antioxidants and fatty acids present. As a rough approximation, however, extensive oxidation occurs after approximately 5–6 hours (See FIG. 4).

Other fractions of the lipid profile have also been linked to cardiovascular disease. The plasma lipoprotein fraction, Lp(a), has been shown to be an independent risk factor for accelerated atherosclerosis and thrombosis leading to CAD; Lp(a) is believed to exert its effect by disturbing the fibrinolytic system. The amount of Lp(a) is known to be elevated in certain disease states (e.g., end-stage renal disease). Moreover, Lp(a) is thought to be oxidized in certain disease states as well. Thus, oxidation of Lp(a) could further accelerate the atherosclerotic and thrombotic processes that culminate in CAD and other cardiovascular abnormalities. As a result, there is a need for the development of a quantitative approach to measuring the degree of oxidation of Lp(a) in plasma of individual patients. However, since the concentration of LDL in plasma greatly exceeds that of Lp(a), levels of LG-protein adducts would tend to better reflect levuglandin associated with LDL than that associated with Lp(a).

By immunoblotting agarose gels on which aliquots of plasma had been electrophoresed, qualitative data has been obtained on the distribution of the LG-protein adducts in different plasma protein or lipoprotein fractions such as LDL and Lp(a). The preliminary results indicated that the epitopes are primarily, though not exclusively, associated with lipoproteins. Sandwich assays are contemplated that permit quantification of the LG-protein adduct, and therefore quantification of oxidation in individual plasma fractions, especially the lipoprotein fraction. The assays entail the principle of specifically immuno-precipitating individual plasma proteins or lipoproteins; in so doing, an aliquot of plasma is applied to wells of plastic plates previously covered with excess amounts of antibody to the protein or lipoprotein of interest. Thereafter, the LG-protein antibody is applied as the detection antibody and quantitative data is obtained as described in detail in Example 1, infra.

EXPERIMENTAL

In the disclosure which follows, the following abbreviations apply: g (grams); mg (milligrams); μg (micrograms); ng (nanograms); μL (microliters); mL (milliliters); °C. (degrees Centigrade); μmol; (micromoles); mmol (millimoles); cm (centimeters); mm (millimeters); nm (nanometers); MW (molecular weight); mM (millimolar); $t_{1/2}$ (half-life); min (minutes); ppm. (parts per million); rpm (revolutions-per-minute); N (normal); ELISA (enzyme-linked immunosorbent assay); LDL (low density lipoprotein); oxLDL (oxidized low density lipoprotein); Lp(a) (lipoprotein (a)); apo (apolipoprotein); MDA (malondialdehyde); HNE (4-hydroxynonenal); LG (levuglandin); $PLA_2$ (phospholipase $A_2$); AA (arachidonic acid); PC (2-lysophosphatidylcholine); UV (ultraviolet); MHz. (Megahertz); TLC (thin layer chromatography); FPLC (fast protein liquid chromatography); HPLC (high pressure liquid chromatography); NMR (nuclear magnetic resonance); LSC (liquid scintillation counting); $^1$H-NMR (proton nuclear magnetic resonance); MeOH (methanol, methyl alcohol); THF (Tetrahydrofuran); LiAlH$_4$ (lithium aluminum hydride); CDCl$_3$ (deuterated chloroform, chloroform-d); BSA (bovine serum albumin); HSA (human serum albumin), KLH (keyhole limpet hemocyanin); CHCl$_3$ (chloroform); PBS (phosphate buffered saline); TBS (Tris buffered saline); Ci (curies); mCi (millicuries); μCi (microcuries); nCi (nanocuries); dpm (disintegrations-per-minute); R$_f$ (movement of a substance in chromatography relative to the solvent front); Hg (mercury); DCC (1,3-dicyclohexylcarbodiimide); DMAP (dimethylaminopyridine), N$_2$ (nitrogen, elemental state); AcOH-water (acetic acid-water solution); NaI (sodium iodide); NaH (sodium hydride); PBr$_3$ (phosphorus tribromide); NaIO$_4$ (sodium periodate); BHT (butylated hydroxytoluene); NaCl (sodium chloride); CuSO$_4$ (copper (II) sulfate); EDTA (ethylene-diaminetetraacetic acid); Na$_2$EDTA (disodium salt of ethylene-diaminetetraacetate); NaN$_3$ (sodium azide); OA (ovalbumin); CEO (chicken egg ovalbumin); MgCl$_2$ (magnesium chloride); NaOH (sodium hydroxide); HCl (hydrochloric acid); NaCNBH$_3$ (sodium cyanoborohydride); CH$_2$Cl$_2$ (dichloromethane); IC$_{50}$ (inhibitor concentration at the 50% absorbance value); AS (atherosclerosis); RF (renal failure); CABG (coronary artery bypass graft); CAPD (continuous ambulatory peritoneal dialysis); min. (minutes); h (hours); v/v and v:v (volume-to-volume); w/w and w:w (weight-to-weight); T×100 (Triton×100); DMSO (dimethyl sulfoxide); H$_2$O (water); Baxter (Baxter Diagnostics Inc., Bellevue, Wash.); Beckman (Beckman Instruments, San Ramon, Calif.); Bio-Rad (Bio-Rad Laboratories, Hercules, Calif.); Boehringer-Mannheim (Boehringer-Mannheim Corp., Indianapolis, Ind.); Calbiochem (Calbiochem-Novabiochem Corp., La Jolla, Calif.); Dynatech Labs (Chantilly, Va.); Fisher (Fisher Scientific Co., Pittsburg, Pa.); ICN (ICN Biomedicals, Inc., Costa Mesa, Calif.); E. Merck (Darmstadt, West Germany); Jandel Scientific Software (San Rafael, Calif.); Pharmacia (Pharmacia Biotech Inc., Piscataway, N.J.); Sigma (Sigma Chemical Company, St. Louis, Mo.); Sorvall (subsidiary of DuPont, Co., Newtown, Conn.).

The description of experimental information that follows is divided into the following parts: I) General Methods and Materials; II) Preparation of Reactants and Other Compounds; and III) Examples. The experimental information and examples serve to illustrate certain preferred embodiments and aspects of the present invention and should not to be construed as limiting the scope thereof.

I. General Methods and Materials

Methods $^1$H NMR spectra were recorded at 300 MHz, and proton chemical shifts are reported in parts per million on the δ scale relative to tetramethylsilane (δ0.00). Tetramethylsilane or chloroform (δ7.24) were used as internal standard. Significant $^1$H NMR spectral data are tabulated in the following order: multiplicity (s, singlet; d, doublet; t, triplet; q, quartet; m, multiplet; br, broad), number of protons, coupling constant(s) in hertz. Liquid scintillation counting (LSC) was done on a Beckman LS 5801 counter with quench curves made from a Beckman $^3$H standard set.

Samples were prepared with 5 mL of xylene-based scintillation fluid (Fisher). Centrifugation was done on a Sorvall centrifuge at 5° C. and 2000 rpm unless otherwise noted. Absorbance values of ELISAs were measured on a Bio-Rad Microplate Reader using dual wavelength (405 nm to read the plate and 650 nm as a reference). For all ELISAs, unless otherwise noted, duplicates of each sample were run on the same plate. Thin layer chromatography (TLC) was performed on glass plates pre-coated with silica gel (Kieselgel 60 F$_{254}$, E. Merck, Darmstadt, West Germany), R$_f$ values are quoted for plates of thickness 0.25 mm. Visualization was done by viewing the developed plates under short-wavelength UV light and by heating the plates after spraying with vanillin-sulfuric acid. Flash column chromatography was performed on 230–400 mesh silica gel supplied by E. Merck.

Materials

SPECTRA/POR® No. 2 membrane tubing (MW cutoff 14,000) for standard dialysis was obtained from Fisher Scientific Co. All solvents were reagent grade or purer. Tetrahydrofuran (THF) was boiled under reflux over potassium benzophenone ketal and distilled. Diethyl ether was boiled under reflux over LiAlH$_4$ and distilled. Ethyl acetate, hexane, and diethyl ether used for extractions or chromatography were distilled to remove non-volatile impurities prior to use. The following commercially available materials were used as received: chicken egg ovalbumin (OA, grade V, 99%), bovine serum albumin (BSA, fraction V, 96–99%), human serum albumin (HSA, fraction V), disodium p-nitrophenyl phosphate, arachidonic acid, PGF$_{2\alpha}$, and PGB$_2$ were from Sigma (St. Louis, Mo.); keyhole limpet hemocyanin (KLH, ICN Biomedicals); goat anti-rabbit alkaline phosphatase (Boehringer-Mannheim). Phosphate buffered saline (PBS) was prepared from a pH 7.4 stock solution containing 0.2M NaH$_2$PO$_4$/Na$_2$HPO$_4$, 3.0M NaCl, and 0.02% NaN$_3$ (w/w). This solution was diluted 20× as needed. Tris buffered saline (TBS) was prepared from 5 mM trizma (Sigma), 1 mM NaCl and 0.6 mM CaCl$_2$.

II) Preparation of Reactants and Other Compounds

LGE$_2$ [8(R)-acetyl-9(R)-formyl-12(S)-hydroxyl-5(Z),10 (E)-heptadecadienoic acid] and 2-[8-acetyl-12-t-butyldimethylsiloxy-9-(1(S),2-isopropylidenedioxyethyl)-5 (Z),10(E)-heptadecadienoic acid (Structure 10; see Table 1)

As previously indicated, LGE$_2$ may be obtained from PGH$_2$, an unstable intermediate in the oxidative transformation of arachidonic acid into numerous biologically-active derivatives. LGE$_2$ is produced by an intramolecular hydride migration from the 9- to the 10-position in PGH$_2$, and cleavage of the 10, 11 C—C and the peroxide O—O bonds.

LGE$_2$ may also be prepared according to the method described in D. B. Miller et al., "Levuglandin E$_2$: Enantio-controlled Total Synthesis of a Biologically Active Rearrangement Product from the Prostaglandin Endoperoxide PGH$_2$," J. Org. Chem. 55: 3164–75 (1990), who report a total synthetic procedure that eliminates the need to begin with the limited-available PGH$_2$; this method was used in the present invention and is depicted schematically in FIG. 5A.

Figure 5B:
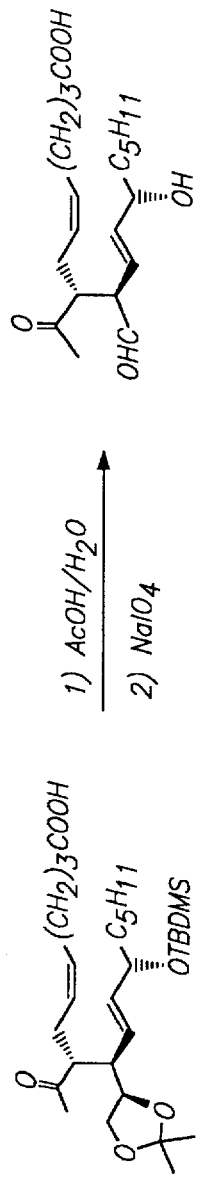
FIG. 5B is a schematic depicting the formation of LGE$_2$ by concomitant hydrolysis and oxidative cleavage of an LGE$_2$ precursor (8(R)-acetyl-9(R)-[1(R),2-(isopropylidenedioxy)ethyl]-12(S)-(tert-butyldimethyslsiloxy)-5(Z),10(E)-heptadecadienoic acid; structure 26RR).
Figure 5A:
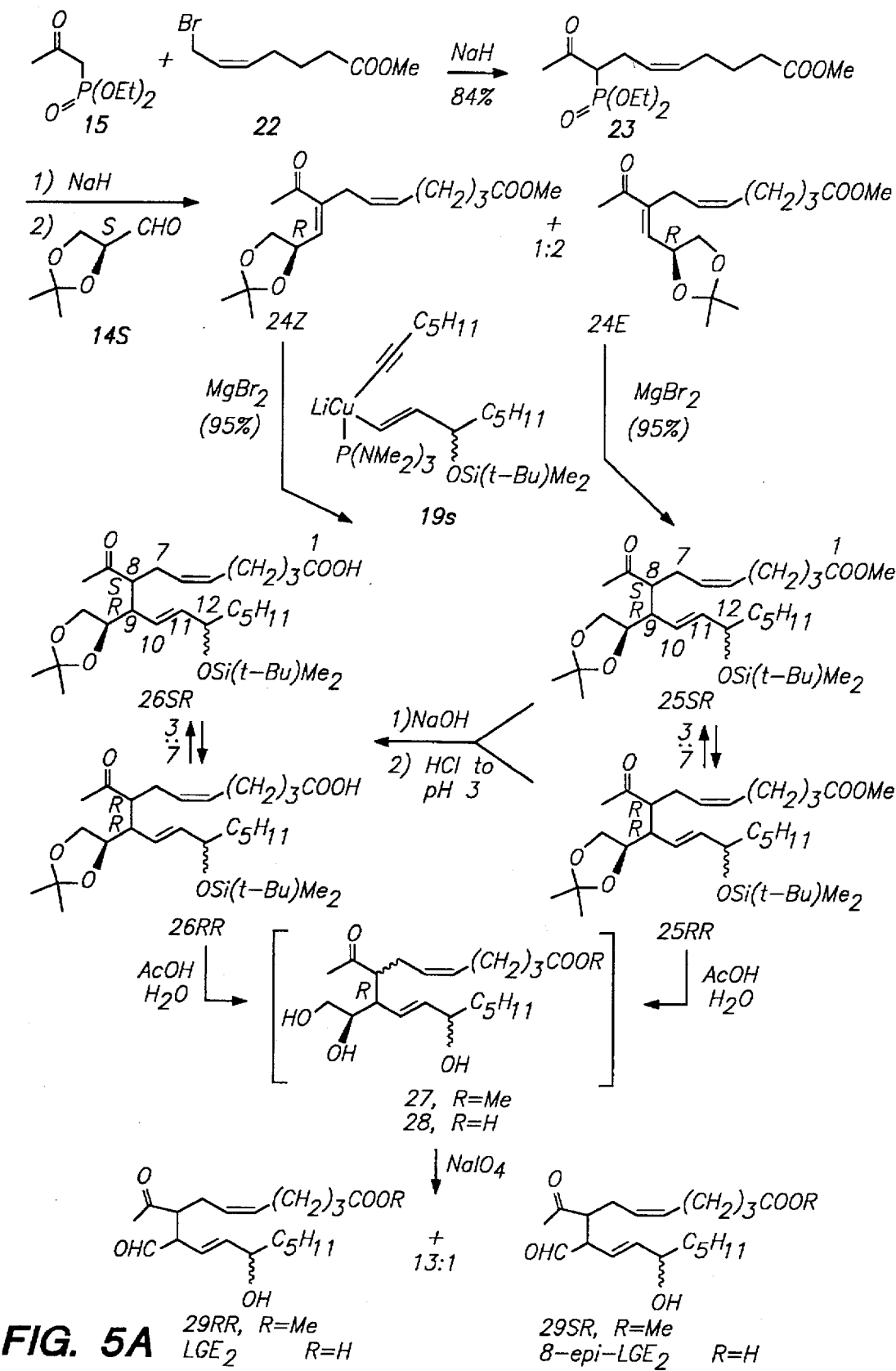
FIG. 5A is a schematic of the synthetic pathway of LGE$_2$.

Isopropylidene-L-glyceraldehyde (structure 14S; see FIG. 5A). The procedure of Baker [J. Am. Chem. Soc. 74: 827 (1952) was modified. Thus, 4,5-isopropylidene-L-arabinose dibenzyl thioacetal (12.14 g, 28.9 mmol) was dissolved in anhydrous benzene (300 mL). While stirring vigorously, finely powdered lead tetraacetate (12.8 g, 28.9 mmol) was added in one portion at room temperature. Stirring was continued for 1.5 h and then stopped to allow the free white crystals of lead diacetate to settle. The benzene solution was filtered, and the filtrate was transferred to a distillation flask. The benzene was distilled under reduced pressure through an efficient fractionating column at 28° C. (110 mm). When only 20 mL of liquid remained in the flask, the distillation was stopped, the contents of the flask were transferred to a smaller distillation flask, and n-heptane (20 mL) was added. The n-heptane/acetic acid azeotrope was distilled at 18° C. (40 mm). After adding and distilling 3×20-mL portions of n-heptane from the flask, the product was fractionally distilled at 36° C. (9 mm) to furnish 1.57 g of structure 14S as a clear oil, 90% pure by $^1$H NMR spectroscopy and essentially free of acetic acid. Its $^1$H NMR spectrum agreed with that reported for the D-glyceraldehyde enantiomer.

Methyl 8-(Diethylphosphono)-9-oxodec-5(Z)-enoate (structure 23; see FIG. 5A). As depicted in FIG. 5A, to a magnetically stirred suspension of sodium hydride (853 mg, 35.5 mmol, 1.2 equiv) in anhydrous THF (50 mL) was added (diethylphosphono)acetate (structure 15) (5.75 g, 29.6 mmol) at room temperature. Stirring was continued for 2 h, and then methyl 7-bromohept-5(Z)-enoate (structure 22) (6.18 g, 28.1 mmol) was added in the dark at room temperature. The reaction mixture was stirred in the dark for 12 h. The solvent was then removed by rotary evaporation, and water (40 mL) was added to the resulting dark yellow residue. The aqueous mixture was extracted with ethyl acetate (5×50 mL), and the combined ethyl acetate extracts were washed once with brine (40 mL), dried (MgSO$_4$), filtered, and concentrated under reduced pressure to furnish 9.02 g of a clear oil. This oil was flash chromatographed on a 13-cm column packed with a 15-cm bed of silica gel employing ethyl acetate/hexane (3:1, v/v) as the mobile phase. The pooled product fractions were concentrated under reduced pressure, and the product was further purified by preparative HPLC on a Whatman M20 column (20 mm i.d.×50 cm), employing a mobile phase of ethyl acetate/ hexane (2:1 v/v) at a flow rate of 14 mL/min to remove a dialkylation product which was slightly less polar. The yield of structure 23, homogeneous by TLC (R$_f$ 0.3, 100% ethyl acetate, was 7.93 g (84% based on allylic bromide 22): $^1$H NMR δ 5.42–5.16 (2 H, C-4, C-5 H's), 4.07 (apparent quintet, 4 H, J=8.3 Hz, OCH$_2$CH$_3$), 3.61 (s, 3 H, OCH$_3$), 3.11 (ddd, H, J=23.8, 10.6, 3.8 Hz, C-8 H), 2.82–2.58 (br m, H, C-7 H$_a$), 2.54–2.34 (br m, H, C-7 H$_b$), 2.25 (t, 2 H, J=7.6 Hz, C-2 H), 2.23 (s, 3 H, C-10 H), 2.05 (apparent q, 2 H, J=6.8 Hz, C-4 H), 1.62 (apparent quintet, 2 H, J=7.2 Hz, C-3 H), 1.27 (t, 6 H, J=7.3 Hz, OCH$_2$CH$_3$); $^{13}$C NMR δ 203.05 and 202.97 (C-9, +), 173.76 (C-1, +), 131.15 (C-5, –), 126.73 and 126.43 (C-6, –), 62.68 and 62.54 and 62.47 and 62.33 (2 OCH$_2$CH$_3$'s, +), 53.31 (d, J=124.2 Hz, C-8 split by $^{31}$P, –), 51.33 (OCH$_3$, –), 33.25 (C-2, +), 31.36 (C-10, –), 26.38 (C-3, +), 24.47 (C-4, +), 24.22 and 24.13 (C-7, +), 16.28 and 16.16 (OCH$_2$CH$_3$, –). Anal. Calcd for C$_{15}$H$_{27}$O$_6$P: C, 53.88; H, 8.14; P, 9.26. Found: C, 52.70; H, 8.05; P, 9.48.

Methyl 8-Acetyl-10(R), 11-(isopropylidenedioxy)-5(Z), 8-undecadienoates [(10R)-structure 24]. Referring to FIG. 5A, a magnetically stirred suspension of sodium hydride (302 mg, 12.58 mmol, 1.25 equiv) in anhydrous THF (20 mL) was cooled to –5° C. The β-keto phosphonate (structure 23) (3.38 g, 10.11 mmol) in anhydrous tetrahydrofuran (20 mL) was added via a dropping funnel over 10 min. Stirring was continued at this temperature for 4 h. Then isopropylidene-L-glyceraldehyde (structure 14S) (1.67 g, 11.12 mmol, 1.1 equiv, 88% purity) in anhydrous THF (5 mL) was added over 5 min. The solution was allowed to warm at room temperature and stirring was continued for 12 h. The solvent was then removed by rotary evaporation, and water (50 mL) was added to the resulting brown oily residue. The aqueous mixture was extracted with diethyl ether (5×50 mL), and the combined organic extracts were washed once with water (20 mL), dried (MgSO$_4$), and filtered, and the solvent was removed under reduced pressure to afford 2.93 g of a clear yellow oil. This oil was flash chromatographed in three runs, each of approximately 1 g, on a 5-cm column packed with a 15-cm bed of silica gel. The column was eluted with ethyl acetate/hexane (1:3, v/v). Thirty 50-mL fractions were collected from each run. The mixed structure 24Z and structure 24E isomers eluted in fractions 13–22 and gave 2.32 g, from the three runs combined, of a clear oil (75% based on β-keto phosphonate 23). The structure 24Z and structure 24E isomers (1:2.3, respectively) need not be separated for the next reaction; however, these geometrical isomers were separated for thorough characterization using the "shave-recycle" HPLC technique. Thus, a solution containing 150 mg of the mixture of structure 24Z and structure 24E in 0.6 mL of ethyl acetate/hexane (1:3, v/v) was injected onto a Whatman M9 column (9.4 mm i.d.×50 cm) and eluted with this same solvent mixture at a flow of 2.2 mL/min. The eluate was monitored by UV absorption at 274 nm and, after removal of a forerun, was recycled through the column five times. Separate fractions were collected from the late-eluting portion of the product peaks (first through fifth passes) and from the early eluting portion of the product peaks (third through fifth passes). Complete chromatographic resolution of the geometrical isomers was achieved after the fifth passage through the column. This afforded, after complete removal of solvents under reduced pressure, 45 mg of the less polar methyl 8-acetyl-10 (R), 11-(isopropylidenedioxy)- 5(Z), 8(Z)-undecadienoate (structure 24Z): $^1$H NMR δ 5.72 (dt, H, J=7.2, 1.3 Hz, C-9 H), 5.59–5.41 (m, H, C-5 H), 5.40–5.22 (m, H, C-6 H) 4.84 (apparent q, H, J=6.9 Hz, C-10 H), 4.25 (dd, H, J=6.7, 8.2 Hz, C-11 H), 3.62 (s, 3 H, OCH$_3$), 3.50 (dd, H, J=7.2, 8.2 Hz, C-11 H), 2.99 (br d, 2 H, J=6.8 Hz, C-7 H), 2.28 (t, 2 H, J=7.4 Hz, C-2 H), 2.21 (s, 3 H, acetyl methyl), 2.05 (apparent q, 2 H, J=7.2 Hz, C-4 H), 1.66 (apparent quintet, 2 H, J=7.2 Hz, C-3 H), 1.38 (s, 3 H, isopropylidene methyl), 1.3 1 (s, 3 H, isopropylidene methyl); $^{13}$C NMR δ 201.9 (acetyl carbonyl, +), 173.8 (C-1, +), 140.8 (C-8, +), 137.2 (–), 131.6 (–), 126.1 (–), 109.4 (isopropylidene ketal carbon, +), 73.9 (C-10, –), 69.7 (C-11, +), 51.5 (OCH$_3$, –), 33.3 (+), 31.4 (+), 29.1 (acetyl methyl, –), 26.5 (2 C, coincident resonances, isopropylidene methyl and C-4, + and –), 25.4 (isopropylidene methyl, –), 24.5 (C-3, +); [α]$^{25}_D$–114.9° (c 0.166, CHCl$_3$): ORD (c 7.3×10$^{-2}$, n-heptane), at 25° C. [α]$_{600}$–164°, [α]$_{589}$–172°, [α]$_{361}$–726° (broad peak), [α]$_{298}$+218°, [α]$_{270}$+109°, [α]$_{255}$+355°; high resolution mass spectrum, m/e calculated for C$_{17}$H$_{26}$O$_5$ 310.1780, found m/e (rel intensity) 310.1740 (0.2), 252 (g), 235 (22), 222 (10), 121 (13), 43 (100). There was also obtained 105 mg of the more polar methyl 8-acetyl-10-(R), 11-(isopropylidenedioxy)-5(Z),8(E)-undecadienoate (24E): $^1$H NMR δ 6.49 (d, H, J=8.0 Hz, C-9 H), 5.41–5.21 (m, H, C-5 H), 5.19–5.01 (m, H, C-6 H), 4.89 (apparent q, H, J=6.4 Hz, C-10 H), 4.16 (dd, H, J=8.2, 6.4 Hz, C-11 H), 3.64 (s, 3 H, OCH$_3$), 3.61 (dd, H, J=8.2, 6.4 Hz), 3.08 (dd, H, J=6.6, 14.9 Hz, C-7 H$_a$), 2.97 (dd, H, J=6.7, 14.7 Hz, C-7 H$_b$), 2.31 (t, 2 H, J=7.5 Hz, C-2 H), 2.30 (s, 3 H, acetyl methyl), 2.14 (apparent q, 2 H, J=6.9 Hz, C-4 H), 1.69 (apparent quintet, 2 H, J=7.3 Hz, C-3 H), 1.44 (s, 3 H, isopropylidene methyl), 1.38 (s, 3 H, isopropylidene methyl); $^{13}$C NMR δ 198.4 (acetyl carbonyl, +), 173.8 (C-1, +), 142.5 (C-8, +) 139.8 (–), 129.6 (–), 127.4 (–), 109.8 (isopropylidene ketal carbon, +), 72.7 (C-10, –), 68.8 (C-11, +), 51.3 (OCH$_3$, –), 33.3 (C-7, +), 26.5 (2 C, coincident resonances, + and –) 25.6 (–), 25.5 (–), 24.5 (+); 24.1 (+); [α]$^{25}_D$–23.5° (c 0.43, CHCl$_3$); ORD (2.6×10$^{-2}$ n-heptane), at 25° C., [α]$_{600}$–27°, [α]$_{589}$–27°, [α]$_{396}$–58°, [α]$_{377}$–41°, [α]$_{368}$–51°, [α]$_{361}$–44°, [α]$_{348-343}$–97° (shoulder), [α]$_{335}$–155°, [α]$_{330}$–145°, [α]$_{324}$–167°,

[α]₃₁₆ –142° (shoulder), [α]₂₇₅+204°; high-resolution mass spectrum, m/e calculated for $C_{17}H_{26}O_5$ 310.1780, found m/e (rel intensity) 310.1793 (6.7), 293 (16), 253 (63), 252 (29), 235 (75), 222 (57), 121 (27), 43 (100).

Methyl 8-Acetyl-9 (R)-[1(R), 2-(isopropylidenedioxy)-ethyl]-12(S)-(tert-butyldimethylsiloxy)-5(Z),10(E)-heptadecadienoates [(9R)-structure 25]. Referring to FIG. 5A, the mixed cuprate structure 19S from 1-iodo-3(S)-(tert-butyldimethylsiloxy)-1(E)-octene (2.2 g, 5.74 mmol, 1.15 equiv) was prepared by the method of Corey and Beames. [J. Am. Chem. Soc. 94: 7827 (1972)]. To this was added anhydrous magnesium dibromide as a 0.2M solution in THF (28.6 mL, 5.7 mmol, 1.15 equiv) dropwise over 15 min at –78° C. Upon completing the addition, a mixture of C-8(Z), C-10(R) and C-8(E),C-10(R) enones (structure 24) (1.55 g, 5.00 mmol, 1 equiv) was added dropwise as a 1.5M solution in anhydrous diethyl ether. The temperature was kept at –78° C. for 1 h, and then the reaction mixture was allowed to slowly warm to 0° C. over 1 h and quenched by addition of saturated aqueous ammonium chloride (5 mL). The reaction mixture was diluted with water (50 mL), and the aqueous layer was extracted with diethyl ether (3×75 mL). The combined ether extracts were washed with ice-cold 2% aqueous sulfuric acid (4×15 mL). The aqueous washes were re-extracted with ether (2×50 mL). The combined ether extracts were filtered, and the filtrate was washed with saturated aqueous sodium bicarbonate (20 mL). The extract was dried (MgSO₄), filtered, and concentrated under reduced pressure to afford 3.08 g of a clear yellow oil. This oil was flash chromatographed on an 8-cm i.d. column packed with a 15-cm bed of silica gel. The column was eluted with ethyl acetate/hexane (1:4, v/v), and 40 50-mL fractions were collected. Fractions 11–20 contained the C-8(S) and C-8 (R) 1, 4-addition products (structure 25) (2.12 g). Fractions 21–25 contained the C-8(R) epimer structure 25RR, along with a more polar byproduct in a 60/40 ration (192 mg). Fractions 31–40 contained recovered starting enones structures 24Z and 24E (187 mg). Thus, the overall yield for this conjugate addition was 92% based on enones 24 consumed with an 88% conversion.

The C-8(S) and C-8(R) epimers of structure 25 were separated by HPLC on a WHATMAN PARTISIL® Magnum 20 preparative LC column (20 mm i.d.×50 cm) employing a mobile phase of tert-butyl methyl ether/ethyl acetate/heptane (10/7/83, v/v/v) at a flow of 14 mL/min. Under these conditions, the retention times for the C-8(S) and C-8(R) epimers were 39 min and 43 min, respectively. After HPLC, there was obtained 567 mg of the minor C-8(S) epimer structure 25SR and 1.374g of the major C-8(R) epimer structure 25RR. Thus, the combined overall isolated yield and pure epimers of (9R)-structure 25 was 80%.

Methyl 8(S)-acetyl-9(R)-[1(R),2-(isopropylidenedioxy)-ethyl]-12(S)-(tert-butyldimethylsiloxy)-5(Z),10(E)-heptadecadienoate (structure 25SR), see FIG. 5A): $R_f$=0.50, 50% ethyl acetate/heptane (v/v); $^1H$ NMR δ 5.48–5.36 (2 H, C-10, C-11 H's), 5.41–5.18 (2 H, C-5, C-6 H's), 4.07–3.94 (m, H, C-12 H), 3.94–3.80 (2 H), 3.63 (s, 3 H, OCH₃), 3.57–3.46 (m, H), 3.07–2.97 (m, H, C-8 H), 2.38–2.18 (2 H, C-9 H, C-7 Ha), 2.26 (t, 2 H, J=7.8 Hz, C-2 H), 2.16 (s, 3 H, acetyl methyl), 2.07–1.90 (3 H, C-4 H, C-7 H$_b$), 1.64 (apparent quintet, 2 H, J=7.3 Hz, C-3 H), 1.46–1.28 (2 H, C-13 H), 1.38 (s, 3 H, isopropylidene methyl), 1.30 (s, 3 H, isopropylidene methyl), 1.23 (br s, 6 H, C-14, C-15, C-16 H's), 0.85 (s, 9 H, tert-butyl silyl), 0.84 (t, 3 H, J=5.9 Hz, C-17 H), 0.00 (s, 6 H, dimethyl silyl); $^{13}C$ NMR δ 211.95 (+), 173.97 (C-1, +), 138.62 (–), 130.63 (–), 127.59 (–), 125.09 (–), 109.37 (+), 76.13 (–), 73.05 (C-12,–), 69.11 (+), 52.13 (C-8, –), 51.48 (OCH₃, –), 49.96 (C-9, –), 38.46 (+), 33.46 (+), 32.45 (–), 31.81 (+), 28.22 (+), 26.95 (–), 26.67 (+), 25.83 (3 C, tert-butyl methyls, –) 25.58 (–), 24.84 (+), 24.72 (+), 22.64 (+), 18.21 (+), 14.03 (C-17, –), –4.44 (–), –4.85 (–); high-resolution mass spectra (8 eV), m/e calculated for (M-15) 537.3611, found m/e (rel intensity) 537.3593 (6.3), 495 (100), 437 (21), 421 (17), 345 (12), 255 (29), 101 (23).

Methyl 8(R)-acetyl-9(R)-[1(R), 2-(isopropylidenedioxy)-ethyl]-12(S)-(tert-butyldimethylsiloxy)-5(Z),10(E)-heptadecadienoate (structure 25RR; see FIG. 5A): $R_f$=0.48, 50% ethyl acetate/heptane (v/v); $^1H$ NMR δ 5.49 (dd, H, J=15.4, 5.9 Hz, C-11 H), 5.40–5.15 (2 H, C-5, C-6 H's), 5.18 (ddd, H, J=15.5, 8.8, 0.9 Hz, C-10 H), 4.02 (apparent q, H, J=6.7 Hz, C-12 H), 3.99–3.86 (2 H), 3.63 (s, 3 H, OCH₃), 3.64–3.49 (m, H), 2.77–2.62 (m, H, C-8 H), 2.58–2.39 (m, H, C-9 H), 2.29–2.02 (2 H, C-7 H), 2.27 (t, 2 H, J=7.8 Hz, C-2 H), 2.10 (s, 3 H, acetyl methyl), 2.01 (apparent q, 2 H, J=7.8 Hz, C-4 H), 1.63 (apparent quintet, 2 H, J=7.3 Hz, C-3 H), 1.48–1.28 (2 H, C-13 H), 1.33 (s, 3 H, isopropylidene methyl), 1.29 (s, 3 H, isopropylidene methyl), 1.23 (br s, 6 H, C-14, C-15, C-16 H's), 0.85 (s, 9 H, tert-butylsilyl), 0.84 (t, 3 H, J=6.1 Hz, C-17 H), 0.00 (s, 3 H, methyl silyl), –0.02 (s, 3 H, methylsilyl); $^{13}C$ NMR δ 210.61 (+), 174.01 (C-1, +), 138.59 (C-11, –), 130.44 (–), 127.61 (–), 125.04 (–), 109.57 (+), 77.17 (–), 72.76 (C-12, –), 68.79 (+), 54.43 (C-8, –), 51.44 (OCH₃ –), 49.58 (C-9, –), 38.31 (+), 33.50 (+), 31.78 (+), 30.80 (–), 26.66 (+), 26.51 (+), 26.42 (–), 25.80 (3 C, tert-butyl methyls, –), 25.58 (–), 24.73 (+), 24.70 (+), 22.60 (+), 18.20 (+), 14.01 (C-17, –), –4.45 (–), –4.78 (–); high-resolution mass spectrum (8 eV), m/e calculated for $C_{31}H_{56}O_6Si$: 552.3846, found m/e (rel intensity) 552.3766 (1), 537 (6), 495 (79), 432 (23), 421 (28), 395 (54), 345 (20), 337 (26), 255 (49), 101 (100).

8-Acetyl-9(R)-[1(R),2-(isopropylidenedioxy) ethyl]-12-(S)-(tert-butyldimethylsiloxy)-5(Z),10(E)-heptadecadienoic Acids (epimeric structures 26 SR and 26 RR [see FIG. 5A] which correspond to the non-stereospecific structure 10) [see Table 1]. Referring to FIG. 5A, a 7:3 mixture of the epimeric esters structures 25RR and 25SR (100 mg, 0.181 mmol) was stirred with 4.5 mL of water/methanol/tetrahydrofuran (2:5:3, v/v/v) containing sodium hydroxide (36 mg, 0.904 mmol, 5 equiv) at room temperature. After 1.5 h, the reaction mixture was acidified to pH 3 with 2N HCl and the aqueous layer was extracted with ethyl acetate (3×15 mL). The combined organic extracts were washed once with water (10 mL), and this aqueous wash was re-extracted once with ethyl acetate (15 mL). The organic extracts were combined, dried (MgSO₄), filtered, and concentrated under reduced pressure to afford 96 mg (98% yield) of the epimeric carboxylic acids. The C-8(R) and C-8(S) epimers were separated by preparative HPLC on a WHATMAN PARTISIL® Magnum 9 column (9.4 i.d.×50 cm), employing acetic acid/ethyl acetate/n-heptane (2/20/78, v/v/v) as the mobile phase at a flow of 2.0 mL/min. Under these conditions, the retention times for the epimeric products structures 26SR and 26RR were 23 and 27 min, respectively. HPLC purification afforded 28 mg (29%) of 8(S)-acetyl-9(R)-[1(R),2-(isopropylidenedioxy)ethyl]-12(S)-(tert-butyldimethylsiloxy)-5(Z),10(E)-heptadecadienoic acid (structure 26SR): $^1H$ NMR δ 5.47–5.39 (2 H, C-10, C-11 H's), 5.38–5.22 (2 H, C-5, C-6 H's), 4.08–3.97 (m, H, C-12 H), 3.96–3.83 (2H), 3.59–3.46 (m, H), 3.10–2.96 (m, H, C-8 H), 2.41–2.19 (2H, C-9 H, C-7 1–13, 2.31 (t, 2 H, J=7.8 Hz, C-2 H), 2.16 (s, 3 H, acetyl methyl), 2.11–1.92 (3 H, C-4 H, C-7 H$_b$), 1.65 (apparent quintet, 2 H, J=7.3 Hz, C-3 H), 1.53–1.38 (2 H, C-13 H), 1.39 (s, 3 H, isopropylidene methyl), 1.31 (s, 3 H, isopropylidene methyl), 1.24 (br s, 6 H, C-14, C-15, C-16 H's), 0.86 (s, 9 H, tert-butylsilyl), 0.85 (t, 3 H, or=5.6 Hz, C-17 H), 0.01 (s, 6 H, dimethylsilyl); $^{13}$C NMR δ 210.78 (+), 173.92 (C-1 +), 138.59 (C-11, −), 130.46 (−), 127.73 (−), 125.05 (−), 109.39 (isopropylidene ketal carbon, +), 76.11 (−), 73.05 (C-12,−), 69.09 (+), 52.11 (C-8,−), 49.96 (C-9,−), 38.41 (+), 33.35 (+), 32.45 (+), 31.29 (−), 28.21 (+), 26.92 (−), 26.54 (+), 25.82 (3 C, tert-butyl methyls, −), 25.56 (−), 24.83 (+), 24.42 (+), 22.62 (+), 18.21 (+), 14.01 (C-17, −), −4.47 (−), −4.86 (−). There was also obtained 67 mg (70%) of 8(R)-acetyl-9(R)-[1(R),2-(isopropylidenedioxy) ethyl]-12(S)-(tert-butyldimethylsilyloxy)-5(Z),10(E)-heptadecadienoic acid (structure 26RR): $^1$H NMR δ 5.50 (dd, H, J=15.4, 5.9 Hz, C-11 H), 5.43–5.19 (2H, C-5, C-6 H's), 5.17 (dd, H, or=15.4, 9.8, 1.0 Hz, C-10 H), 4.02 (apparent q, H, J=5.0 Hz, C-12 H), 3.99–3.89 (2 H), 3.65–3.53 (m, H), 2.78–2.66 (m, H, C-8 H), 2.61–2.44 (m, H, C-9 H), 2.31 (t, 2 H, J=7.6 Hz, C-2 H), 2.30–2.01 (2 H, C-7 H), 2.11 (s, 3 H, acetyl methyl), 2.04 (apparent q, 2 H, J=7.3 Hz, C-4 H), 1.65 (apparent quintent, 2 H, J=7.3 Hz, C-3 H), 1.47–1.31 (2 H, C-13 H), 1.34 (s, 3 H, isopropylidene methyl), 1.29 (s, 3 H, isopropylidene methyl), 1.23 (br s, 6 H, C-14, C-15, C-16 H's), 0.86 (s, 9 H, tert-butylsilyl), 0.84 (t, 3 H, J=5.3 Hz, C-17 H), 0.01 (s, 3 H, methylsilyl), −0.01 (s, 3 H, methylsilyl); $^{13}$C NMR δ 210.86 (+), 179.31 (C-1, +), 138.57 (C-11, −), 130.27 (−), 127.69 (−), 124.93 (−), 109.58 (isopropylidene ketal carbon, +), 77.11 (−), 72.71 (C-12, −), 68.71 (+), 54.36 (C-8, −), 49.67 (C-9, −), 38.23 (+), 33.39 (+), 31.73 (+), 30.79 (−), 26.61(+), 26.36 (2 C, coincident resonances, + and −), 25.76 (3 C, tert-butyl methyls, −), 25.53 (−), 24.66 (+), 24.41 (+), 22.57 (+), 18.16 (+), 13.97 (C-17, −), −4.53 (−), −4.85 (−).

Consecutive Hydrolysis and Oxidative Cleavage of 25RR. Referring to FIG. 5A, a solution of structure 25RR (120 mg, 0.217 mmol) in 2.5 mL of acetic acid/water (2:1, v/v) was stirred magnetically and heated to 40° C. After 4 h the resulting solution of triol 27, R$_f$=0.20, 2-propanol/hexane (1:4, v/v), was added to a solution of sodium metaperiodate (56 mg, 1.2 equiv) in 15 mL of 30% acetone/water (v/v). After 1.5 h the reaction was quenched by the addition of ethylene glycol (20 mg). After being stirred for an additional 15 min at room temperature, the solution was neutralized by the portionwise addition of sodium bicarbonate, diluted with water (20 mL), and extracted with diethyl ether (3×20 mL). The combined organic extracts were washed once with water (10 mL), dried (MgSO$_4$), filtered, and concentrated under reduced pressure. The residual oily product containing acetic acid was dissolved in diethyl ether (2 mL), and dry n-heptane (10 mL) was added. The solvents were removed by rotary evaporation (20 mm, 20° C.), and this process of solvent addition and evaporative removal was repeated three times. After final concentration under high vacuum, there was obtained 69 mg (90% material balance) of a clear oil which was completely free of contaminating acetic acid. Analysis by $^1$H NMR spectroscopy indicated that this product was a mixture containing at least 60% of methyl 8(R)-formyl-12(S)-hydroxy-5(Z),10(E)-heptadecadienoate (LGE$_2$-methyl ester, structure 29RR): $^1$H NMR a 9.47 (s, H, CHO), 5.77 (dd, H, J=15.6, 5.7 Hz, C-11 H), 5.57–5.16 (4 H, OH, C-5, C-6, C-10 H's), 4.10 (apparent q, H, J=5.2 Hz, C-12 H), 3.63 (s, 3 H, OCH$_3$), 3.48 (apparent t, H, J=9.5 Hz, C-9 H), 2.97 (ddd, H, J=9.8, 8.1, 4.5 Hz, C-8 H), 2.35–1.96 (2 H, C-7 H), 2.26 (t, 2 H, J=7.1 Hz, C-2 H), 2.22 (s, 3 H, acetyl methyl), 1.99 (apparent q, 2 H, J=7.5 Hz, C-4 H), 1.65 (apparent quintet, 2 H, J=7.9 Hz, C-3 H), 1.54–1.38 (2 H, C-13 H), 1.26 (br s, 6 H, C-14, C-15, C-16 H's), 0.84 (t, 3 H, J=6.7 Hz, C-17 H) (a minor CHO resonance was observed at δ 9.56 which was tentatively assigned to the C-8 epimer structure 29SR; this epimer accounted for less than 5% of the product mixture); $^{13}$C NMR δ 210.96 (acetyl carbonyl), 199.78 (formyl carbonyl), 174.11 (ester carbonyl), 141.61 (C-11), 131.61, 125.64, 121.90, 71.96 (C-12), 57.05, 51.55, 51.07, 37.10, 33.22, 31.64, 30.93, 27.03, 26.49, 25.00, 24.51, 22.53, 13.97 (C-17).

Concomitant Hydrolysis and Oxidative Cleavage of Structure 25SR. Referring to FIG. 5A, to a magnetically stirred solution of sodium metaperiodate (24.3 mg, 0.114 mmol, 1.5 equiv) in 2 mL of acetic acid/water (2:1, v/v) was added structure 25SR (41.9 mg, 0.076 mmol), and the mixture was heated at 40° C. After 3 h the reaction was quenched by the addition of ethylene glycol (15 mg). After an additional 10 min of stirring at room temperature the solution was neutralized by the portionwise addition of sodium bicarbonate, diluted with water, and extracted with diethyl ether (3×15 mL). The combined organic extracts were washed with water (1×5 mL), dried (MgSO$_4$), filtered, and concentrated under reduced pressure. The resulting oily product containing residual acetic acid was dissolved in diethyl ether (2 mL), and dry n-heptane (10 mL) was added. The solvents were removed by rotary evaporation (20 mm, 20° C.), and this process of solvent addition and evaporative removal was repeated three times. After final concentration under high vacuum, there was obtained 26.1 mg (93% material balance) of a yellow oil. Analysis of this oil by $^1$H NMR spectroscopy revealed three aldehydic resonances occurring at δ 9.56, 9.47, and 9.37 having approximate integration ratios of 1:2:1, respectively. The major aldehydic product, i.e., that giving rise to the resonance at δ 9.47, was assigned to the product having the C-8(R), C-9(R) configuration (structure 29RR). The aldehyde resonance occurring at δ 9.37 was assigned to anhydro-LGE$_2$-methyl ester since the characteristic downfield olefinic resonances for this compound at δ 6.93 (d, 1 H) and δ 6.36 (m, 2 H) were also observable in the spectrum. The resonance at δ 9.56 was assigned to 8-epi-LGE$_2$-methyl ester (structure 29SR) since partially purified samples of LGF$_2$ derived from prostaglandin H$_2$ invariably show resonances in this region, presumed to be due to the C-8(S),C-9(R) and C-8(R),C-9(S) epimers of LGE$_2$. This mixture was subjected to fluorenylidene derivatization for further characterization. Thus, the mixture of aldehydes (26.1 mg, 60% aldehydic products) was dissolved in CDCl$_3$ (400 μL) and placed in an NMR tube. A 200-MHz $^1$H CDCl$_3$ (400 μL) and placed in an NMR tube. A 200-MHz $^1$H NMR spectrum was taken, and then 200 μL of a 0.32M solution of fluorenylidenetri-n-butylphosphorane in CDCl$_3$ was added. The reaction was monitored by $^1$H NMR spectroscopy. Within 15 min after addition of the phosphonium ylide, the aldehydic resonances attributable to the methyl ester derivatives structure 29SR, of 8-epi-LGF$_2$ and structure 29RR of LGE$_2$ had disappeared while the aldehydic resonance of anhydro-LGE$_2$-methyl ester occurring at δ 9.37 remained unchanged.

Similarly, LGE$_2$ was prepared from structures 26SR, 26RR. Referring to FIG. 5B, LGE$_2$ was prepared by concomitant hydrolysis and oxidative cleavage. A magnetically stirred solution of structure 26RR (27.3 mg, 0.052 mmol) in 0.6 mL acetic acid/water (2:1 v/v) was warmed to 40° C. for 3 h. After 3 h, the reaction mixture was transferred to a flask containing sodium metaperiodate (13 mg, 0.0605 mmol) in 3.5 mL of 30% acetone-water and stirred at RT for 90 min. The excess sodium periodate was quenched by addition of ethylene glycol (4.7 mg). After stirring for 5 min at RT, water was added to the reaction mixture and then extracted with ether (3×10 mL). The ether extract was dried over anhydrous MgSO$_4$, filtered, and n-heptane (60 mL) was added to the filtrate. The solvent volume was reduced to 10 mL by rotary evaporation at 20° C., and then another portion of n-heptane (30 mL) and ether (15 mL) were added. The solvents were then removed completely by rotary evaporation. The flask was attached to a vacuum trap cooled to −78° C. and the tert-butyl methylsilanol byproduct removed by vacuum transfer into the trap at 0.01 mm of Hg for 30 min. The $^1$H NMR spectrum of the residual oily product (17 mg, 92%) closely resembled that of LGE$_2$ derived from PGH$_2$. For both PGH$_2$-derived and total synthetically-derived LGE$_2$, the integrated area of the aldehydic proton resonance (δ 9.46, s, 1H) was low relative to the terminal methyl proton resonance (δ 0.86, t, 3H). For the synthetic LGF$_2$ obtained above, the integrated area of the aldehydic proton resonance was 70% of that expected relative to the terminal methyl resonance.

$^1$H NMR data for LGE$_2$: δ9.46 (s, 1H), 5.75 (dd, 1H, J=5.1, 15.6 Hz, C-11 H), 5.43 (m, 3H, C-10H, C-5H, C-6H), 4.18 (m, 1H, C-12H), 3.50 (dd, 1H, J=9.7 9.6 Hz, C-9 H), 2.94 (ddd, 1H,=9.8, 9.4, 4.8 Hz, C-8 H), 2.31 (m, 3H, C-7H, C-2H), 2.25 (s, 3H), 2.05 (m, 3H, C-7H, C-4H), 1.63 (m, 2H, C-3H), 1.43 (m, 2H, C-13H), 1.27 (br m, 6H), 0.86 (t, 3H, J=6.6 Hz, C-17H).

Figure 6A:
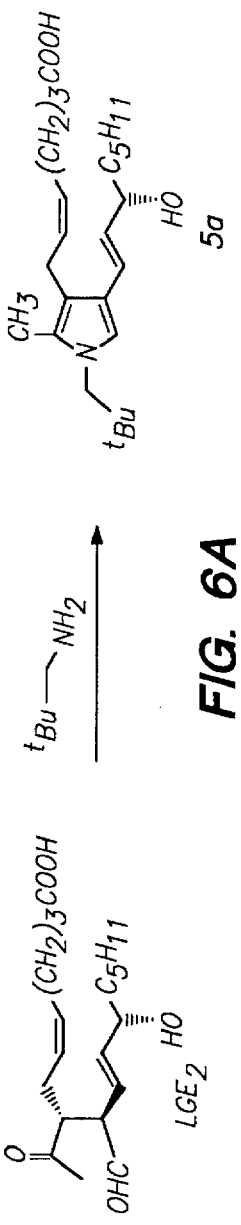
FIG. 6A is a schematic of the synthetic pathway of structure 5a [3-(6-carboxy-2-Z-hexenyl)-1-neopentyl-4-(3-hydroxy-1-E-octenyl)-2-methylpyrrole] from LGE$_2$.

3-(6-carboxy-2-Z-hexenyl)-1-neopentyl-4-(3-hydroxy-1-E-octenyl)-2-methylpyrrole (Structure 5a; see Table 1 and FIG. 6A)

Structure 5a was prepared according to a procedure described by R. Iyer et al., J. Org. Chem. 59: 6038–6043 (1994). The procedure was approximately as follows: neopentylamine (3 mg, 0.035 mmol) was added to a stirring solution of LGE$_2$ (10 mg, 0.0284) in deareated anhydrous ethanol (150 μL). (See FIG. 6A.) The reaction mixture was stirred at room temperature for 45 min under a steady stream of argon. The resulting pale yellow solution was concentrated in vacuo and the purity of the pyrrole was determined by $^1$H NMR.

The methyl ester [3-(6-carbomethoxy-2(Z)-hexenyl)-4-(3-hydroxy-1(E)-octenyl)-2-methyl-1-neopentylpyrrole; structure 45] has also been prepared by a similar method, described hereafter (FIG. 6B); the methyl ester has the characteristic of being more stable than structure 5a. Neopentylamine (32 mg, 0.375 mmol) was added to a stirring solution of 8,9-bisepi-LGE$_2$ methyl ester (structure 44) (125 mg, 0.341 mmol) in deaerated, anhydrous ethanol (1.0 mL). The reaction mixture was stirred at RT for 45 min under a steady stream of argon. The resulting pale yellow solution was concentrated in vacuo and the residue purified by HPLC on a Whatmann preparative silica gel column (WHATMAN PARTISIL®. M9 10/50) using 18% ethyl acetate in hexanes as eluting solvent (flow rate 4 mL/min; UV detection 280 nm). The major, UV-active peak (retention time 24 min) was collected under argon and concentrated in vacuo to afford structure 45 (130 mg, 91% yield) as a pale yellow oil which darkens on standing (turns brown due to decomposition of the pyrrole). As structure 45 is extremely sensitive to air, all operations were carried out under a steady stream of argon. All solvents were degassed thoroughly prior to use. The title pyrrole (structure 45) decomposes in chlorinated solvents and was hence stored at −78° C. as a solution in CD$_3$CN or C$_6$D$_6$. Pyrrole structure 45 stains orange with vanillin and is DMAB positive (R$_f$=0.22: 20% ethyl acetate in hexanes)

$^1$H NMR (200 MHz, CD$_3$CN) δ 6.64 (1H, s), 6.31 (1H, d, J=15.9 Hz), 5.68 (1H, dd, J=16.0 Hz, J=7.1 Hz), 5.31 (2H), 4.04–3.96 (1H, m), 3.61 (3 H, s), 3.55 (2H, s), 3.15 (2H, d, J=4.9 Hz), 2.32 (2H, t, J=7.5 Hz), 2.28–2.13 (2H), 2.13 (3H, s), 1.72–1.28 (10H), 0.92–0.84 (12 H)

$^{13}$C NMR (50 MHz, CD$_3$CN) δ 174.6 (+, s), 131.5 (−, d), 129.2 (−, d), 128.2 (−, d), 126.9 (+, s), 123.7 (−, d), 119.6 (+, s), 119.5 (−, d), 117.2 (+, s), 73.9 (−, d), 57.9 (+, t), 51.8 (−, q), 38.5 (+, t), 38.1 (+, t), 34.0 (+, t), 32.5 (+, s), 28.1 (−, q, 3C), 27.3 (+, t), 26.0 (+, t), 25.7 (+, t), 23.7 (+, t), 23.3 (+, t), 14.3 (−, q), 10.5 (−, q).

3-(6-carboxy-2-Z-hexenyl)-1-(6-hydroxyhexyl)-4-(3-hydroxy-1-E-octenyl)-2-methylpyrrole (Structure 5b; see Table 1)

Structure 5b was prepared according to the method described by E. DiFranco et al., Chem. Res. Toxicol. 8: 61–67 (1995). The procedure was approximately as follows: 6-amino-1-hexanol (4.3 mg, 0.037 mmol) in 100% EtOH (50 μL) was added to LGE$_2$ (11 mg, 0.31 mmol) in 100% EtOH (100 μL). The solution was stirred at room temperature for 1 h. Volatiles were then evaporated by a stream of dry N$_2$ followed by high vacuum. The crude product was purified by HPLC using 60% EtOAc/hexanes as eluant to obtain structure 5b (approximately 2.2 mg, 17%) as a light brown oil.

$^1$H NMR (300 MHz, CDCl$_3$) δ 6.63 (1H, s), 6.39 (1H, d, J=15.8 Hz), 5.74 (1H, dd, J=7.2, 15.9 Hz), 5.24–5.60 (2H), 4.15 (1H, m), 3.68 (2H, t, J=7.3 Hz), 3.15–3.22 (1H, m), 2.84–2.90 (1H, m), 1.97–2.49 (6H), 1.47–1.90 (6H), 1.18–1.45 (12 H), 0.79 –1.04 (7H).

(Z)-7-hydroxy-5-heptenoic acid (Structure 6; see Table 1)

Structure 6 was prepared according to the method described by E. DiFranco et al., Chem. Res. Toxicol. 8: 61–67 (1995). The procedure was approximately as follows: methyl 7-hydroxy-5(Z)-heptenoate (40 mg) was stirred with NaOH (47 mg) in 1:5:3 water-MeOH-THF (5.9 mL) at room temperature for 1.5 h. The resulting solution was acidified to pH 3 with 2N HCl. Then water (20 mL) was added and the mixture was extracted with EtOAc (3×20 mL). The extract was dried with MgSO$_4$ and filtered, and solvents were removed by rotary evaporation to give structure 6 (approximately 35 mg, 96%) as a colorless oil.

$^1$H NMR (300 MHz, CDCl$_3$) δ 6.92 (2H, br s), 5.60 (1H, m), 5.44 (1H, m), 4.15 (2H, d, J=6.9 Hz), 2.28 (2H, t, J=7.3 Hz), 2.10 (2H, m), 1.67 (2H, t, J=7.2 Hz). HRMS m/z (M+) calcd for C$_7$H$_{12}$O$_3$: 144.0786. Found: 144.0791.

(E)-1-chloro-1-octen-3-ol (Structure 7; see Table 1)

Structure 7 was prepared according to the method described by E. DiFranco et al., Chem. Res. Toxicol. 8: 61–67 (1995). The procedure was approximately as follows: to 1-chloro-1(E)-octen-3-one (44 mg, 0.274 mmol) in absolute ethanol (0.5 mL) was added NaBH$_4$ (21 mg). The mixture was stirred at room temperature with water (2×3 mL). Solvents were removed by rotary evaporation, and the crude product was purified by HPLC using 20% EtOAc/hexanes as eluant to obtain the alcohol, structure 7 (approximately 24 mg, 55%) as a colorless oil.

$^1$H NMR (300 MHz, CDCl$_3$) δ 6.15 (1H, d, J=13.5 Hz); 5.89 (1H, dd, J=13.5 Hz) ), 4.13 (1H, m), 1.0–1.6 (8H), 0.85 (3H, t, J=6.8 Hz).

6(-(2-pentylpyrrol-1-yl)hexanoic acid (Structure 8a; see Table 1)

Structure 8a was prepared according to the method described by E. DiFranco et al., Chem. Res. Toxicol. 8: 61–67 (1995). The procedure was approximately as follows: 4-oxononanal (50 mg, 0.320 mmol) and 6-aminocaproic acid (50 mg, 0.384 mmol) in MeOH/H$_2$O (500 μL, 19:1 v:v) were stirred for 16 h at room temperature. Solvents were then removed into a dry ice-cooled trap using high vacuum. EtOAc (1 mL) was added and the solution was filtered. The crude product was then purified by HPLC using 55% EtOAc/hexanes as eluant to obtain structure 8a (approximately 11 mg, 11%) as a tan solid.

¹H NMR (300 MHz, CDCl₃) δ 6.54 (1H, t, J=2.3 Hz), 6.04 (1H, t, J=3.1 Hz), 5.85 (1H, t, J=1.5 Hz), 3.76 (2H, t, J=7.3 Hz), 2.48 (2H, t, J=7.7 Hz), 2.34 (2H, t, J=7.4 Hz), 1.56–1.79 (6H), 1.26–1.44 (8H), 0.85–0.96 (3H). HRMS m/z (M+) calcd for $C_{15}H_{25}NO_2$: 251.1885. Found: 251.1879.

6-(2-formyl-5-hydroxymethylpyrrol-1-yl)hexanoic acid (Structure 8b; see Table 1)

Structure 8b was prepared according to the method described by F. Hayase et al., J. Biol. Chem 263: 3758–64 (1989). The procedure was approximately as follows: ε-(2-Formyl-5-hydroxymethyl-pyrrol-1-yl)-caproic Acid (Caproyl Pyrraline or structure 8b) was synthesized for use as a hapten. D-Glucose (18 g) and ε-amino caproic acid (13.1 g) were dissolved in distilled water (20 mL), and the pH was adjusted to 4.0 with acetic acid. The solution was refluxed at 100° C. for 3 h. The resulting brown solution was extracted with ethyl acetate, dried with anhydrous sodium sulfate, and concentrated. The concentrate was charged onto a silica gel column for flash chromatography in 3:1 hexane/ethyl acetate. 2,4-Dinitrophenylhydrazine-positive fractions containing caproyl pyrraline were collected and recrystallized from ether/hexane. The yield was 1 g. Proton NMR: (CDCl₃) δ 1.33–1.92 (m, 6H, 3×CH₂), 2.39 (t 2H, CH₂), 4.33 (t, 2H, CH₂), 4.72 (s, 2H, CH₂OH), 6.23 (d, 1H, pyrrole-4H), 6.99 (d, 1H, pyrrole-3H), 9.46 (s, 1H, CHO). IR 3500, 2950–2860 (br), 1725, 1645, and 1400 cm⁻¹. $UV_{max\ 297\ nm}$ (H₂O) (ε=1.61×10⁴ mol⁻¹ liter cm⁻²). Chemical ionization mass spectrometry-millimass: $C_{12}H_{17}O_4N$ as theoretical ion distribution, M₁=239 1158. Mass spectrometry analysis was performed with a HP 5985A mass spectrometer Crlewlett-Packard). Chemical ionization mass spectrometry was analyzed with methane as the reaction gas. NMR, IR, and UV properties were identical with those of synthetic neopentyl and L-lysyl pyrraline.

2-[8-acetyl-12-t-butyldimethylsiloxy-5,6-ditritio-9-(1 (S),2-isopropylidenedioxyethyl)-5(Z),10(E)-heptandecadienoic acid (Structure 10-t2; see FIG. 7)

Structure 10-t2 was prepared by the method described by R. G. Salomon et al., Prostaglandins 34: 643–56 (1987). The procedure was approximately as described below and as depicted in FIG. 7.

Methyl 7-Bromo-5-heptynoate (structure 56b). Referring to FIG. 7, a magnetically stirred solution of the hydroxy ester structure 56a (18, 19) (950 mg, 6.08 mmol) in anhydrous Et₂O (20 mL) was treated dropwise with PBr₃ (0.675 mL, 7.09 mmol) at 4° C. The reaction mixture was warmed to room temperature, stirred for 40 min., and then heated to reflux for 1 h. The resulting solution was cooled to room temperature, and then poured into ice-water (20 mL). The organic layer was separated and the aqueous layer was extracted with ether (3×10 mL). The combined ether extracts were washed with saturated aqueous NaHCO₃ (10 mL) followed by saturated aqueous NaCl (10 mL), dried over anhydrous MgSO₄, and the ether removed in vacuo. The residual liquid was filtered through a column of silica gel 60 (230–400 mesh, 30 mm high in a Pasteur pipette eluting with hexanes (50 mL). Concentration of the hexane solution in vacuo afforded structure 56b (933 mg, 70%) as a pale yellow oil, ¹H NMR (CDCl₃ 60 MHz) δ 3.92 (2H, t, J=2Hz). 3.69 (3H, s), 2.58–2.19 (4H), 2.05–1.71 (2H). Bromide structure 56b was further characterized by conversion to structure 57.

Methyl 7-Iodo-5-heptynoate (structure 56c). Anhydrous NaI (1.1 g, 6.87 mmol) was added in one portion to a stirred solution of bromide structure 56b (933 mg 4.25 mmol) in dry acetone (50 mL). A white precipitate appeared immediately. The reaction mixture was stirred for 30 min at room temperature and then filtered through celite. The filtrate was concentrated in vacuo and the residue was dissolved in ether (50 mL). The ether solution was washed with saturated aqueous NaHCO₃ (10 mL) followed by saturated NaCl (10 mL), dried over anhydrous MgSO₄, and filtered. The ether was removed in vacuo and the oily residue was purified by flash chromatography with ethyl acetate/hexanes as the eluting solvent to afford structure 56c (1.08 g, 95% ) as a clear oil; ¹H NMR (CDCl₃ 60 MHz) δ 3.77–3.67 (5H), 2.59–2.15 (4H), 2.05–1.66 (2H).

9-Oxo-8-phosphono-5decynoic Acid, P, P-Diethyl Methyl Ester (structure 57). To a magnetically stirred suspension of NaH (153 mg, 3.82 mmol, 60% oil dispersion) in dry THF (25 mL) under an argon atmosphere, was added dropwise diethyl phosphonoacetone (840 mg, 4.32 mmol) over a period of 5 min. Stirring at room temperature was continued until all NaH dissolved (4–5 h). Methyl 7-iodo-5-heptynoate (structure 56c, 920 mg, 3.45 mmol) was then added at –10° C. over a period of 10 min. The cooling bath was then removed and stirring was continued for 20 h. at room temperature. The reaction mixture was then concentrated in vacuo and the residue was treated with 10% (weight/volume) aqueous HCl (5 mL) and then extracted with ether (5×30 mL). The ether extracts were washed with saturated aqueous NaCl (20 mL), dried over anhydrous MgSO₄, and filtered. Concentration of the ether extracts in vacuo and purification of the residue by flash chromatography (70 mm diameter by 150 mm high column) with ethyl acetate/hexane (70% v/v) as eluting solvent afforded α-ketophosphonate structure 57 (684 mg, 60% yield) as a clear oil; ¹H NMR (CDCl₃ 200 MHz) a 4.21–4.05 (4H), 3.67 (s, 3H), 3.35 (ddd, H, J=23.4, 10.7, 3.9 Hz), 3.00–2.71 (m, H), 2.71–2.47 (m, H), 2.46–2.29 (5H), 2.28–2.10 (m, 2H), 1.76 (apparent quintet, 2H, J=7.3 Hz), 1.33 (t, 6H, J=7.5 Hz); mass spectrum m/e 332.1353 (M⁺) calcd for $C_{15}H_{25}O_6P$, 332.1389.

Methyl 8-[(2,2-Dimethyl-1,3-dioxolan-4-yl)methylene]-9-oxo-5-decynoate (structure 59). A magnetically stirred suspension of NaH (160 mg, 6.66 mmol, 60% oil dispersion) in THF (15 mL) at 5° C. under argon, was treated with a solution of α-ketophosphonate (structure 57) (2.02 g, 6.06 mmol) in THF (10 mL) over a period of 10 min. Stirring at –5° C. was continued for 4 h until a clear light brown solution was obtained. A solution of isopropylidene-L-glyceraldehyde (structure 58) (947 mg, 7.27 mmol) in THF (4 ml) was then added dropwise over 30 min. Stirring was continued at 5° C. for 30 min and then at room temperature for 18 h. The THF was removed by rotary evaporation and the residue was treated with water (20 mL), and extracted into ether (5×50 mL). The combined ether extracts were washed with water and dried over anhydrous MgSO₄. Removal of the solvents in vacuo followed by flash chromatography with ethyl acetate/hexane (30% v/v) as eluting solvent, afforded structure 59 (1.29 g. 69% yield) as a mixture of E and Z isomers. The two geometrical isomers were separated by HPLC on a WHATMAN® PARTISIL® 10/50 column with ethyl acetate/hexanes (22% V/V) as eluting solvent at a flow rate 15 ml/min. The less polar Z isomer (R.t.-4.09 min. 35 mg); ¹H NMR (CDCL₃ 200 MHz) δ 6.10 (d, H, J=7.0 Hz), 4.98 (apparent q, H, J=7.0 Hz), 4.34 (dd, H, J=8.2, 6.9 Hz), 3.67 (s, 3H), 3.61 (dd, H, J=8.3, 7.2 Hz), 3.21 (br s, 2H), 2.43 (t, 2H, J=7.5 Hz), 2.31 (s, 3H), 2.3–2.2 (2H), 1.82 (apparent quintet, 2H, J=7.1 Hz), 1.45 (s, 3H) 1.37 (s, 3H); mass spectrum m/e 308.1660 (M⁺) calcd. for $C_{17}H_{24}O_5$, 308.1624; and the more polar E isomer (R.t.-4.94 min. 85 mg); ¹H NMR (CDCl₃ ₂₀₀ MHz) a 6.61 (d, H, J=7.8 Hz), 5.07 (apparent q, H, J-7.0 Hz), 4.29 (dd, H, J=8.3, 6.5 Hz), 3.71 (dd, H, J=8.2, 6.9 Hz), 3.66 (s, 3H), 3.32

(dt, H, J=17.1, 2.3 Hz), 3.04 (dt, H, J=17.1, 2.1 Hz), 2.42–2.34 (5H), 2.24–2.09 (2H), 1.77 (apparent quintet, 2H, J=7.2 Hz), 1.49 (s, 3H), 1.43 (s, 3H); mass spectrum m/e 308.1659 (M$^+$) calcd. for $C_{17}H_{24}O_5$, 308.1624.

Methyl (9R,10E,12S)-8-Acetyl-12-(tert-butyldimethylsiloxy)-9-[(4-R)-2,2-dimethyl-1, 3-dioxolan-4-yl]-10-heptadecen-5-ynoate (structure 61). A magnetically stirred solution of 1-iodo-3(S)-t-butyldimethylsiloxy-10(E)-octene (1.306 g. 3.4 mmol) in $Et_2O$ (5.7 mL), at −78° C. under argon, was treated dropwise with t-butyllithium (1.7M in pentane, 4.17 mL, 7.09 mmol) over a period of 5 min. Stirring at this temperature was continued for 2.5 h. A solution of copper (I) pentyne (463 mg, 3.54 mmol) in hexamethylphosphoroustriamide (1.29 mL, 7.09 mmol) made up 30 min. prior to use was then added dropwise over a period of 10 min. The resulting golden yellow suspension was stirred at −78° C. for 25 min and treated dropwise with a solution of anhydrous $MgBr_2$ (0.2M) in THF (16.2 mL, 3.60 mmol, 1.1 equiv.). After complete addition, a solution of E and Z enones structure 59 in diethyl ether (1 ml) was added slowly over a 15 min period. The resulting dark orange suspension was stirred at −78° C. for 45 min. The reaction mixture was warmed to 0° C. and then quenched by addition of saturated aqueous $NH_4Cl$ (25 mL). The organic layer was separated and extracted with $Et_2O$ (4×30 mL). The ether layers were consecutively washed with 2% (v/v) aqueous $H_2SO_4$ (4×15 mL), and saturated aqueous $NaHCO_3$ (15 mL), then combined, and dried over anhydrous $MgSO_4$. This solution was concentrated in vacuo and the residue was purified by flash chromatography with ethyl acetate/hexane (12% v/v) as eluting solvent to afford structure 61 (1.224 g) as a mixture of diasteriomers and unreacted enone structure 59 (70 mg). The isomeric mixture of structure 61 was purified by HPLC on a WHATMAN® PARTISIL® M20 10/50 column with the solvent system ethyl acetate, tert-butyl methyl ether, heptane (7:10:83 v/v/v) at a flow rate of 8 mL/min affording a less polar 8S isomer of structure 61 (152 mg, 8.5% yield): $^1$H NMR (CDCl$_3$ 200 MHz) δ 5.48 (dd, H, J=16.0, 6.3 Hz), 5.28 (dd, H, J=16.0, 10.0 Hz), 3.97 (m, H), 3.91–3.81 (2H), 3.64 (s, 3H), 3.52 (m, H), 3.14 (m, H), 2.38 (t, 4H, J=7.4 Hz), 2.23 (s, 3H), 2.25–2.08 (4H), 1.76 (apparent quintet, 2H, J=7.2 Hz), 1.39 (s, 3H), 1.31 (s, 3H), 1.35–1.14 (8H), 0.86–0.83 (12H), −0.01 (s, 3H), −0.02 (s, 3H); mass spectrum m/e 550.3701 (M$^+$) calcd. for $C_{31}H_{54}O_6Si$, 550.3690; and a more polar 8S isomer of structure 61 (764 mg. 43% yield); $^1$H NMR (CDCl$_3$ 200 MHz) δ 5.50 (dd, H, J=15.7, 6.2 Hz), 5.12 (dd, H, J=15.8, 10.1 Hz), 3.98 (m, H), 3.95–3.85 (2H), 3.63 (s, 3H), 3.55 (m, H), 2.82 (apparent q, H, J-7.2 Hz), 2.49 (m, H), 2.37 (t,2H, J=7.3 Hz), 2.21 (s, 3H), 2.25–2.09 (4H), 1.74 (apparent quintet, 2H, J=7.5 Hz), 1.32 (s, 3H), 1.27 (s, 3H), 1.47–1.11 (8H), 0.88–0.85 (12H), −0.01 (s, 3H), −0.03 (s, 3H); mass spectrum m/e 550.3662 (M$^+$) calcd. for $C_{31}H_{54}O_6Si$, 550.3690.

Methyl (5Z,8R,9R,10E,12S)-8-Acetyl-12-(tert-butyldimethylsiloxy)-9-[(4R)-2,2-dimethyl-1,3-dioxolan-4-yl]-5,10-heptadecadienoate-5, 6-t2 (structure 10-2). The 8R isomer of acetylene structure 61 (551 mg) was partially tritiated over a 5% palladium on calcium carbonate catalyst (14.8 mg) in ethyl acetate/hexanes (50% v/v, 3.25 mL) containing 3.6-dithia-1, 8-octanediol (9.05 µg) and 2-dimethylaminoethanol (444 µg) at just slightly above atmospheric pressure. After 12 h an additional portion (38 mg) of catalyst was added and the reaction mixture was stirred under the tritium atmosphere until evidence of a second product namely alkene-10t2 appeared. This new product was detected by TLC, with ethyl acetate/hexanes (15% V/V) as developing solvent, staining with vanillin indicator; $R_f$s acetylene structure 61—0.30, alkene structure 10-t2 −0.38. The reaction mixture was then filtered through diatomaceous earth and concentrated in vacuo to a colorless oil. This mixture was separated by HPLC on a partisil M20 column with ethyl acetate/hexanes (12% v/v) as eluting solvent delivered at 10 mL/min through a refractive index detector. Unreacted acetylene structure 61 (R.t.-42.0 min) was recovered (251 mg, 45%), and tritiated alkene structure 10-t2 (R.t.-27.5 min) was obtained (212.5 mg, 71% yield); $^1$H NMR (CDCl$_3$ 200 MHz) δ 5.45 (dd, H, J=15.2, 5.9 Hz), 5.16 (dd, H, J=15.2, 9.8 Hz), 4.08– 3.85 (3H), 3.62 (s, 3H), 3.65–3.51 (m, H), 2.70 (m, H), 2.25 (c, 2H, J=7.3 Hz), 2.17–2.09 (2H, 2.08 (s, 3H), 1.99 (t, 2H, J=7.3 Hz), 1.62 (apparent quintet, 2H, J=7.3 Hz), 1.42–1.10 (8H), 1.32 (s, 3H), 1.27 (s, 3H), 0.86–0.81 (12H), −0.01 (s, 3H), −0.03 (s, 3H).

The resulting tritiated alkene structure 10-t2, containing 63.7 mCi/mg tritium (35.4 Ci/mmol), was converted to structure 63-t2 as described above for $LGE_2$.

BSA-pyrazole Isostere Conjugate

BSA-pyrazole Isostere Conjugate was prepared according to the method described by M. E. Kobierski et al., J. Org. Chem. 59: 6044–50 (1994). The method was performed approximately as follows (see FIGS. 8A, 8B, 8C).

Figure 8A:
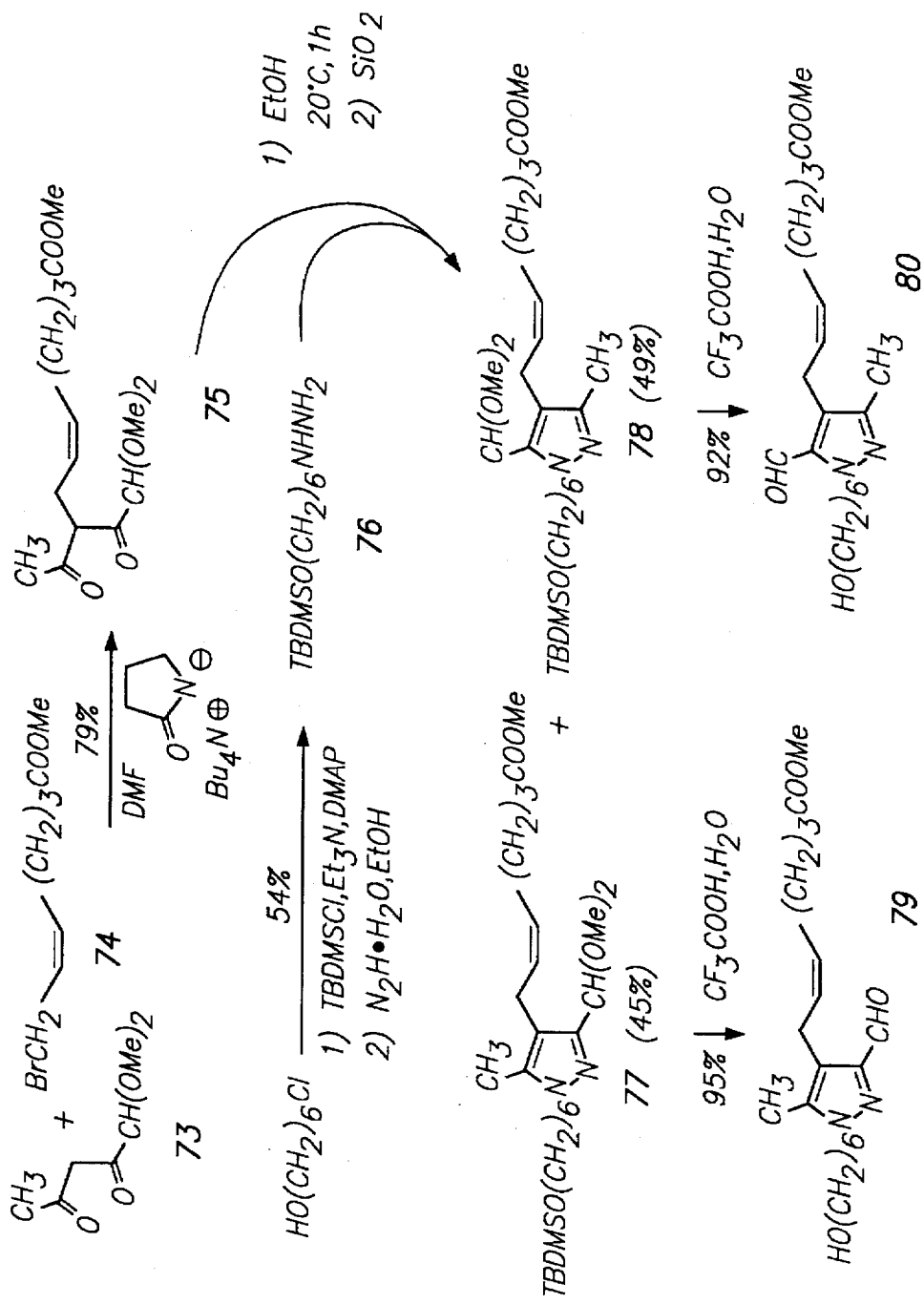
FIG. 8A is a schematic depicting the synthesis of structures 79 [4-(6-Carbomethoxy-2(Z)-hexenyl)-1-(6-hydroxyhexyl)-5-methylpyrazole-3-carboxaldehyde] and 80 [4-(6-Carbomethoxy-2(Z)-hexenyl)-1-(6-hydroxyhexyl)-3-methylpyrazole-5-carboxaldehyde] from structures 73 [1.1-dimethoxy-2,4-pentanedione] and 74 [methyl 7-bromo-5-heptenoate]

Methyl 8-Acetyl-10, 10-dimethoxy-9oxo-5(Z)-decenoate (structure 75). Referring to FIG. 8A, into a solution of 1,1-dimethoxy-2,4-pentanedione (structure 73. 863.9 mg, 5.43 mmol) in N N-dimethylformamide (2.5 mL) was added a stock solution of tetra-n-butylammonium 2-pyrrolidonide in N N-dimethylformamide (12.49 mL. 5.43 mmol). The solution was stirred 15 min at room temperature and then methyl 7-bromo-5-heptenoate (structure 74, 1.0 g, 4.52 mmol) in N N-dimethylformamide (2.5 mL) was added and the reaction stirred another 30 min. TLC analysis in ethyl acetate/hexanes (20% v/v indicated total disappearance of structure 74, excess structure 73 ($R_f$=0.27) and a dark brown-staining spot ($R_f$=0.14). the reaction mixture was poured into aqueous ammonium chloride (50 mL) and extracted with diethyl ether (4×50 mL). The combined ether extracts were dried over magnesium sulfate, filtered, and concentrated by rotary evaporation to produce an orange liquid. This liquid was purified by flash chromatography (70 mm diameter by 200 mm high column) using ethyl acetate/hexanes (20% v/v) as the eluting solvent. An initial 400 mL was eluted and then fractions (30×50 mL) were collected. Fractions 10–24 were pooled and concentrated to afford structure 75 as a slightly yellow liquid that showed a single spot at ($R_f$=0.14 upon TLC analysis in the same solvent (987.7 mg, 73% yield): $^1$H NMR (CDCl$_3$) δ 5.45–5.25 (2 H, m), 4.41 (1 H, s), 4.00 (1 H, t, J=7.2 Hz), 3.64 (3 H, s), 3.39 (3 H, s), 3.35 (3 H, s), 2.52–2.44 (2H), 2.28 (2 H, t, J=7.5 Hz), 2.21 (3 H, s), 2.12–2.01 (2 H), 1.72–1.57 (2 H); $^{13}$C NMR (50 MHz, CDCl$_3$) δ 203.12, 179.74, 173.93, 131.59, 126.00, 103.91, 60.80, 54.98, 51.48, 33.37, 30.54, 26.43, 26.03, 24.56; mass spectrum m/z (M−31) calcd for $C_{15}H_{24}O_6$ 269.1389, found 269.1391.

1-(tert-Butyldimethylsiloxy)-6-chlorohexane. To a stirred solution of 6-chloro-1-hexanol (8.1 g, 60 mmol), triethylamine (9.2 g, 12.7 mL, 90 mmol), and DMAP (750 mg, 0.1 equiv., 6.1 mmol) in methylene chloride (100 mL) was added tert-butyldimethylchlorosilane (10.85 g, 1.2 equiv, 72 mmol). The reaction was allowed to proceed overnight under a nitrogen atmosphere. TLC analysis in ethyl acetate indicated complete disappearance of staring alcohol ($R_f$= 0.43) and the appearance of a new spot ($R_f$=0.67). The organic solution was washed with water (2×30 mL) and saturated ammonium chloride solution (1×25 mL) and dried over MgSO$_4$. Solvents were removed by rotary evaporation and the residue distilled to afford the title compound (12.03 g, 80%) as a colorless liquid: bp 70° C./0.1 Torr; $^1$H NMR (200 MHz, CDCl$_3$) δ 3.58 (2 H, t, (J=6.26 Hz), 3.50 (2 H, t, (J=6.70 Hz), 1.86–1.69 (2 H), 1.60–1.28 (6 H), 0.86 (9 H, s), 0.02 (6 H, s); mass spectrum m/z (M$^+$) calcd for C$_{12}$H$_{27}$ClOSi 250.1520, found 250.1396.

6-(tert-Butyldimethylsiolxy)hexylhydrazine (structure 76). To a refluxing solution of 85% hydrazine hydrate (18.0 g, 0.36 mol, 7.5 equiv) in ethanol (30 mL) was added dropwise over 3 h a solution of I-(tert-butyldimethylsiloxy)-6-chlorohexane (12.03 g 0.048 mmol) in ethanol (40 mL). After the addition was complete, the solution was refluxed for another 3 h. The ethanol was then removed by distillation at atmospheric pressure. To the residue was added saturated aqueous KOH solution (50 mL), and the resulting mixture was extracted with ether (5×50 mL). The ether extracts were dried over anhydrous potassium carbonate and filtered, and the ether was removed by rotary evaporation. Fractional distillation of the residue under reduced pressure afforded the desired hydrazine structure 76 (7.90 g, 66.5%) as a colorless liquid: bp 98° C./0.3 Torr, $^1$H NMR (200 MHz, CDCl$_3$) δ 3.56 (2 H, t, J=6.40 Hz), 3.12 (3 H, br s, NH), 2.72 (2 H, t, J=7.03 Hz), 1.59–1.26 (8 H), 0.85 (9 H, s), 0.00 (6 H. s); mass spectrum m/z (M$^+$) calcd for C$_{12}$H$_{30}$N$_2$OSi 246.2127, found 246.2110.

Tetrasubstituted Pyrazole Isomers structures 77 and 78. Monoalkylhydrazine structure 76 (2.2 g, 9 mmol) was slowly added to a magnetically stirred solution of diketone structure 75 (1.8 g, 6 mmol) in absolute ethanol (2.5 mL). The resulting reaction mixture was stirred at room temperature for 1 h. Solvent was then removed by rotary evaporation, and the residue was purified by flash chromatography eluting with 20% ethyl acetate in hexane to afford the isomeric pyrazole structures 77 (1.40 g) and 78 (1.50 g) in 94% total yield. The ratio of 17:18 is 1:1.07.

1-(6-(tert-Butyldimethylsiloxy)hexyl)-4-(6-carbomethoxy-2(Z)-hexenyl)-3-(dimethoxymethyl)-5-methylpyrazole (structure 77). TLC analysis using ethyl acetatehexanes 1:4 (v/v) shoed a single spot at R$_f$=0.08 that was visualized with iodine: $^1$H NMR (200 MHz, CDCl$_3$) δ 5.40 (m, 3 H), 4.06 (t, 2 H, J=7.4 Hz), 3.67 (s, 3 H), 3.54 (t, 2 H, J=6.4 Hz), 3.42 (s, 6 H), 3.39 (d, 2 H, J=5.2 Hz), 2.40 (t, 2 H, J=7.5 Hz), 2.20 (m, 2 H), 2.20 (s, 3 H), 1.55 (m, 10 H), 0.87 (s, 9 H), 0.02 (s, 6 H).

1-(6-(tert-Butyldimethylsiloxy)hexyl)-4-(6-carbomethoxy-2(Z)-hexenyl)-5-(dimethoxymethyl)-3-methylpyrazole (structure 78). TLC analysis using ethyl acetatehexanes 1:4 (v/v) showed a single spot at R$_f$=0.23 that was visualized with iodine: $^1$H NMR (200 MHz, CDCl$_3$) δ 5.40 (m, 2 H), 5.38 (s, 1 H), 4.18 (t, 2 H, J=7.4 Hz), 3.64 (s, 3 H), 3.60 (t, 2 H, J=6.4 Hz), 3.35 (s, 6 H), 3.21 (d, 2 H, J=5.2 Hz), 2.38 (t, 2 H, J=7.5 Hz), 2.16 (m, 2 H), 2.11 (s, 3 H), 1.52 (m, 10 H), 0.88 (s, 9 H), 0.02 (s, 6 H).

A determination of the substitution patterns in these isomeric tetrasubstituted pyrazoles was made by correlation with the derivatives structures 79 and 80, respectively. Thus, the isomeric pyrazoles structure 77 and 78 were characterized further by thorough NMR analysis of the products of hydrolytic removal of the acetal and silyl ether protecting groups.

4-(6-Carbomethoxy-2(Z)-hexenyl)-1-(6-hydroxyhexyl)-5-methylpyrazole-3-carboxaldehyde (structure 79). Pyrazole acetal structure 77 (0.5 g, 0.98 mmol) was treated with 90% TFA (11.0 in water and stirred at room temperature for 30 min. TLC analysis showed one major UV-active spot (R$_f$=0.25) with 30% ethyl acetate in hexane. TFA and water were removed by rotary evaporation. The remaining organic residue was purified by flash chromatography with 30% ethyl acetate in hexane as eluting solvent to yield structure 79 (0.326 g, 95% yield). TLC analysis using ethyl acetate-hexanes 3:7 (v/v) showed a single spot at R$_f$=0.25 that was visualized with iodine: $^1$H NMR (200 MHz, CDCl$_3$) δ 9.95 (s, 1 H), 5.40 (m, 2 H), 4.34 (t, 2 H, J=6.5 Hz), 4.09 (t, 2 H, J=7.3 Hz), 3.68 (s, 3 H), 3.46 (d, 2 H, J=5.3 Hz), 2.36 (t, 2 H, J=7.4 Hz), 2.22 (m, 2 H), 2.21 (s, 3 H), 1.72 (m, 6 H), 1.40 (m, 4 H); $^{13}$C NMR (50 MHz, CDCl$_3$) δ 187.04, 173.35, 143.23, 137.10, 128.10, 127.74, 118.42, 67.32, 50.94, 49.21, 32.85, 29.07, 27.31, 26.03, 25.49, 24.57, 24.17, 20.79, 8.66; mass spectrum m/z (M$^+$) for C$_{18}$H$_{30}$N$_2$O$_4$ calcd 350.2205, found 350.2197.

4-(6-Carbomethoxy-2(Z)-hexenyl)-1-(6-hydroxyhexyl)-3-methylpyrazole-5-carboxaldehyde (structure 80). The procedure was the same as used for making structure 79. Pyrazole acetal structure 78 (0.5 g, 0.98 mmol) gave a crude product that was purified by flash chromatography with 30% ethyl acetate in hexane to afford structure 80 (0.316 mg, 92% yield). TLC analysis using ethyl acetate-hexanes 1:4 (v/v) showed a single spot at R$_f$=0.13 that was visualized with iodine: $^1$H NMR (200 MHz, CDCl$_3$) δ 9.85 (s, 1 H), 5.39 (m, 2 H), 4.39 (t, 2 H, J=7.3 Hz), 4.30 (t, 2 H, J=6.5 Hz), 3.66 (s, 3 H), 3.38 (d, 2 H, J=5.1 Hz), 2.34 (t, 2 H, J=7.4 Hz), 2.20 (m, 2 H), 2.19 (s, 3 H), 1.72 (m, 6 H), 1.38 (m, 4 H); $^{13}$C NMR (200 MHz, CDCl$_3$) δ 178.96, 173.24, 145.74, 134.33, 128.85, 127.41, 125.70, 67.43, 50.93, 42.80, 32.73, 29.70, 27.27, 26.03, 25.27, 24.45, 23.98, 20.38, 10.82; mass spectrum m/z (M$^+$) for C$_{19}$H$_{30}$N$_2$O$_4$ calcd 350.2205, found 350.2201.

4-(6-Carbomethoxy-2(Z)-hexenyl)-1-(6-hydroxyhexyl)-5-methyl-3-(3-oxo-1(E)-octenyl)pyrazole. Referring to FIG. 8B, to a stirred suspension of sodium hydride (59.8 mg of a 50% oil dispersion, 1.247 mmol) in tetrahydrofuran (10 mL) was added dimethyl (2-oxoheptyl)phosphonate (285.7 mg, 1.286 mmol) dropwise over 10 min. This was stirred 4 h at room temperature, and then the thick, whim mixture was cooled to −5° C. Pyrazole aldehyde structure 79 (95 mg, 0.277 mmol) was dissolved in tetrahydrofuran (5 mL) and also cooled to −5° C. It was added to the reaction mixture dropwise over 30 min and stirred another 30 min at −5° C. and then at room temperature 20 h. TLC analysis in ethyl acetate/hexanes (75% v/v) showed numerous spots, including a UV-active one that stained greenish-brown in vanillin (R$_f$=0.35) that was thought to be the desired product. The tetrahydrofuran was removed by rotary evaporation and the residue taken up in water (25 mL). The aqueous mixture was extracted with diethyl ether (4×30 mL), and the combined ethereal extracts were washed with water (50 mL), dried over magnesium sulfate, filtered, and concentrated. The remaining yellow oil was separated by flash chromatography (30 mm diameter by 170 mm high column) utilizing ethyl acetate/hexanes (75% v/v) as eluting solvent. The major UV-active product was collected and solvent was removed by rotary evaporation to yield the title compound as a yellow oil (98.7 mg, 82% yield). TLC analysis using ethyl acetate-hexanes 1:3 (v/v) showed a single spot at R$_f$=0.35 that was visualized with vanillin: $^1$H NMR (200 MHz, CDCl$_3$) δ 7.50 (1 H, d, J=16.2 Hz), 6.81 (1 H, d, J=16.2 Hz), 5.41–5.33 (2 H, m), 4.04 (2 H, t, J=7.4 Hz), 3.69 (3 H, s), 3.63 (2 H, t, J=6.3 Hz), 3.24 (2 H, d, J=4.9 Hz), 2.60 (2 H, t, J=7.5 Hz), 2.38 (2 H, t, J=7.4 Hz), 2.28–2.16 (2 H), 2.19 (3 H, s), 1.89–1.54 (8 H), 1.51–1.26 (8 H), 0.89 (3 H, t, J=6.4 Hz); $^{13}$C NMR (50 MHz, CDCl$_3$) δ 200.39, 173.40, 143.31, 136.11, 132.13, 128.33, 128.11, 124.84, 118.01, 61.92, 50.91, 48.88, 40.49, 32.84, 31.79, 30.92, 29.53, 26.12, 25.62, 24.56, 24.07, 23.52, 21.89, 21.13, 13.34, 8.87; mass spectrum m/z (M$^+$) calcd for $C_{26}H_{42}N_2O_4$ 446.3144, found 446.3131.

1-(6-Acetoxyhexyl)-4-(6-carbomethoxy-2(Z)-hexenyl)-5-methyl-3-(3-oxo-1(E)-octenyl)pyrazole (structure 81). A mixture of the above hydroxy enone (96.9 mg, 0.217 mmol) and pyridine (4.1 mL) was stirred at room temperature. Acetic anhydride (1.11 g, 10.86 mmol) was added dropwise and the reaction stirred for 2 h. TLC analysis in ethyl acetate/hexanes (75% v/v) showed no starting material and just one spot ($R_f$=0.50) that was UV-active and stained brown in vanillin. Methanol (2.1 mL) was added and the mixture stirred for 15 h. Methanol and pyridine were removed by rotary evaporation and high vacuum. The crude product was purified by flash chromatography (15 mm diameter by 130 mm high column) using ethyl acetate/hexanes (50% v/v) as the eluant. The major UV-active product was collected and concentrated to afford structure 81 as a yellowish oil that showed a single spot on TLC analysis (94.1 mg, 89% yield); $^1$H NMR (CDCl$_3$) δ 7.47 (1 H, d, J=16.2 Hz), 6.78 (1 H, d, J=16.2 Hz), 5.39–5.31 (2 H, m), 4.02 (2 H, t, J=6.5 Hz), 4.00 (4 H, t, J=7.4 Hz), 3.66 (3 H, s), 3.21 (2 H, d, J=4.9 Hz), 2.57 (2 H, t, J=7.5 Hz), 2.35 (2 H, t, J=7.5 Hz), 2.26–2.13 (2 H), 2.15 (3 H, s), 2.01 (3 H, s), 1.82–1.59 (8 H), 1.36–1.23 (8 H), 0.86 (3 H, t, J=6.5 Hz); $^{13}$C NMR (50 MHz, CDCl$_3$) δ 200.92, 173.95, 169.05, 144.00, 136.60, 132.81, 128.87, 128.73, 125.35, 118.55, 64.24, 51.48, 49.50, 41.06, 33.42, 31.50, 30.10, 28.36, 26.67, 26.27, 25.55, 24.65, 24.10, 22.47, 21.71, 20.96, 13.91, 9.42; mass spectrum m/z (M$^+$) calcd for $C_{26}H_{44}N_2O_5$ 488.3250, found 488.3244.

1-(6-Acetoxyhexyl)-4-(6-carbomethoxy-2(Z)-hexenyl)-3-(3-hydroxy-1(E)-octenyl)-5-methylpyrazole. Acetoxy enone 21 (93.0 mg, 0.190 mmol) was dissolved in 0.4M methanolic cerium(III) chloride heptahydrate (70.9 mg, 0.190 mmol in 475 μL of methanol). Sodium borohydride (7.4 mg, 0.190 mmol) was slowly added, and the reaction was stirred at room temperature for 15 min. TLC analysis in ethyl acetate/hexanes (75% v/v) indicated that the starting material had been totally consumed and there were three products, with one of the spots being more intensely UV-active ($R_f$=0.37). Water (15 mL) was added to the reaction mixture, which was then extracted with diethyl ether (3×20 mL). The combined ether extracts were dried over magnesium sulfate, filtered, and concentrated by rotary evaporation. TLC in the same solvent system now shoed only the major product spot. The allylic alcohol product was a colorless oil that did not require further purification (75.8 mg, 81% yield); $^1$H NMR (CDCl$_3$) δ 6.50 (1 H, d, J=16.0 Hz), 6.27 (1 H, dd, d=16.0, 6.5 Hz), 5.39–5.31 (2 H, m), 4.22 (1 H, q, J=6.5 Hz), 4.04 (2 H, t, J=6.7 Hz), 3.99 (2 H, t, J=7.4 Hz), 3.69 (3 H, s), 3.17 (2 H, d, J=4.4 Hz), 2.37 (2 H, t, J=7.4 Hz), 2.22–2.13 (2 H), 2.15 (3 H, s), 2.04 (3 H, s), 1.83–1.55 (8 H), 1.43–1.23 (10 H), 0.89 (3 H, t, J=6.4 Hz); $^{13}$C NMR (50 MHz, CDCl$_3$) δ 174.02, 145.63, 135.79, 133.10, 129.43, 128.27, 120.93, 115.16, 73.26, 64.36, 51.54, 49.09, 37.26, 33.46, 31.80, 30.28, 28.41, 26.67, 26.32, 25.57, 25.15, 24.70, 22.59, 21.72, 20.96, 14.02, 9.47; mass spectrum m/z (M$^+$) calcd for $C_{28}H_{46}N_2O_5$ 490.3406, found 490.3405.

1-(6-Acetoxyhexyl)-3-(3-(tert-butyldimethylsiloxy)-1(E)-octenyl)-4-(6-carbomethoxy-2(Z)-hexenyl)-5-methylpyrazole (Structure 82). The above allylic alcohol (74.6 mg, 0.152 mmol) and pyridine (60.1 mg, 0.759 mmol) were stirred together in methylene chloride (7.5 mL). tert-Butyldimethylsilyl triflate (120.5 mg, 0.456 mmol) was added dropwise, and the reaction mixture was stirred for 3 h at room temperature. TLC analysis in ethyl acetate/hexanes (50% v/v) showed the disappearance of the starting alcohol ($R_f$=0.13) and formation of a UV-active spot that was black in vanillin ($R_f$=0.58). Methylene chloride and excess pyridine were removed under reduced pressure. The remaining crude product and accompanying white solid were separated by flash chromatography (15 mm diameter by 150 mm high column) with ethyl acetate/hexanes (30% v/v) as the solvent. The major UV-active product was collected and the solvent removed by rotary evaporation to provide structure 82 as a colorless oil. TLC analysis using ethyl acetate/hexanes 3:7 (v/v) showed a single spot at $R_f$=0.30 (75.3 mg, 82%y yield); $^1$H NMR (CDCl$_3$) δ 6.39 (1 H, d, J=16.2 Hz), 6.15 (1 H, dd, J=16.1, 5.9 Hz), 5.36–5.29 (2 H, m), 4.17 (1 H, q, J=6.3 Hz), 4.01 (2 H, t, J=6.6 Hz), 3.94 (2 H, t, J=7.4 Hz), 3.65 (3 H, s), 3.14 (2 H, d, J=5.0 Hz), 2.33 (2 H, t, J=7.5 Hz), 2.19–2.10 (2 H), 2.11 (3 H, s), 2.01 (3 H, s), 1.78–1.48 (8 H), 1.45–1.22 (10 H), 0.89–0.80 (12 H), 0.02 (3 H, s), 0.00 (3 H, s); $^{13}$C NMR (50 MHz, CDCl$_3$) δ 173.89, 170.97, 145.98, 135.73, 133.92, 129.55, 128.15, 119.76, 114.98, 73.80, 64.36, 51.48, 49.10, 38.38, 33.48, 31.85, 30.34, 28.41, 26.72, 26.58, 26.38, 26.16, 25.91, 25.62, 24.92, 24.75, 22.59, 21.82, 20.96, 14.03, 9.45, −4.27, −4.79; mass spectrum m/z (M$^+$) calcd for $C_{34}H_{60}N_2O_5Si$ 604.4271, found 604.4267.

1-(6-Acetoxyhexyl)-3-(3-(tert-butyldimethylsiloxy)-3-tritio-1(E)-octenyl-4-(6-carbomethoxy-2(Z)-hexenyl)-5-methylpyrazole (structure 82t). The acetoxy pyrazole enone structure 81 (40 mg, 0.092 mmol) was dissolved in 500 μL of a solution of cerium(III) chloride in methanol (0.4M). Solid NaBT$_4$ (2 mg, 0.05 mmol, specific activity 490 mCi/mmol) was carefully added to the reaction mixture, and the mixture was stirred for 30 min at room temperature. TLC analysis in 75% ethyl acetate/hexane showed the presence of a new spot ($R_f$=0.35) along with starting material ($R_f$=0.5). Water (4 mL) was added to the reaction mixture, which was extracted with diethyl ether (5×5 mL). The combined ether extracts were dried (MgSO$_4$), filtered, and concentrated in vacuo. The crude residue was purified by silica gel chromatography with 75% ethyl acetate/hexane as eluant to give the desired α-tritio alcohol (14.8 mg, 83% based on consumed starting enone) as a colorless oil and the starting enone structure 81 (18.9 mg). The specific activity of the product was determined as follows. The product was dissolved in 10 mL of ethyl acetate, and a 50 μL aliquot was withdrawn from it and further diluted to 1 mL (200×) with ethyl acetate. Three 100 μL aliquots of this diluted solution were counted in a liquid scintillation counter. The average count was 724 366 dpm. From this the specific activity of the alcohol was found to be 21.8 mCi/mmol. This α-tritio alcohol was treated with tert-butyldimethylsilyl triflate as for the unlabeled alcohol above to deliver the title silyl ether structure 82t.

3-(3-(tert-Butyldimethylsiloxy)-1(E)-octenyl)-4-(6-carboxy-2(Z)-hexenyl)-1-(6-hydroxyhexyl)-5-methylpyrazole (structure 83). Pyrazole diester structure 82 (73.0 mg, 0.121 mmol), tetrahydrofuran (2.7 mL), and methanol (4.0 mL) were stirred while an aqueous 1M NaOH solution (14.15 mg, 0.363 mmol, 363 μL of solution) was slowly added, and the mixture was then stirred at room temperature for 4 h. TLC analysis in ethyl acetate/hexanes (75% v/v) showed a small amount of starting acetoxy ester ($R_f$=0.81), a presumed intermediate ($R_f$=0.49), and possibly the desked product as a streak ($R_f$=0.05 to 0.18). (Note: acids are known to streak on TLC plates in certain solvents.) An additional quantity of 1M NaOH (9.7 mg, 0.242 mmol, 242 μL of solution) was added and the reaction stirred another 2 h. TLC analysis in 89% hexanes/10% 2-propanol/1% acetic acid (v/v) showed mainly one product ($R_f$=0.14). The reaction mixture was acidified to pH 5 with a saturated aqueous citric acid solution and extracted with ethyl acetate (3×20 mL). The combined organic extracts were washed with water (2×20 mL), dried over magnesium sulfate, and filtered, and the solvent was removed by rotary evaporation. The crude product was purified by flash chromatography (15 mm diameter by 140 mm high column) with a solvent of 89% hexanes/10% 2-propanol/1% acetic acid (v/v/v). The major UV-active product was collected, and solvents were removed to provide structure 83 as a pale yellow oil that showed a single spot on TLC analysis (58.9 mg, 89% yield): $^1$H NMR (CDCl$_3$) δ 6.40 (1 H, d, J=16.1 Hz), 6.15 (1 H, dd, J=16.0, 5.9 Hz), 5.38–5.31 (2 H, m), 4.19 (1 H, q, J=5.6 Hz), 3.97 (2 H, t, J=7.3 Hz), 3.59 (2 H, t, J=6.3 Hz), 3.15 (2 H, d, J=4.4 Hz), 2.34 (2 H, t, J=7.5 Hz), 2.20–2.10 (2 H), 2.11 (3 H, s), 1.78–1.67 (4 H), 1.55–1.46 (4 H), 1.39–1.18 (10 H), 0.89–0.81 (12 H), 0.04 (3 H, s), 0.02 (3 H, s); $^{13}$C NMR (50 MHz, CDCl$_3$) δ 177.74, 145.86, 135.90, 134.15, 129.49, 128.33, 119.65, 115.10, 73.86, 62.43, 48.86, 38.33, 33.30, 32.26, 31.85, 30.28, 26.61, 26.08, 25.92, 25.02, 24.50, 22.64, 21.83, 18.28, 14.08, 9.49, −4.26, −4.80; mass spectrum m/z (M$^+$) calcd for C$_{31}$H$_{56}$N$_2$O$_4$Si 548.4009, found 548.3967.

3-(3-(tert-Butyldimethylsiloxy)-1-(E)-octenyl)-4-(6-carboxy-2(Z)-hexenyl)-5-methyl-1-(6-oxohexyl)pyrazole. The alcohol structure 83 (20 mg, 0.036 mmol) was dissolved in dichloromethane (4 mL) containing 4-A molecular sieves and 4-methylmorpholine N-oxide (6.3 mg, 0.054 mmol). Solid tetrapropylammonium perruthenate (2 mg, 0.015 equiv)) was then added under nitrogen and the resulting green mixture stirred at room temperature. After 1 h of stirring, TLC analysis showed a new spot ($R_f$=0.3) with 70% ethyl acetate in hexane. Evaporation and filtration (small pipette silica gel column) eluting with ethyl acetate removed all the inorganic material. Rotary evaporation gave a crude siloxy aldehyde (14 mg, 70% yield) as an oil. This crude product was used for the next reaction without further purification: $^1$H NMR (200 MHz, CDCl$_3$) δ 9.73 (t, 1 H, J=1.6 Hz), 6.40 (d, 1 H, J=16.0 Hz), 6.16 (dd, 1 H, J=16.08, 5.96 Hz), 5.34 (m, 2 H), 4.20 (m, 1 H), 3.96 (t, 2 H, J=7.45 Hz), 3.15 (d, 2 H, J=4.69 Hz), 2.39 (m, 4 H), 2.20 (m, 2 H), 2.11 (s, 3 H), 1.50 (m, 16 H), 0.88 (s, 9 H), 0.85 (t, 3 H, J=2.24 Hz), 0.042 (s, 3 H), 0.02 (s, 3 H). 4-(6-Carboxy-2 (Z)-hexenyl)-3-(3-hydroxy-1(E)-octenyl)-5-methyl-1-(6-oxohexyl)pyrazole (structure 91). The above TBDMS ether (14 mg, 0.025 mmol) was treated with concentrated aqueous hydro fluorine acid (0.16 mL, 49% v/v) and acetonitrile (0.34 mL) in a polyethylene vial. The desilylation was followed by TLC with ethyl acetate as developing solvent ($R_f$ of starting silyl ether 0.57, desilyated product 0.24). After 20 min, TLC analysis showed no starting material. The reaction mixture was diluted with water (1.5 mL), extracted with CHCl$_3$ (3×5 mL), and dried over anhydrous MgSO$_4$. Filtration and evaporation gave hydroxy aldehyde structure 91 as a slightly yellow oil. This could be purified by silica gel chromatography (pipette column) using ethyl acetate as the mobile phase to give structure 91 as a single spot by TLC analysis using ethyl acetate as developing solvent $R_f$=0.25 (9.6 mg, 87% yield): $^1$H NMR (200 MHz, CDCl$_3$) δ 9.76 (t, 1 H, J=1.6 Hz), 6.48 (d, 1 H, J=16.2 Hz), 6.19 (dd, 1 H, J=16.2, 5.99 Hz), 5.36 (m, 2 H), 4.22 (m, 1 H), 3.99 (t, 2 H, J=7.46 Hz), 3.16 (d, 2 H, J=4.71 Hz), 2.40 (m, 4 H), 2.24 (m, 2 H), 2.12 (s, 3 H), 1.50 (m, 16 H), 0.86 (t, 3 H, J=2.25 Hz); $^{13}$C NMR (75 MHz, CDCl$_3$) δ 202.45, 177.14, 145.60, 136.02, 133.09, 129.34, 128.57, 120.70, 115.49, 73.30, 52.67, 49.07, 48.82, 43.65, 37.19, 33.17, 31.79, 30.36, 26.46, 25.18, 24.44, 22.62, 21.69, 14.08, 9.57; mass spectrum m/z (M$^+$) calcd for C$_{25}$H$_{40}$N$_2$O$_4$ 432.2988, found 432.2899.

Reductive Alkylation of Poly-L-lysine with Aldehyde structure 91. Referring to FIG. 8C, poly-L-lysine (2.7 mg, 4 equiv based on unit base of lysine, $M_r$=55 000) and pyrazole aldehyde structure 91 (2 mg, 0.0046 mmol) were dissolved in methanol (0.4 mL). This solution became a little cloudy. After 5 min of stirring, sodium cyanoborohydride (1.0 mg) was quickly added at room temperature. When the addition was complete, the solution became clear. This solution was stirred for 2 h at room temperature. After 2 h, TLC analysis with ethyl acetate showed a new UV-active polar spot and the disappearance of structure 91 ($R_f$=0.24). The solution was transferred to a dialysis tube ($M_r$ cutoff 14 000, Spectrapor membrane tubing no. 2) and dialyzed twice against 10% water (250 mL) in methanol for 24 h. The absence of free hapten structure 91 in the polylysine conjugate structure 94 was confirmed by TLC with ethyl acetate as developing solvent. After dialysis and concentration of adduct by rotary evaporation, two product fractions were obtained. One (2.3 mg) is soluble in MeOH, the other (2.5 mg) is insoluble in MeOH but soluble in water.

Reductive Alkylation of Bovine Serum Albumin with Pyrazole Aldehyde structure 91. BSA (5.5 mg, 0.085 mmol) and structure 91 containing a small amount of the allylically tritiated derivative structure 91-t (4.4 mg, 10.2 mmol, specific activity 0.168 mCi/mmol, prepared from a mixture of structures 82 and 82t) were dissolved in a solution of water (1.6 mL) and methanol (450 μL), and the reaction mixture was stirred for 10 min at room temperature. Solid sodium cyanoborohydride (5 mg, 86 mmol) was added to the reaction mixture and stirring was continued for 6 h. The reaction mixture was then transferred to a dialysis tube and dialyzed against 500 mL of pH 7.4 PBS buffer for 36 h, changing the buffer every 12 h. After dialysis, a TLC analysis showed no starting aldehyde or sodium cyanoborohydride. The solvent was removed in vacuo and the residue, BSA adduct structure 95, was dissolved in PBS pH 7.4 (2.5 mL). Two 50 μL aliquots were counted (average dpm=4150) and the molar ratio of BSA:pyrazole (hapten) was calculated to be at least 1:6.6.

Reductive Alkylation of KLH with Pyrazole Aldehyde structure 91. A mixture of $^3$H-labeled structure 91t and unlabeled aldehyde structure 91 (4.4 mg, 0.010 mmol, specific activity=0.092 mCi/mmol) in MeOH (400 μL) was added to KLH (10.7 mg, 700 μL of a solution containing 15.3 mg KLH/mL PBS). The solution was stirred for 10 min, and then NaBH$_5$CN was added (5 mg, 0.80 mmol) and the reaction mixture was then stirred for 16 h. (Note: a minimum of organic solvent must be used to avoid the precipitation of the KLH from solution.) The entire reaction mixture was then placed in dialysis tubing ($M_r$ cutoff=12 000–14 000) and stirred in PBS (3×400 mL) for 48 h, replacing the PBS solution after 8 and 24 h. The dialyzed suspension was diluted to a total volume of 3 mL, and two aliquots (30 μL) were counted: 40% (0.0040 mmol) of the starting aldehyde structure 91 had been incorporated into the protein conjugate structure 96 as determined by a count of 3.72×10$^{-4}$ mCi for the entire mixture.

MDA-LDL

MDA-LDL was prepared according to the method described by W. Palinski et al., Arteriosclerosis 10: 325–335 (1990). Briefly, LDL was incubated for 3 h at 37° C. with 0.5M MDA at a constant ratio of 100 μL/mg of LDL. MDA (0.5M) was freshly generated from malonaldehyde bis dimethylacetal by acid hydrolysis: 88 μL malonaldehyde bis dimethylacetal was incubated with 12 μL 4N HCl and 400 μL H$_2$O at 37° C. for 10 min. The reaction was then stopped by adjusting the pH to 7.4 by the addition of 1N NaOH, and the volume was brought to 1 mL with distilled H$_2$O. After conjugation, MDA-LDL was extensively dialyzed against PBS to remove unreacted MDA.

HNE-LDL

HNE-LDL was prepared according to the method described by W. Palinski et al., Arteriosclerosis 10: 325–335 (1990). Briefly, with conjugation under reducing conditions, in order to eliminate the solvent, an aliquot of 4-HNE in CH$_2$Cl$_2$ was dried under nitrogen, was resolubilized in an equal volume of PBS (pH 9.0), and was exposed to vacuum for 5 min. LDL (2 mg) was added to and gently mixed with EDTA dissolved in PBS (pH 9.0), so that a 1 mL aliquot containing 2 mg/mL of LDL and 10 mg/mL of EDTA was obtained. Ten μL of 2M NaCNBH$_3$ and 5 μmol of 4-HNE were added, and the mixture was incubated at 37° C. for 24 h, followed by extensive dialysis against PBS containing 10 mg/mL EDTA to remove unconjugated 4-HNE. Conjugation of 4-HNE with LDL under non-reducing conditions was performed by the same procedure, except that NaCNBH$_3$ was omitted.

Low Level Tritiated Samples

Figure 10:
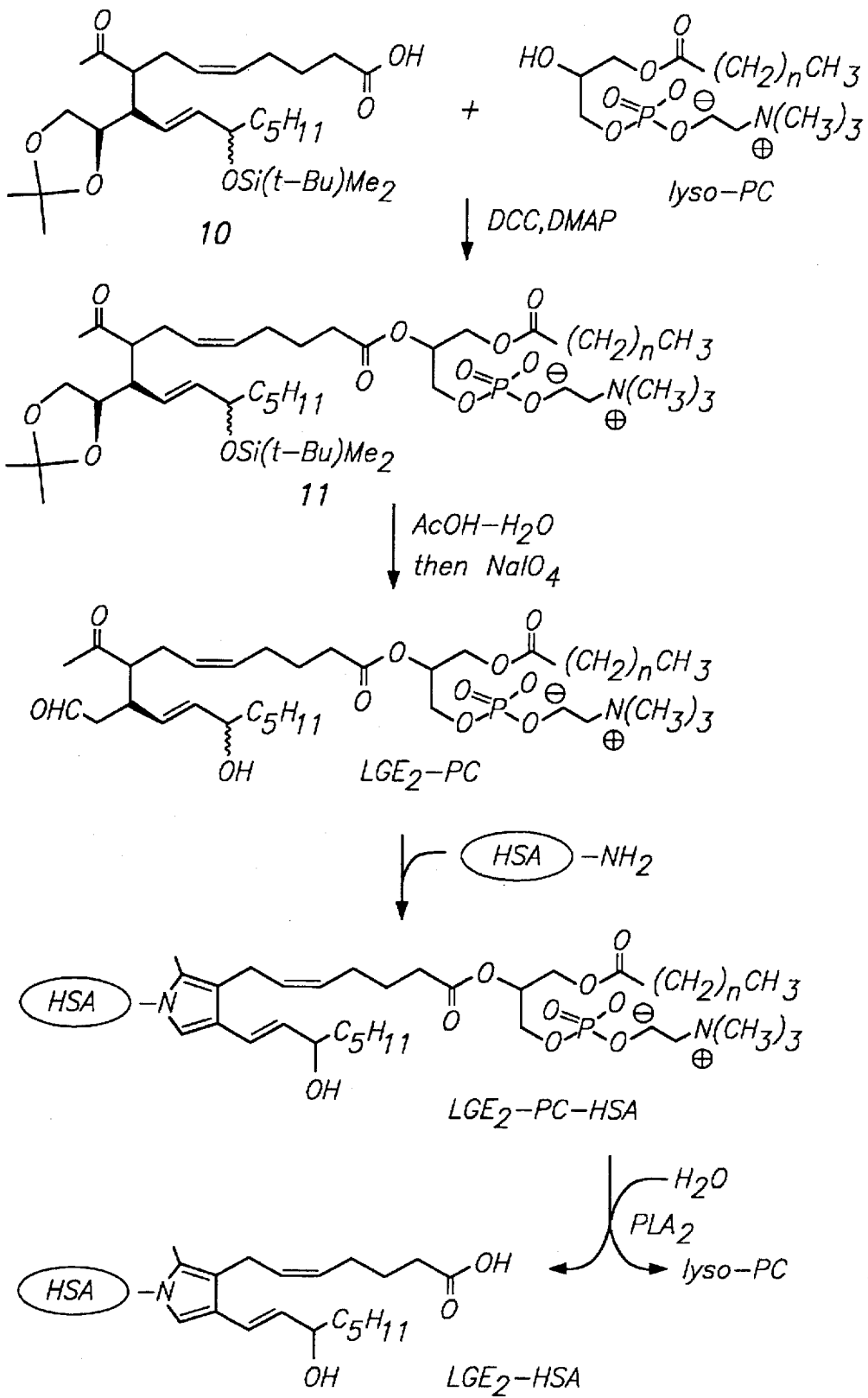
FIG. 10 is a schematic of the transformations involved in the synthesis of LGF$_2$-PC-HSA from structure 10. The numbers in parenthesis refer to structure numbers (discussed in the specification).

To allow quantitative radiochemical analysis, samples of lightly tritium-tagged LGE$_2$ precursor, 2-[8-acetyl-12-t-butyldimethylsiloxy-9-(1(S),2-isopropylidenedioxyethyl)-5 (Z),10(E)-heptandecadienoic acid, were prepared by adding small amounts of structure 10-t2 to structure 10 (see FIGS. 7 and 10). These mixtures are referred to as tritium-labeled structure 10. The specific activities of these samples were determined by weighing the sample and liquid scintillation counting of an aliquot. LGB$_2$ prepared from this precursor is referred to as "tritium labeled" LGB$_2$, and is presumed to have the same specific activity.

LGE$_2$-KLH

A PBS solution containing 28 mM tritium-labeled (45 μCi/mmol) LGE$_2$ (12.48 μmol) and 2.2 μM KLH (6.7 mg, 3.34 μmol of lysyl residues) was incubated at room temperature for 1 h followed by dialysis against PBS (200 mL for 8 h, then 200 mL for 16 h). The fraction of LG bound (17%) was determined by quantitative radiochemical analysis. The adduct solution was diluted to provide 0.72 mM KLH-bound LGE$_2$. [See E. DiFranco et al., Chem. Res. Toxicol. 8: 61–67 (1995)].

LGE$_2$-BSA

Tritium-labeled LGE$_2$ (specific activity 1.14 μCi/mmol, 16 mg, 46.8 μmol) was treated with HSA (33 mg) in pH 7.4 PBS (1000 μL). The mixture was stirred for 5 min at room temperature until it became homogenous. The resulting solution was incubated at 37° C. for 4 h, then transferred to a dialysis bag (MW cutoff 14000). The reaction product mixture, which mined light purple during incubation, was dialyzed against TBS (125 mL, 5 mM, pH 7.4). The dialysis bath was changed after 24 h with fresh TBS (125 mL). After dialysis for an additional 24 h period, the purple solution turned colorless.

The colorless solution was transferred into a vial and the volume was adjusted to 2 mL. An aliquot (100 μL) was added to scintillation cocktail (5 mL) and was counted for tritium disintegrations. The 100 μL aliquot gave 720 dpm that corresponds to 3.24×10$^{-10}$ Ci. Thus, the radioactivity for the entire sample was about 6.48×10$^{-9}$ Ci. This corresponds to 5.68 μmol of LGE$_2$ bound to HSA (by quantitative radiochemical analysis). The final concentration of HSA bound LGE$_2$ was thus 2.84 mM.

LGE$_2$-BSA

Tritium-labeled LGF$_2$ (specific activity 1.14 μCi/mmol, 16 mg, 46.8 μmol) was treated with BSA (66 mg) in PBS (2 mL, pH 7.4). The resulting mixture was stirred for 5 min at room temperature and then incubated at 37° C. for 4 h. The resulting mixture was transferred into a dialysis bag (MW cutoff 14000) and dialyzed against TBS (125 mL, pH 7.4). After 24 h, the dialysis bath was replaced with fresh TBS (125 mL). Following an additional 24 h dialysis period, the mixture was transferred into a conical vial and the volume was adjusted to 5 mL. An aliquot (100 μL) was mixed with scintillation cocktail (5 mL) and counted for tritium disintegrations. The 100 μl aliquot showed 531 dpm that corresponds to 2.39×10$^{-4}$ μCi. Therefore, the radioactivity for the entire sample was 1.20 μCi that corresponds to 10.4 μmol of LGE$_2$ bound to BSA. The final concentration of BSA-bound LGF$_2$ was thus about 2.08 mM.

2-[8-(R)-Acetyl-12-t-butyldimethylsiloxy-9-(1(S),2-isopropylidenedioxyethyl)-5(Z),10(E)-heptadecadienoyl]-1-palmitoyl Phosphatidylcholine (Structure 11; see Table 1)

To a flask containing L-1-palmitoyl lysophosphatidylcholine (50 mg, 0.1 mmol) and 2-[8-acetyl-12-t-butyldimethylsiloxy-9-(1(S),2-isopropylidenedioxyethyl)-5 (Z),10(E)-heptandecadienoic acid (structure 10, 158 mg, 0.30 mmol), toluene (2 mL) was added and was then evaporated under reduced pressure to azeotropically remove water from the reactant. This procedure was repeated twice, followed by removal of the last traces of water and toluene by evacuation overnight through a dry ice-acetone cooled trap at 0.1 mm Hg. The flask was then flushed with dry argon and DCC (64 mg. 0.30 mmol), DMAP (37 mg, 0.30 mmol) and CHCl$_3$ (6 mL) were added under a blanket of argon. The flask was covered with aluminum foil to prevent exposure to light. This mixture was stirred 24 h and was monitored by TLC (solvent system 70% CHCl$_3$ and 26% MeOH in water, visualized using 12). The reaction was stopped by removing solvent under reduced pressure followed by redissolving the residue in 10% MeOH in CHCl$_3$. This mixture was transferred onto a prep silica plate (0.5 mm thickness, 200 mm×200 mm), which was developed in 4% water and 26% MeOH in CHCl$_3$. A single UV active band corresponding to PC (R$_f$=0.32) was separated and extracted from the silica gel using 4% water and 26% MeOH in CHCl$_3$. The NMR showed the required product along with some other impurities. TLC of the NMR sample showed many less polar spots along with the major spot of PC, suggesting that the product was degrading on silica gel. This NMR sample was passed through a short alumina column that was first eluted with 10% MeOH in CHCl$_3$ to remove the less polar components followed by elution with 4% water and 26% MeOH in CHCl$_3$ to provide pure (single spot on TLC plates coated with alumina: R$_f$=0.48 in 4% H$_2$O and 26% MeOH in CHCl$_3$) phosphatidylcholine ester (structure 11).

The $^1$H NMR spectrum of this fraction showed clean ester product. NMR (300 MHz, CDCl$_3$) δ 5.55–5.16 (m, 4 H), 4.39–4.29 (m, 2 H), 4.39–3.80 (m, 11 H), 3.59–3.36 (m, 13 H), 2.71–2.48 (m, 1 H), 2.32–1.97 (m, 11 H), 1.60–1.14 (m, 41 H), 0.92–0.82 (m, 15 H), 0.01–0.03 (m, 6H). Elemental analysis: Calculated for C$_{55}$H$_{109}$NO$_{12}$PSi·3H$_2$O: C 61.65%, H 10.63%. Found: C 61.72%, H 9.55%.

Tritium-Labeled 2-[8-Acetyl-9-(12-t-butyldimethylsiloxy-1(S),2-isopropylidenedioxyethyl)-5(Z),10(E)-heptadecadienoyl]-1-palmitoyl Phosphatidylcholine (Tritium-Labeled Structure 11)

A mixture of structure 10-t2 (0.096 mg, specific activity 1.7 nCi/mmol) and unlabeled acid, structure 10 (428 mg), was prepared (see FIGS. 7 and 10). To a portion of the mixture (200 mg, 0.38 mmol) was added L-1-palmitoyl-2-lyso-phosphatidylcholine (62 mg, 0.12 mmol). The esterification reaction was carried out in the same manner as above for file unlabeled acid (structure 10). After stirring 24 h, the mixture was dissolved in 10% MeOH in $CHCl_3$ (2 mL), and water (1 mL) was added to this solution.

The resulting suspension was vigorously shaken and then centrifuged for 5 min at 1500 rpm. The lower organic layer was separated and the process was repeated two more times. The solvent from the combined organic phases was removed with a stream of $N_2$. Dry toluene (500 µL) was added to the residue and evaporated again under a stream of $N_2$. This process was repeated several times until no more water remained in the flask. The residue was purified by column chromatography on neutral alumina (activity 1, ID 10 mm, length 100 mm) pre-equilibrated with 10% MeOH in $CHCl_3$, eluting first with 10% MeOH in $CHCl_3$ followed by 4% water and 26% MeOH in $CHCl_3$ to obtain pure tritium-labeled $LGE_2$-PC precursor (structure 11) (38.5 mg, 33%); the pure tritium-labeled $LGE_2$-PC precursor (structure 11) appeared as a single spot by TLC analysis on alumina coated plates using 4% water and 26% MeOH in $CHCl_3$ as a solvent system. The specific activity of this sample of tritium-labeled structure 11 was 12.7 µCi/mmol according to quantitative radiochemical analysis.

2-$LGE_2$-1-palmitoyl Phosphatidylcholine ($LGE_2$-PC)

To a 5 mL round bottom flask was added tritium-labeled structure 11 (5 mg, 0.005 mmol) dissolved in $CHCl_3$ (130 µL). The chloroform was evaporated with a stream of $N_2$ and AcOH-water (2:1, v/v, 200 µL) was added followed by stirring for 90 min at 40° C. This mixture was then transferred into 30% aqueous acetone (250 µL). A solution of $NaIO_4$ (1.6 mg, 0.007 mmol) in 30% aqueous acetone (10 µL) was added. The resulting mixture was stirred 3 h at room temperature and then diluted with MeOH-$CHCl_3$ (1:9, v/v, 1 mL) and water (500 µL), and the mixture was vigorously stirred.

The resulting suspension was centrifuged 5 min at 1500 rpm. The lower organic phase was separated and the process was repeated two more times after addition of MeOH-$CHCl_3$ (1:9, v/v, 1 mL) to the remaining aqueous phase. The combined organic phases were concentrated under a stream of $N_2$. To the residue, toluene (500 µL) was added and then evaporated with a stream of $N_2$. This process was repeated until all the water in the flask was removed. The last traces of toluene were then removed from the residue by evacuation through a dry ice-acetone cooled trap at 0.1 mm Hg to obtain the $LGE_2$-PC ester (2.5 mg). The $LGE_2$-PC ester was immediately reacted with HSA, as described below.

$LGE_2$-PC-HSA $LGE_2$-PC (2.5 mg, 3.0 µmol) was treated with HSA (9.9 mg) in PBS (750 µL; pH 7.4). This mixture was stirred for 5 min at room temperature followed by incubation at 37° C. overnight. The resulting mixture was transferred to a dialysis bag (MW cutoff 14000) and dialyzed against PBS (125 mL; pH 7.4) for 48 h to remove the unreacted $LGE_2$-PC. The dialysis bath was changed after 24 h with fresh PBS (125 mL). After dialysis, the solution (650 µL) was transferred to a vial and the volume was adjusted to 1000 µL by addition of PBS (350 µL; pH 7.4). The amount of $LGE_2$-PC that is bound with HSA was determined by adding two aliquots (10 µL each) to scintillation cocktail (5 mL each) and counting the number of $^3H$ disintegrations. The average counts were 643 dpm. This is equivalent to $2.90\times10^{-10}$ Ci. Therefore, the radioactivity in the entire sample was $2.90\times10^{-8}$ Ci that corresponds to 2.28 µmol. The final concentration of the $LGE_2$-PC bound to protein was thus 2.28 mM.

Lipoproteins

Low density lipoprotein (LDL) was isolated from human plasma by sequential ultracentrifugation as a 1.019<d<1.063 g/ml fraction as described previously. [F. T. Hatch and R. S. Lees, Adv. Lipid Res. 6: 2–63 (1968)]. The LDL was dialyzed against NaCl (0.15M pH 8.5) containing 0.5 mM $Na_2EDTA$, filter-sterilized, and then stored at 4° C.

OxLDL: In Vitro Oxidation of LDL

LDL (500 µg/ml, 20 mL) was dialyzed at 5° C. for 5 h against PBS (4 L, pH 7.4), and then for 12 h against fresh buffer (4 L). Thereafter, LDL was dialyzed at 37° C. against 10 µM $CuSO_4$ in PBS (1 L, pH 7.4). Aliquots were removed periodically. The free radical oxidation reaction in each aliquot was stopped by adding $Na_2EDTA$ (1 mg/ml final concentration) and BHT (40 µM final concentration).

$LGE_2$-LDL

Unless stated otherwise, PBS (pH 7.4) used for reactions of LDL contained $Na_2EDTA$ (1 mg/mL) and BHT (50 µM). A solution of LDL (2940 µg/mL) in PBS (500 µL) was combined with tritium labeled (3.94 mCi/mmol) $LGE_2$ (0.002 mg, 5.7 nmol) in PBS (500 µL), and the mixture was incubated at 37° C. for 12 h. The mixture was then dialyzed against PBS (2×200 mL) over 36 h. After adjustment of the volume to 1.10 mL, quantitative radiochemical analysis revealed that the amount of $LGE_2$ bound to LDL was 30% of the $LGE_2$ added, and 157 pmol/mg of LDL of $LGE_2$-protein immunoreactivity was detected in the sample by ELISA (see below).

In a similar experiment that started with 0.1 mg (292 nmol) of $LGE_2$, the amount of $LGE_2$ bound to LDL was found to be 26.8% of the $LGE_2$ added, and 941 pmol/mg of LDL of $LGE_2$-protein immunoreactivity was detected in the sample by ELISA.

Human Plasma

Blood was collected in 7 mL vacutubes (purple top) which contain EDTA (10.5 mg). Cells were removed by centrifugation at 2500 rpm for 20–30 min. After transfer of the supernatant serum to a plastic vial, a solution of BHT (1 mg/mL) in absolute ethanol was added to give a final concentration of 1 µg/mL, and the serum was then stored at −20° C. for no more than a few days. For longer term storage, samples were kept at −70° C.

Immunization

The immunogen, an $LGE_2$-KLH adduct (1.12 mg) containing 0.32 µmol of $LGE_2$ per mg of KLH, was dissolved in PBS (500 mL, pH 7.4). The solution was emulsified in Freund's complete adjuvant (500 µL). Each of three Pasturella free, New Zealand white rabbits (Hazelton, Denver, Pa.) were inoculated intradermally (125 µL) into several sites on the back and intramuscularly in the rear leg (125 µL). Booster injections of $LGE_2$-KLH in Freund's incomplete adjuvant were given every 21 days. Antibody titre was monitored 10 days after each inoculation by ELISA as described below.

Antibody Purification

SEROCLEAR® (Calbiochem, La Jolla, Calif.) (1.4 mL) was added to crude antibody serum (1.4 mL) from the 94 day bleeding of rabbit number 3, and the mixture was vortexed for 60 seconds. The mixture was then centrifuged for 10 min at 3000 rpm and the upper delipidated layer (aqueous phase) was removed and added to an equal volume of binding buffer. This solution was eluted through a PROTEIN A SUPEROSE® (Pharmacia) column monitoring the eluant at 280 nm. The eluate was collected into fractions (1 mL) containing Tris buffer (160 µL, pH 8.8, 1.0M). The fractions containing IgG proteins were pooled and dialyzed against PBS (ph 7.4, 0.02% $NAN_3$) for 24 h at 5° C. The concentration of purified IgGs in the resulting solution, 0.935 mg/mL, was determined by measuring absorbance at 280 nm. This corresponds to about one-fifth of the IgG concentration in the crude serum.

III. EXAMPLES

Example 1

ELISA—Measurement of Epitopes on Proteins Characteristic for Oxidative Events

This example involves the development and use of an ELISA for measuring epitopes on proteins that are characteristic for oxidative events. The materials and procedures that follow are specific for this particular ELISA unless otherwise indicated.

Materials

1. Plates IMMULON® 3 REMOVAWELL® Strips (Dynatech Labs; Chantlily, Va.)
2. 20 mM PBS: 20 mM $NaPO_4$, 150 mM NaCl, 0.3 mM EDTA. pH 7.4 (The $PO_4$ buffer and the saline EDTA can be stored as 10× stock solutions).
3. Coating Buffer: 10 mM $NaHCO_3$ (9 parts), 10 mM $Na_2CO_3$ (1 part) pH 9.6
4. Blocking Buffer: 3% BSA/PBS with 0.2% NaAzide
5. Diluent: 1% BSA in PBS; 0.1% Triton×705; 0.1% Azide
6. Wash Buffer: 20 mM PBS; 0.1% Triton×705; 0.1% Azide Procedure 1. Bind unlabeled IgG fraction of anti human apo B or apo(a) to the bottom of each well by adding 50 µL of antibody (Ab) solution (3 µg/mL in coating buffer). Incubate overnight at cold temperature (4° C.).
2. Wash the wells twice with the washing buffer, 100 µL/well.
3. The remaining sites for protein binding on the wells must be saturated by incubating with 200 µL of blocking buffer. Incubate for 2 h overnight at room temperature (RT).
4. Wash the wells twice with the washing buffer, 100 µL/well. Plates can be stored for one week at (4° C.) in a sealed plastic container (e.g., TUPPERWARE® or RUBBERMAID®) lined with moist paper towels. Plates must not be allowed to dry out.
5. For generating a standard curve, add 50 µL of antigen solutions (LDL-LG or Lp(a)-LG serially diluted in diluent). For unknowns, 50 µL/well of 1-to-100 dilution of plasma in diluent. Incubate for at least 2 h at RT.
6. Wash the plate four times with 100 µL/well of washing buffer.
7. When the specific detecting antibody (Ab) is from a different species than that of the mobilized Ab (e.g., mobilized Ab is from goat; detecting Ab is from rabbit) neat (undiluted) serum is used and an $^{125}$I-labeled IgG fraction of goat anti-rabbit IgG is used for quantification. This has the advantage of isolating IgG only once and labeling only once. However, if the same species is used, an IgG fraction of the detecting Ab is iodinated and used. 100 µL/well of a predetermined dilution of anti-human apo(a), anti-human apo B, or anti-LG is added to each well. Incubation is performed for at least 2 h at room temperature. The levels of apo (a), apo B, and LG-protein are quantified with the appropriate detecting antibody. This allowed the normalization of LG-protein per molecule of Lp(a) and LDL.
8. Wash four times with washing buffer 100 µL/well.
9. When detecting Abs are labeled, wells are separated and counted.
10. When labeled anti-IgG is used, 50 µL of a predetermined dilution is added to each well and incubated for at least 2 h at RT.
11. Wash four times with washing buffer (100 µL/well), separate wells, and count.

By using this ELISA procedure, one is able to measure epitopes on proteins that are characteristic for oxidative events.

Example 2

ELISA—Antibody Titres

For determination of antibody levels in rabbit blood serum, the BSA conjugate of a stable pyrazole isostere [M. E. Kobierski et al., J. Org. Chem. 59: 6044–50 (1994)] of levuglandin-derived protein-bound pyrroles (structure 4; see Table 1) was used as coating agent. The pyrazole isostere hapten was conjugated with BSA in a 6.6:1 molar ratio. The isostere-BSA conjugate (100 µL of a solution containing 4.4 mg/mL in pH 7.4 PBS) was added to each well of a sterilized Baxter ELISA plate. The plate was then incubated at 37° C. for 1 h in a moist chamber. After discarding the coating solution, each well was washed with PBS (3×300 µL), then filled with 1.0% chicken ovalbumin (OA) in PBS (300 µL) and incubated at 37° C. for 1 h to block remaining active sites on the plastic (immobilized) phase. After washing each well with 0.1% OA in PBS (300 µL), 100 µL of rabbit serum from each bleeding, diluted 1:100, 000 with 0.2 % OA in PBS or 0.2% OA in PBS without serum for a blank, was dispensed into the sample wells. Normal rabbit (i.e., not injected with antigen) serum diluted as above was employed as a negative response control.

Figure 9:
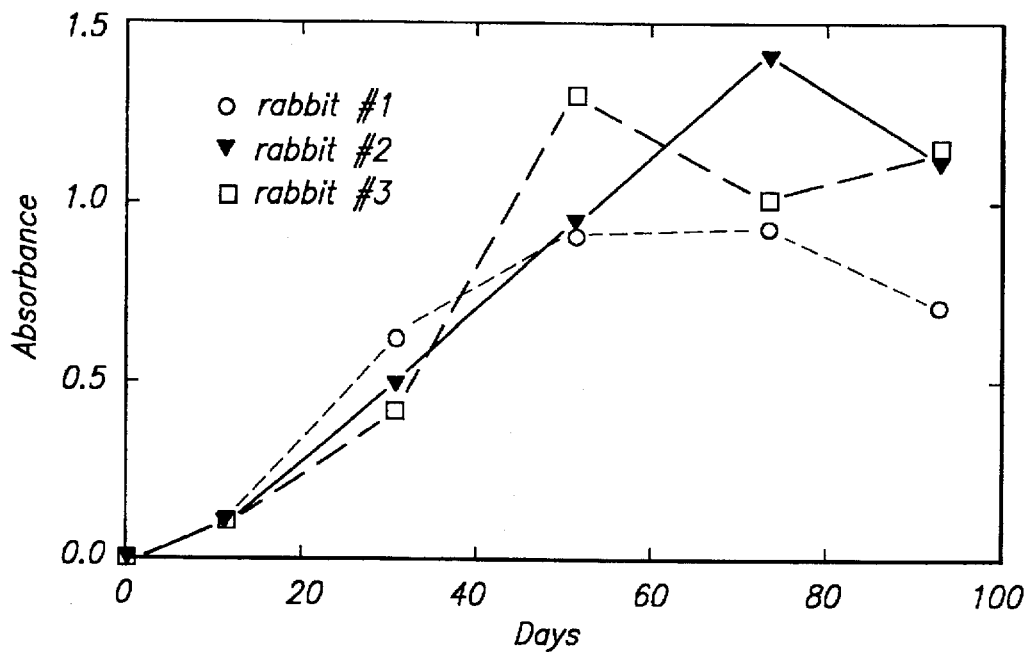
FIG. 9 graphically depicts antibody titre levels in rabbit blood serum.

The plate was covered and incubated at room temperature for 1 h with shaking. After discarding the supernatant and washing with 0.1% OA (3×300 µL), 100 µL of goat anti-rabbit IgG-alkaline phosphatase, diluted 1:1000 with 1.0 % OA, was added to each well; the plate was again incubated with shaking at room temperature for 1 h. After discarding the supernatant, the wells were washed with 0.1% OA (3×300 µL). Enzyme-linked antibody bound to the well was revealed by dispensing into each well 100 µL of disodium p-nitrophenyl phosphate (10 mg) in a solution (11 mL, pH 9.6) containing glycine (50 mM), $MgCl_2$ (1 mM), and sufficient 6M NaOH to raise the pH to 9.6. The plate was allowed to develop at room temperature until the maximum absorbance was judged appropriate, usually less than 20 min. Sample absorbances were then measured using dual wavelength on a Bio-Rad 450 Microplate reader. The antibody titre levels for each of the three rabbits tested are set forth in FIG. 9.

Example 3

ELISA—Competitive Antibody Binding Inhibition Studies

For antibody binding inhibition studies to measure cross-reactivities, an $LGE_2$-BSA adduct was used as coating agent and $LGE_2$-HSA was used as standard. For each inhibitor, a blank, up to ten serial dilutions, and a positive control containing no inhibitor were run. On each ELISA plate, LGE$_2$-HSA was run as a standard for quantification of LGE$_2$-protein adducts. The standard was prepared by diluting a PBS solution containing 2.84 mM HSA-bound LGE$_2$ to 0.42 mM with TB8 (pH 7.4). Each well of the plate was coated with LGE$_2$-BSA solution (100 µL), prepared by diluting a PBS solution containing 2.08 mM BSA-bound LGE$_2$ to 94.5 nM with TBS (pH 7.4). The plate was covered with a plastic lid and placed in incubator at 37° C. for 1 h, and then allowed to come to room temperature. After discarding the supernatant, each well was washed with TBS (3×300 µL, pH 7.4) and then blocked by incubating 1 h at 37° C. with 300 µL of 1% chicken egg ovalbumin (CEO) in pH 7.4 TBS (pH 7.4).

After coming to room temperature, the supernatant was discarded and the wells were rinsed with 0.1% CEO in TBS (300 µL, pH 7.4). For each sample and the LGE$_2$-HSA standard, the undiluted sample solution (150 mL) and aliquots (150 mL) of up to nine 1:10 serial dilutions with 5 mM TBS (pH 7.4) were incubated in test tubes at 37° C. for 1 h with antibody solution (150 µL). The antibody solution was prepared by adding the required amount of FPLC-purified (protein A column) antibody (910 µg/mL in pH 7.4 PBS) to 0.2% CEO in TBS (pH 7.4, 5 µL/10 mL of 2% CEO, different dilutions of the purified antibody serum were used as indicated for the specific assay, see below).

Blank wells were filled with a 0.2% CEO in TBS (100 µL, pH 7.4). Positive control wells were filled with the antibody solution (50 µL) and 0.2% CEO solution (50 µL). To the rest of the sample wells, aliquots (100 µL, containing 50 µL of sample solution and 50 µL of antibody solution) of the serial dilutions of antibody-antigen complex were added. The plate was then incubated at room temperature on a shaker for 1 h. After discarding the supernatant, the wells were washed with 0.1% CEO (3×300 µL), and then goat anti-rabbit IgG-alkaline phosphatase solution (100 µL) was added to each well. This enzyme-linked second antibody solution was prepared by diluting commercially-available antibody solution (10 µL) with 1% CEO (10 mL). The plate was then incubated at room temperature for 1 h while gently agitating on a shaker. After discarding the supernatant, the wells were washed with 0.1% CEO (3×300 µL). To each well was then added a solution (100 µL) of disodium p-nitrophenyl phosphate (10 mg) in water (11 mL, pH adjusted to 9.6 using NaOH) containing glycine (50 mM) and MgCl$_2$ (1 mM). The plate was then incubated at room temperature for about 1 h until the absorbance levels reached an appropriate level. The absorbance in each well was measured with a Bio-Rad 450 Microplate reader using dual wavelength.

Absorbance values for duplicate assays were averaged and then scaled such that the maximum curve fit value is close to 100 percent. The averaged and scaled percent absorbance values were plotted against the log of concentration. Theoretical curves shown for each plot were fit to the absorbance data with a four parameter logistic function, $f(x)=(a-d)/[1+(x/c)^b]+d$ using SIGMAPLOT® 4.14 from Jandel Scientific Software, San Rafael, Calif. Parameter a=the asymptotic maximum absorbance, b=slope at the inflexion point, c=the inhibitor concentration at the 50% absorbance value (IC$_{50}$, reported in Table 2), and d=the asymptotic minimum absorbance. If necessary, constraints were placed on the parameters, usually the values for "a" and/or "d". A Cartesian graph was then created that shows plots of the experimental data (points) and calculated curves.

Example 4

ELISA—Cross-Reactivity Of LGE$_2$-PC-HSA With LGE$_2$-KLH Antibodies

This example analyzes whether LGE$_2$-KLH antibodies cross-react with LGE$_2$-derived pyrrole phospholipids (structure 3; see Table 1). In this example, LGE$_2$-PC-HSA was synthesized according to the procedure outlined in FIG. 10 and examined for cross-reactivity with LGE$_2$-KLH antibodies. Due to the proclivity of LGE$_2$ toward dehydration, L-α-palmitoyl lysophosphatidylcholine (lyso-PC) was esterified with a stable precursor of LGE$_2$, 2-[8-acetyl-9-(1-(S),2-isopropylidenedioxyethyl)]-12-t-butyldimethylsiloxy-5(Z),10(E)-heptanedecadienoic acid (structure 10). [D. B. Miller et al., J. Org. Chem. 55: 3164 (1990)]. As depicted in FIG. 10, a series of transformations, previously exploited to prepare LGE$_2$ from structure 10, were used to convert this ester to the required LGE$_2$-PC-HSA. Coupling of the acid (structure 10) to lyso-PC was carried out in CHCl$_3$ using DCC and DMAP. [N. Hébert et al., J. Org. Chem. 57: 1777–83 (1992)]. Initial attempts to purify LGF$_2$-PC failed because of degradation of the product on silica gel during flash chromatography; this problem was circumvented by using alumina (Beckman activity 1) instead of silica gel as stationary phase. Alumina was pre-equilibrated with 10% MeOH in CHCl$_3$ prior to chromatography of crude product on the column. Pure structure 11 was obtained in modest yield (33%).

Thereafter, structure 11 was converted to LGE$_2$-PC by a sequence of reactions closely analogous to that used to prepare LGE$_2$ methyl ester. [D. B. Miller et al., J. Org. Chem. 55: 3164 (1990)]. Due to the presumed instability of LGE$_2$-PC, it was coupled immediately with a protein, human serum albumin (HSA). Incubation of LGE$_2$-PC with HSA in PBS (pH 7.4) overnight at 37° C. followed by dialysis to remove any unbound LGE$_2$-PC and low-molecular weight byproducts resulted in binding of LGE$_2$-PC to protein. The extent of binding, as determined by quantitative radiochemical analysis, was 0.23 µmol/mg of protein.

For the ELISAs, LGE$_2$-BSA (100 µL per well, 0.37 mM in 5 mM pH 7.4 TBS) was used as coating agent. An antibody solution was prepared by diluting an aliquot of affinity purified antibody (12 µL of 910 µg/mL in pH 7.4 PBS) to 10 mL with 0.2% CEO in TBS (pH 7.4). A standard, LGE$_2$-HSA in two different buffers, LGE$_2$-PC-HSA and LGE$_2$-PC-HSA after hydrolysis with PLA$_2$, were analyzed on the same plate using a serial dilution factor of 1:10 and the ELISA protocol outlined in Example 3. LGE$_2$-HSA (50 µL of 0.42 mM in 5 mM pH 7.4 TBS) was used as a standard for comparison with LGE$_2$-PC-HSA in the same buffer. This corresponds to 21000 pmol in the first well for the initial concentration of standard. A second standard was prepared by mixing the above LGE$_2$-HSA solution (300 µL, 0.42 mM) with snake venom PLA$_2$ (12 units in 12 µL of 5 mM pH 7.4 TBS). To this solution was added 1% T×100 in 5 mM TBS (6.2 µL, pH 7.4). The solution was vortexed briefly and then incubated at 37° C. simultaneously with the LGE$_2$-PC-HSA hydrolysis reaction mixture (discussed above). The resulting solution (50 µL, 0.39 mM) was used as the initial concentration, i.e., 19500 pmol of LGE$_2$-HSA standard in the first well. A solution of LGE$_2$-PC-HSA (16.4 µL, 2.28 mM in 5 mM pH 7.4 TBS) was diluted to 1000 µL with TBS (pH 7.4). This solution (50 µL of 37.3 µM) was used as the initial concentration of LGE$_2$-PC-HSA, i.e., 1869 pmol in the first well. A solution of LGE$_2$-PC-HSA (16.4 µL, 2.28 mM in 5 mM pH 7.4 TBS) was diluted to 1000 µL with pH 7.4 TBS. This solution (300 µL, 37.3 µM) was combined with snake venom PLA$_2$ (12 units dissolved in 12 µL 5 mM pH 7.4 TBS) and 1% T×100 in 5 mM pH 7.4 TBS (6.2 µL). The mixture produced was vortexed briefly followed by overnight incubation at 37° C. The resulting solution (50 µL of 35.2 µM) was used as the initial concentration, i.e., 1755 pmol in the first well for hydrolyzed LGE$_2$-PC-HSA.

As an estimate of the precision of the analyses, an average error was calculated for each data set by averaging the differences in the paired absorbance values for each concentration. The average errors were: $LGE_2$-HSA±=0.002, $LGE_2$-PC-HSA±=0.01, $LGF_2$-PC-HSA+$PLA_2$ (snake venom)+T×100±=0.008, $LGE_2$-HSA+$PLA_2$ (snake venom) +T×100±0.009.

Figure 11:
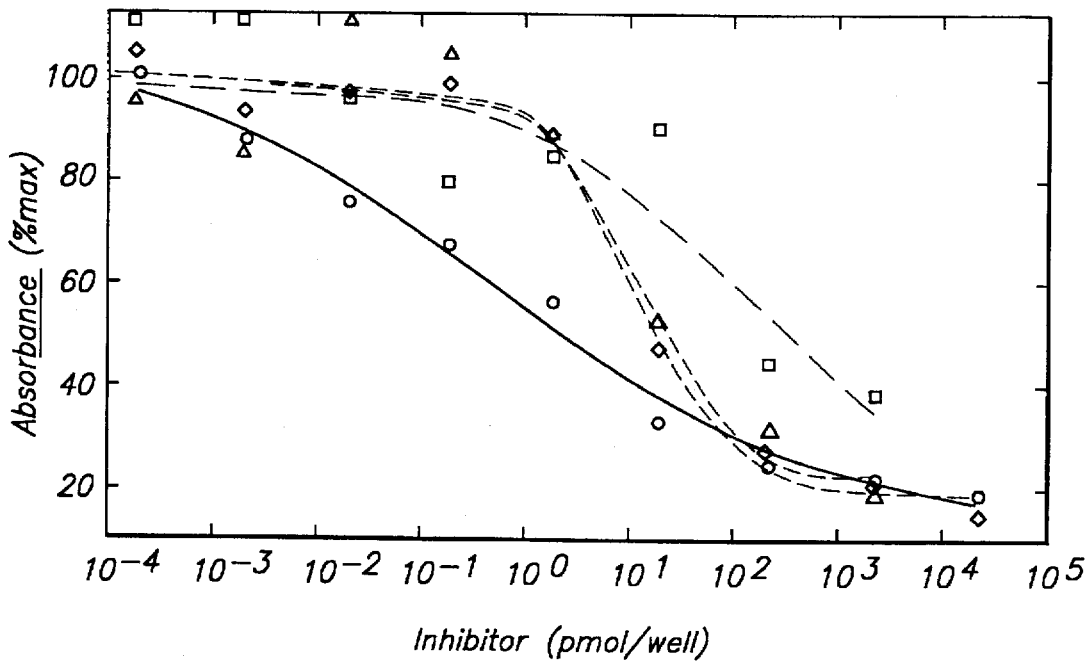
FIG. 11 graphically depicts ELISA inhibition curves for LGE$_2$-HSA (O), LGE$_2$-PC-HSA (□), LGE$_2$-PC-HSA after treatment with snake venom PLA$_2$ in the presence of 0.02% T×100 (△), and LGE$_2$-HSA in the presence of snake venom PLA$_2$ and 0.02% T×100 (◊).

The cross reactivity of $LGE_2$-PC-HSA with antibodies raised against an $LGE_2$-KLH adduct was determined, relative to $LGE_2$-HSA as a standard, by ELISA. FIG. 11 graphically depicts ELISA inhibition curves for $LGE_2$-HSA (O), $LGF_{-2}$-PC-HSA (□), $LGE_2$-PC-HSA after treatment with snake venom $PLA_2$ in the presence of 0.02% T×100 (Δ), and $LGE_2$-HSA in the presence of snake venom $PLA_2$ and 0.02% T×100 (◊). It is possible that the 0.5% cross-reactivity observed (FIG. 11), may be exaggerated due to the presence of a tiny mount of $LGF_{-2}$-HSA that was produced by hydrolysis of the phospholipid; thus, one can conclude that the cross-reactivity is no more than 0.5% and is probably less. This result was expected because the prostanoid side-chains are important for antigen recognition, and because the carboxylic side-chain is camouflaged by esterification with 2-lyso-phosphatidylcholine.

As indicated in FIG. 11, hydrolysis of $LGE_2$-PC-HSA was performed using the enzyme phospholipase A2 (from *Crotalus adamanteus*) in the presence of Triton X 100 (T×100). [M. A. Wells and D. J. Hanahan in Meth. Enzymol. (J. M. Lowenstein, ed.) 14: 178–84 (1969)]. The phosphate buffer (pH 7.4) in which the $LGE_2$-PC-HSA adduct had been prepared was replaced with Tris buffer (pH 7.4) because the enzyme would be deactivated by phosphate. In addition, calcium is required as a cofactor for $PLA_2$. Therefore, the solution of $LGE_2$-PC-HSA in phosphate buffer (pH 7.4) was dialyzed against Tris buffer solution (TBS, pH 7.4) containing 1 mM NaCl and 0.6 mM $CaCl_2$. Overnight incubation of dialyzed $LGE_2$-PC-HSA in TBS with $PLA_2$ and 0.02% T×100 was expected to completely hydrolyze the ester linkage, releasing 2-lyso-PC and generating $LGE_2$-HSA. Because T×100 strongly influences antibody binding, as evidenced by a noticeable difference in the slope of the inhibition curve, a mixture of $LGE_2$-HSA, $PLA_2$ and T×100 was used as a standard. The $IC_{50}$ for this standard was 13.4 pmol/well as compared to 0.8 pmol/well in the absence of T×100 (FIG. 11). This is identical to the $IC_{50}$ obtained for $LGE_2$-PC-HSA after treatment with $PLA_2$ (13.4 pmol/well, FIG. 11), and much lower than the $IC_{50}$ of $LGE_2$-PC-HSA before hydrolysis (167.5 pmol, FIG. 11). Thus, the cross-reactivity of $LGE_2$-PC-HSA before treatment with $PLA_2$ is 0.5% (relative to $LGE_2$-HSA) as compared to 100% after enzymatic hydrolysis (the cross reactivity of $LGE_2$-PC-HSA after treatment with $PLA_2$ in the presence of T×100 was measured relative to $LGE_2$-HSA in the presence of 0.02% T×100 and $PLA_2$).

Example 5

Figure 12:
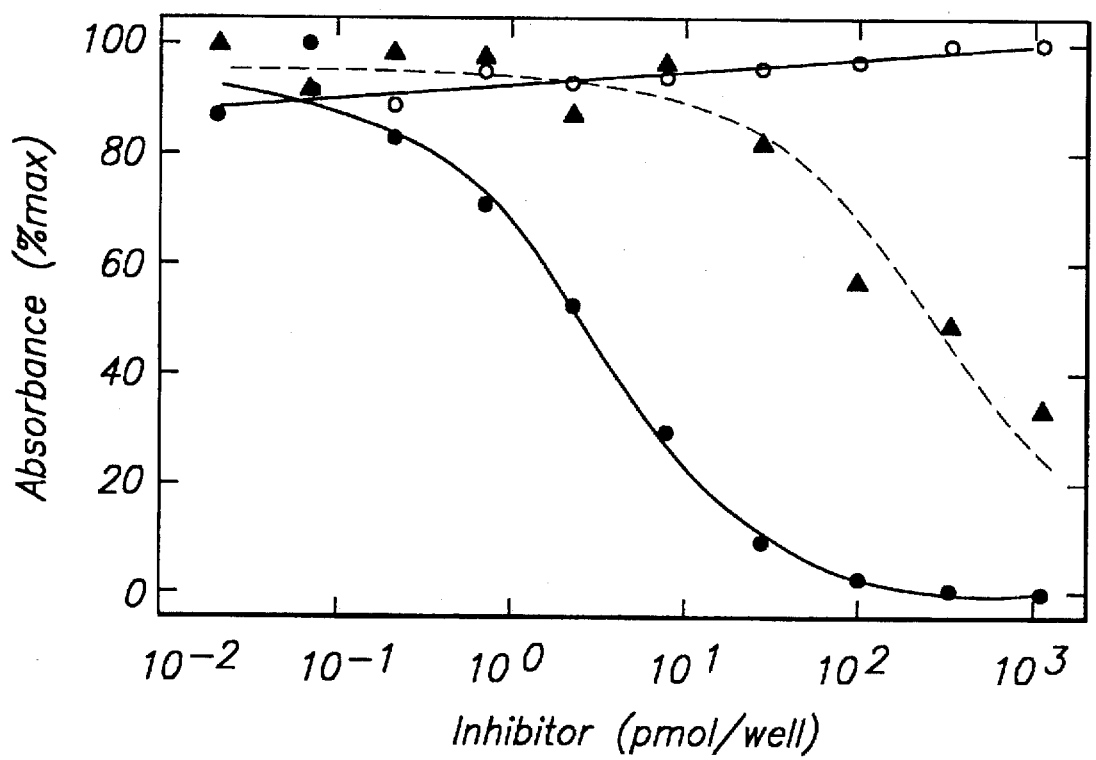
FIG. 12 graphically depicts ELISA detection of LG-protein adducts. Concentrations refer to protein-bound LGE$_2$ in an HSA adduct (●) as determined by quantitative radiochemical analysis with tritiated LG. All samples were analyzed with an identical series of dilutions. oxLDL (▲) was prepared in vitro by treatment of native LDL (O) for 3 h with Cu$^{+2}$ followed by addition of EDTA and BHT.

ELISA—LG-pyrrole Immunoreactivity in oxLDL and $LGE_2$-LDL In Vitro and LG-pyrrole Immunoreactivity in Human Plasma ELISA of oxLDL and $LGE_2$-LDL in vitro, as well as serum from normal, coronary artery bypass graft (CABG) and continuous ambulatory peritoneal dialysis (CAPD) human donors were performed in the same manner as the inhibition assays, except a dilution factor of 0.3 was employed and no duplicates were run. For determining the time-dependence of appearance of protein-bound pyrrole during the oxidation of LDL, protein concentration in each aliquot of oxLDL was measured using the Pierce bicinchonic acid (BCA) assay. [P. K. Smith et al., Anal. Biochem. 150: 76–85 (1985); BCA Protein Assay Reagent Instructions, Pierce, Rockford, Ill.]. Immunoreactivity per mg of protein was than calculated. The results are presented in FIG. 12, which graphically depicts ELISA detection of LG-protein adducts. In FIG. 12, concentrations refer to protein-bound $LGE_2$ in an HSA adduct (●) as determined by quantitative radiochemical analysis with tritiated LG. All samples were analyzed with an identical series of dilutions. oxLDL (▲) was prepared in vitro by treatment of native LDL (0) for 3 h with $Cu^{+2}$ followed by addition of EDTA and BHT.

In control experiments to remove any non-protein-bound antigens, oxLDL, CABG and CAPD plasmas (500 μl each) were dialyzed for 36 h at room temperature against PBS (2×200 mL, pH 7.4) containing $Na_2$EDTA (1 mg/mL) and BHT (50 μM). Then ELISA was performed for dialyzed and undialyzed samples on the same plate.

Another control experiment was run to demonstrate that 8-epi-$PGF_{2\alpha}$ is removed from LDL by dialysis. Thus, a solution of 8-epi $PGF_{2\alpha}$ (0.484 mL, 0.293 mg/ml) was mixed with 500 μL of LDL solution (2.94 mg/mL), and the volume was adjusted to 1 mL with PBS (pH 7.4) containing $Na_2$EDTA (1 mg/mL) and BHT (50 μM). This solution (500 μL) was dialyzed for 36 h at room temperature with PBS (2×500 mL). Thereafter, ELISA was performed on native LDL, undialyzed, and dialyzed samples.

It is believed that atherogenesis involves transcytosis of monocytes and LDL from the circulating plasma, through lesion-prone areas of the endothelium into the subendothelial space of arterial walls; the LDLs are oxidatively modified in the sub endothelial space. The resulting oxLDL is taken up by monocyte-derived macrophages, in an unregulated manner partially via the scavenger receptor, leading to foam cell formation. Ultimately, oxLDL-induced cytotoxicity results in foam cell necrosis and extracellular release of foam cell lipids. Because intravenously administered oxLDL is rapidly captured by the liver, it was presumed that plasma contains little or no oxLDL. [D. Steinberg et al., Arteriosclerosis 7: 135 (1987)]. However, more recent studies claim to have isolated oxLDL from the plasma of normal individuals. [P. Avogaro et al., Arteriosclerosis 8: 79 (1988)]. Furthermore, human serum contains auto-antibodies against epitopes on oxLDL, but not on native LDL. [W. Palinski et al., Proc. Natl. Acad. Sci. USA 86: 1372–76 (1989); J. T. Salonen et al., Lancet 339: 883–87 (1992)].

Figure 13:
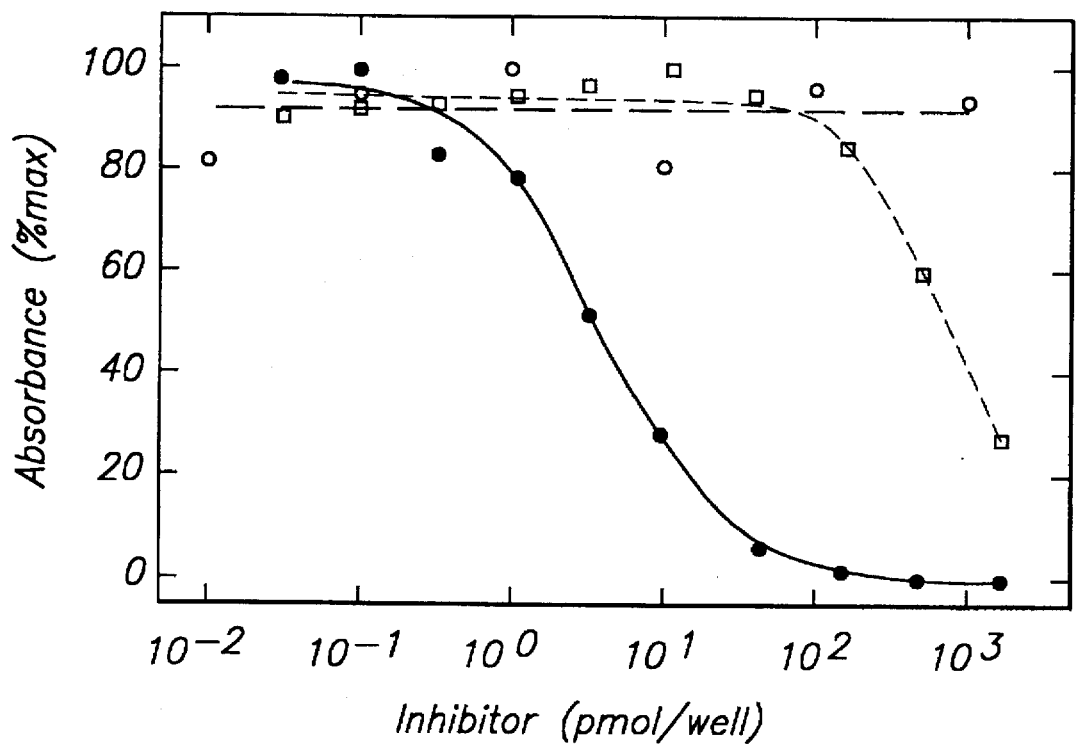
FIG. 13 graphically illustrates ELISA detection of LG-protein adduct immunoreactivity in human plasma. Concentrations refer to protein-bound LGE$_2$ in an HSA adduct (●). All samples were analyzed with an identical series of dilutions. Atherosclerosis plasma (□) was obtained by addition of EDTA and BHT to freshly drawn blood followed by centrifugation. The ELISA of a sample of native HSA (O) with the same protein concentration as the LG-HSA sample is also shown as an example of a non-immunoreactive protein.
Figure 14:
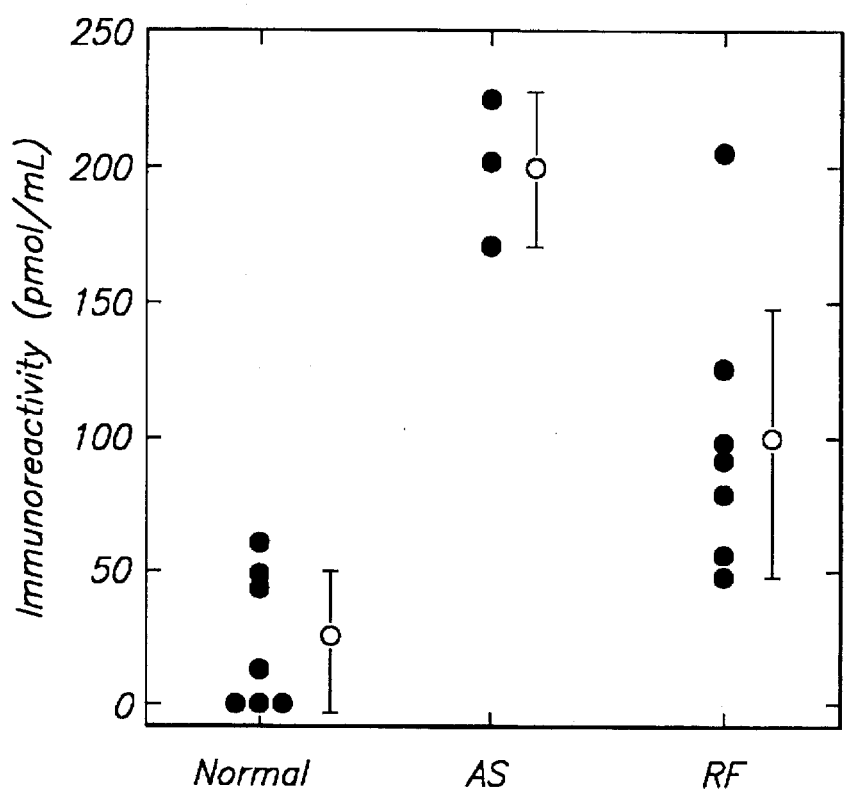
FIG. 14 diagrammatically illustrates levels of LG-protein adduct immuno-reactivity (●) detected in human plasma from healthy volunteers (normal), coronary artery bypass patients with atherosclerosis (AS) and peritoneal dialysis patients who have had renal failure (RF). The figure also shows mean levels detected (O). The error bars indicate the standard deviation for each data set.

Because the $LGE_2$-KLH antibodies recognize oxLDL but not native LDL (See FIG. 12), the possibility that such immunoreactivity might be detected in human plasma was investigated. FIG. 13 shows a typical inhibition curve obtained from the plasma of an atherosclerosis patient; of note, the slope is very similar to that of the $LGE_2$-HSA standard. In FIG. 13, which graphically depicts ELISA detection of LG-protein adduct immunoreactivity in human plasma, concentrations refer to protein-bound $LGE_2$ in an HSA adduct (●). All samples were analyzed with an identical series of dilutions. Atherosclerosis plasma (□) was obtained by addition of EDTA and BHT to freshly drawn blood followed by centrifugation. The ELISA of a sample of native HSA (O) with the same protein concentration as the LG-HSA sample is also shown as an example of a non-immunoreactive protein. The levels of immunoreactivity detected in a clinical pilot study in the plasma of healthy volunteers, coronary artery bypass patients with atherosclerosis (AS), and continuous ambulatory peritoneal dialysis patients who have suffered renal failure (RF) are summarized in FIG. 14. The figure also shows mean levels detected (O). The error bars indicate the standard deviation for each data set. In these data, the mean levels of immunoreactivity detected in the plasma of atherosclerosis (201 pmol/mL) and renal failure (100 pmol/mL) patients are elevated compared to healthy volunteers (24 pmol/mL). These observations suggest that LG-protein adducts are produced in vivo and that they are associated with oxidative injury.

Example 6

Figure 15A:
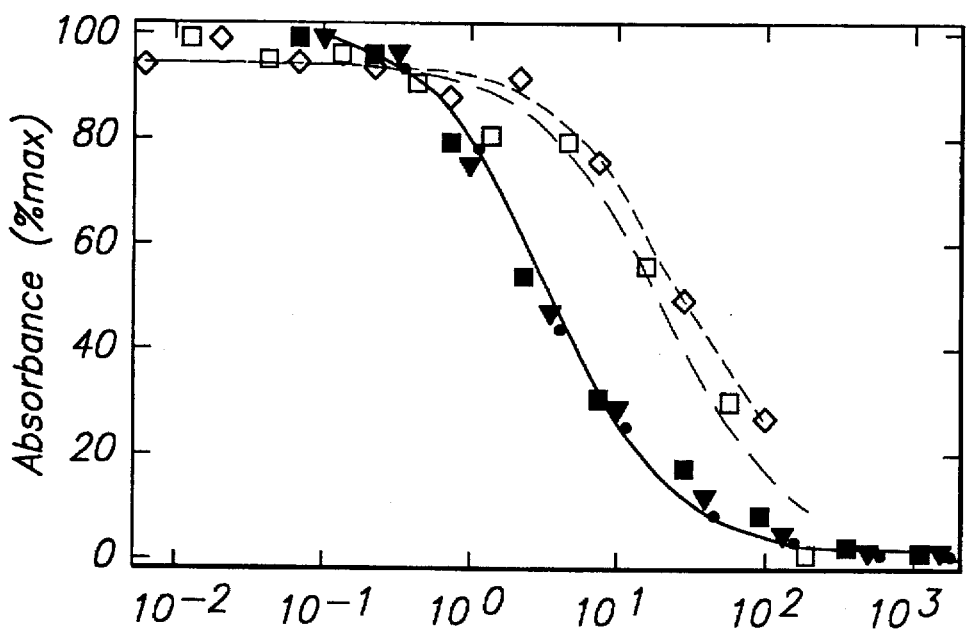
FIG. 15A graphically depicts antibody-binding inhibition by 0.5 mg/mL LG-HSA (●), and 0.5 mg/mL LG-LDL containing 1.9 µM (◊), 3.7 µM (□), 22 µM (■), or 30 µM (▲) protein-bound LG. Calculated curves are shown for LG-HSA and LG-LDL containing 1.9 µM or 3.7 µM protein-bound LG.

Yield of LGE$_2$-Protein Adduct Immunoreactivity Varies With Level of Adduction To provide calibration standards, samples of LG-LDL containing different levels of bound LG were prepared and their immunoreactivity was determined by ELISA. With 0.5 mg/mL LDL, the level of immunoreactivity produced, the IC$_{50}$ and the slope of the binding inhibition curves were identical for the LG-HSA standard and LG-LDL samples containing 22 or 30 µM protein bound LG, as measured by quantitative radiochemical analysis using tritium labeled LG (FIG. 15A). However, although the slopes of the binding inhibition curves continue to parallel that of the standard, the apparent IC$_{50}$ increases for samples containing lower levels of protein-bound LG, i.e., 1.9 or 3.7 µM. FIG. 15A graphically depicts antibody-binding inhibition by 0.5 mg/mL LG-HSA (●), and 0.5 mg/mL LG-LDL containing 1.9 µM (◊), 3.7 µM (□), 22 µM (■), or 30 µM (♦) protein-bound LG. Calculated curves are shown for LG-HSA and LG-LDL containing 1.9 µM or 3.7 µM protein-bound LG.

Figure 16:
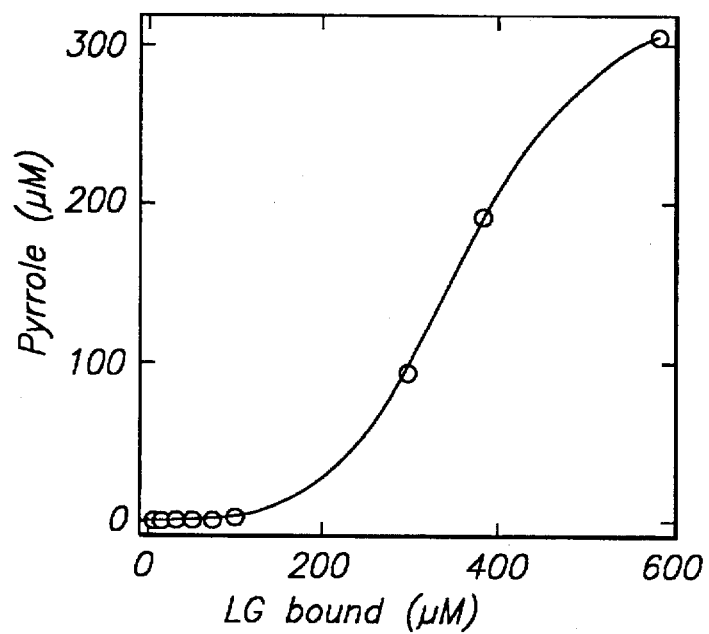
FIG. 16 graphically depicts immunoreactivity generated by the binding of various amounts of LG with HSA (3 mg/mL).
Figure 15B:
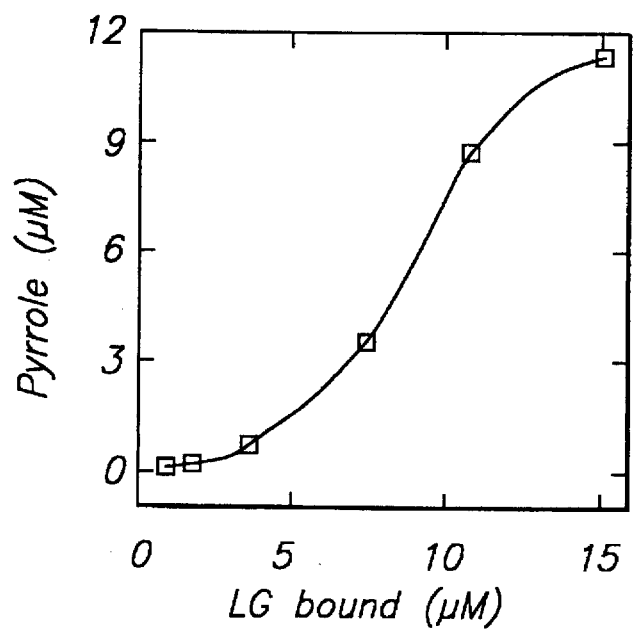
FIG. 15B graphically depicts immunoreactivity generated by the binding of various amounts of LG with LDL (0.5 mg/mL).

The relationship between immunoreactivity produced and the amount of LGE$_2$ bound to LDL is apparently not linear (See FIG. 15B, which graphically depicts immunoreactivity generated by the binding of various amounts of LG with LDL (0.5 mg/mL). Rather the relationship may be sigmoidal, since at low LG to protein ratios, lower levels of immunoreactivity are generated than expected for a linear dependence. (FIG. 15B). The observed nonlinearity could be a characteristic of LDL particles (e.g., a consequence of their micellar structure) or it could be a characteristic of the LG-protein adduction reaction. Similar experiments performed with HSA established that the relationship between immunoreactivity produced and LGE$_2$ bound to HSA is definitely not linear (FIG. 16).

Because they are more sensitive and selective than previous antibodies raised against a pyrazole isostere, the antibodies raised against LG-KLH are well suited to the detection of the low concentrations of LG-protein adducts that may be generated in vivo. However, the partitioning of a reactive electrophilic intermediate into an immunoreactive pyrrole (structure 4; see Table 1) and non-immunoreactive ternary adducts (e.g., crosslinks) complicates quantitative analysis of LG-protein adduction using the immunoassay. This is because the yield of immunoreactive pyrrole is expected to vary with the level of adduction. Thus, at low levels of adduction, pyrrole yields will be suppressed because a relatively high concentration of free lysyl residues will favor interception of the electrophilic initial adduct to produce crosslinks. On the other hand, high levels of adduction result in relatively low concentrations of free lysyl residues, and favor the dehydration reaction to produce pyrrole structure 4.

Figure 17A:
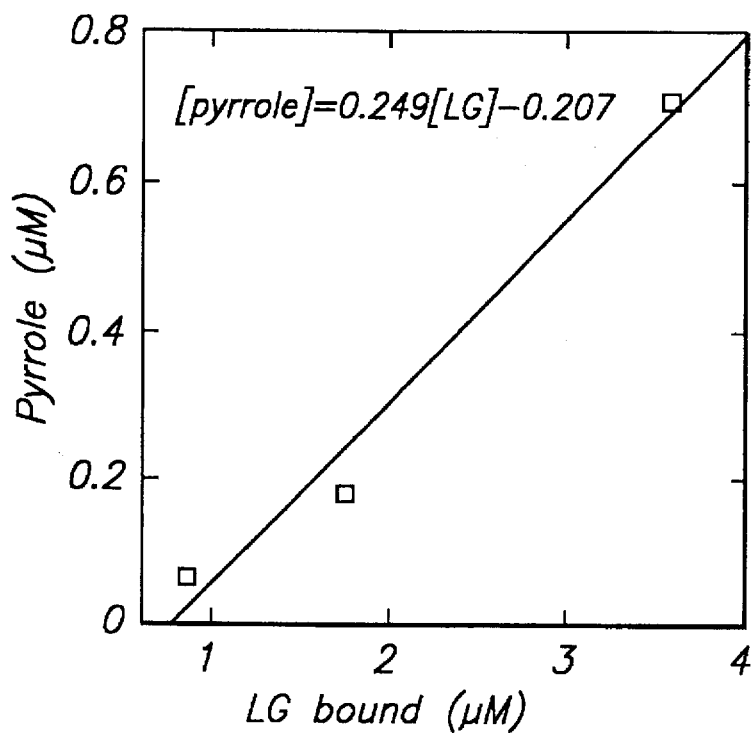
FIG. 17A graphically depicts the correlation of total LG bound to LDL (0.5 mg/mL) and pyrrole immunoreactivity detected.
Figure 17B:
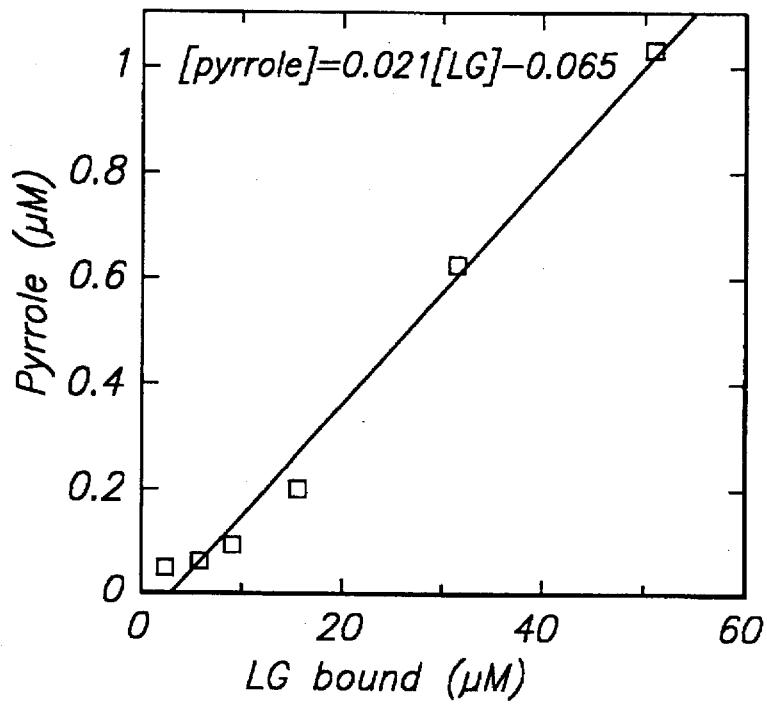
FIG. 17B graphically depicts the correlation of total LG bound to HSA (3 mg/mL) and pyrrole immunoreactivity detected.

As expected, calibration curves for the mount of LG-adduction that corresponds to the various levels of immunoreactive pyrrole detected in LG-LDL and LG-HSA (FIGS. 15A/B and FIG. 16, respectively) are nonlinear. At low levels of adduction, yields of immunoreactive pyrrole correspond to only a few percent of total adduct. However, about half of the initial adduct converts to pyrrole at higher levels of adduction. For the low levels of adduction that might be found in vivo, there is a roughly linear correlation between the total amount of LG bound and the level of immunoreactivity detected (FIGS. 17A and 17B). FIG. 17A graphically depicts the correlation of total LG bound to LDL (0.5 mg/mL) and pyrrole immunoreactivity detected, while FIG. 17B graphically depicts the correlation of total LG bound to HSA (3 mg/mL) and pyrrole immunoreactivity detected. However, interpretation of the levels of immunoreactivity detected in oxLDL is further complicated by the likelihood that major amounts of non-immunoreactive isomeric protein adducts will be co-produced with levuglandins during the free-radical oxidation of lipids.

Example 7

LG-Protein Adduct Immunoreactivity

Figure 4:
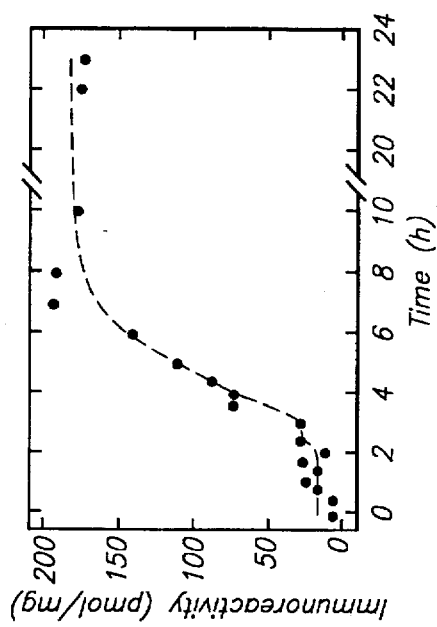
FIG. 4 graphically depicts the generation of LGE$_2$-protein adduct immunoreactive products by oxidation of LDL with Cu$^{+2}$.

As noted above, oxidative modification of LDLs involves generation of reactive products by oxidation of phospholipids, and the formation of adducts between those products and the protein, apo B. [D. Steinberg et al., N. Eng. J. Med. 320: 915–24 (1989)]. Native LDL showed no immunoreactivity with LGF$_2$-KLH antibodies. In contrast, LDL that was modified by an in vitro model [S. Parthasarathy et al., Annu. Rev. Med. 43: 219–25 (1992)] using Cu$^{+2}$ inhibited antibody binding. As expected, if the primary epitope being detected is LG-pyrrole, the slope of the inhibition curve is the same as that for LGE$_2$-HSA (FIG. 12). As depicted in FIG. 4, studies revealed a time-dependent increase of immunoreactivity over several hours; the level of immunoreactivity reached a maximum within 3–6 h, and showed no decrease over 23 h.

Figure 18:
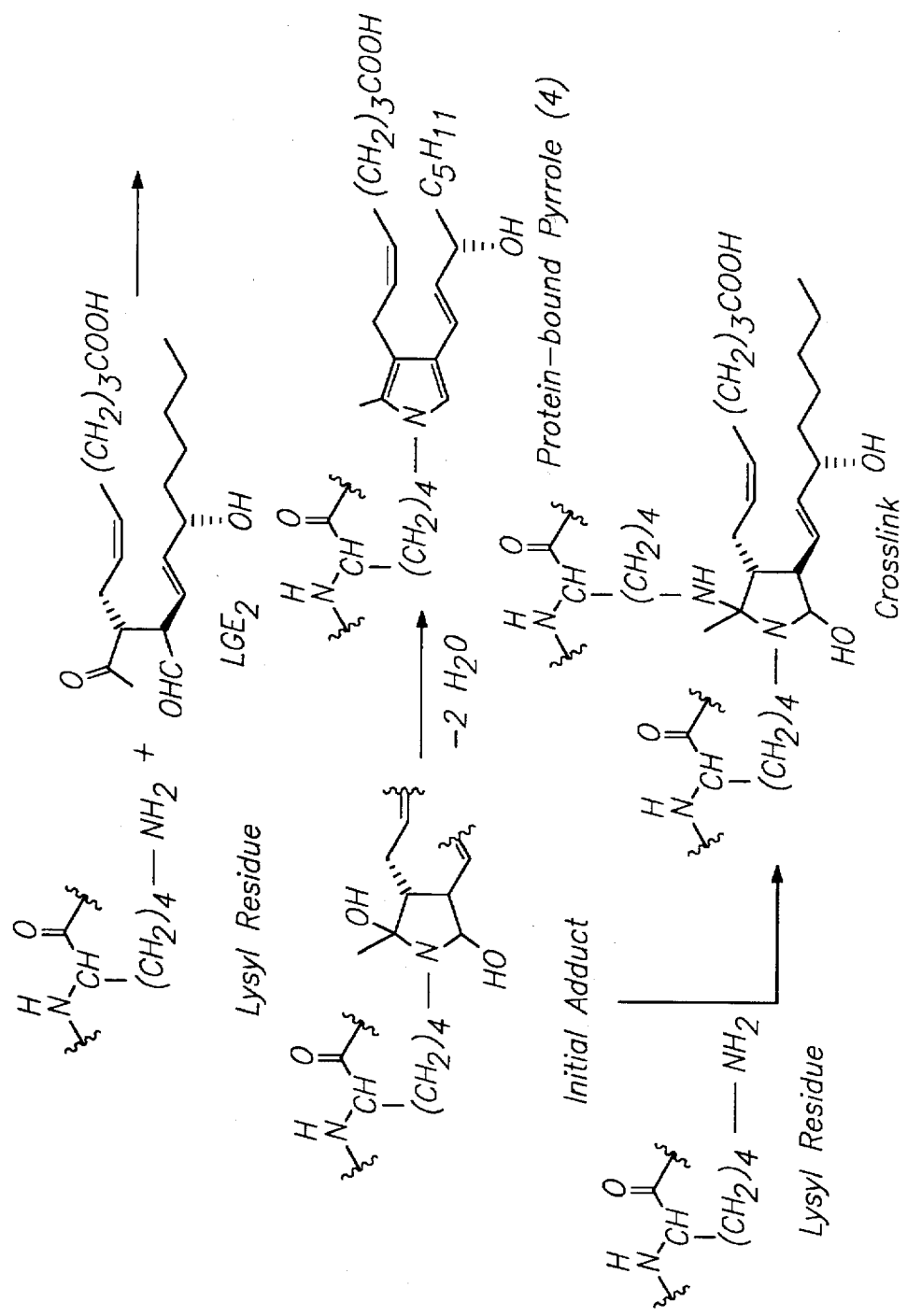
FIG. 18 is a schematic illustrating that the reaction of proteins with $LGE_2$ generates a reactive electrophilic intermediate LG-protein adduct that undergoes competing dehydration and nucleophilic capture reactions. The number in parenthesis refers to structure number.

FIG. 18 is a schematic illustrating that the reaction of proteins with LGE$_2$ generates a reactive electrophilic intermediate LG-protein adduct that undergoes competing dehydration and nucleophilic capture reactions. Dehydration generates protein-bound pyrrole (structure 4), while nucleophilic capture can produce, among other things, protein oligomerization or DNA-protein crosslinks.

As previously noted, the reaction of relatively high concentrations of LGE$_2$ with a protein using antibodies raised against a pyrazole isostere to detect protein-bound LG-derived pyrrole has been performed. Although covalent adduction of 1.2 mM LGE$_2$ with KLH (1.3 mg/mL) is nearly complete within 1.5 h in PBS (pH 7.4), very little immunoreactivity is generated. [E. DiFranco et al., Chem. Res. Toxicol. 8: 61–67 (1995)]. Transformation of the initial adduct into the immunoreactive pyrrole (structure 4) required several hours for completion. In the present in vitro study of LDL oxidation, the delayed appearance of immunoreactivity (See FIG. 4) may reflect the slow dehydration of an initial LG-protein adduct that has little or no immunoreactivity. However, oxidation of LDL often exhibits an induction period during which endogenous antioxidants must be consumed before oxidative modification of phospholipids occurs. [S. M. Lynch et al., J. Clin. Invest. 93: 998–1004 (1994)]. Thus, the requirement for antioxidant depletion may contribute to the delayed appearance of immunoreactivity evident in FIG. 4.

Example 8

Noninterference of PGs or 8-epi-PGs

Elevated levels of PGs and 8-epi-PGs are associated with oxidative injury, and these lipid oxidation products cross-react, albeit weakly, with $LGE_2$-KLH antibodies. A control experiment was performed to rule out a significant contribution by these natural products to the immunoreactivity detected in oxLDL. In the experiment, 8-epi-$PGF_{2\alpha}$ was added to native LDL, and the cross-reactivity of 8-epi-$PGF_{2\alpha}$ was detected by an ELISA with the $LGE_2$-KLH antibodies. Subsequent dialysis of the mixture resulted in complete removal of the PG and its immunoreactivity from the LDL sample. However, extensive dialysis of oxLDL failed to remove the immunoreactivity detected by ELISA. Therefore, the non-dialyzable immunoreactive oxidation products detected are presumably protein-bound.

In summary, the oxidation product detected in oxLDL with ELISA is not a PG nor either of the two protein-bound lipid oxidation products, HNE-LDL or MDA-LDL. Rather, the oxidation product is a previously unidentified product, presumably an LG-derived protein-bound pyrrole that is generated by the reaction of 8-epi-$LGE_2$-PC (structure 2) or free 8-epi-$LGE_2$ (produced by enzymatic hydrolysis of structure 2; see Table 1) with a protein such as apo B.

From the above, it should be evident that the present invention provides for the production of antibodies to $LGE_2$-protein antigens. The antibodies can be used to detect adducts of $LGE_2$ with human low density lipoprotein (LDL), specifically oxidized LDL. Detection of these adducts may be useful in the diagnosis of disease states such as atherosclerosis.

I claim:

1. A method of producing antibodies specific to levuglandin-carrier protein-bound pyrrole adducts comprising:
   a) reacting a levuglandin with a carrier protein to form a levuglandin-carrier protein-bound pyrrole adduct;
   b) injecting said levuglandin-carrier protein-bound pyrrole adduct into an animal under conditions such that antibodies specific to levuglandin-carrier protein-bound pyrrole adducts are produced; and
   c) collecting said antibodies from said animal.

2. The method of claim 1, wherein said levuglandin is levuglandin $E_2$.

3. The method of claim 2, wherein said levuglandin-carrier protein-bound pyrrole adduct is levuglandin $E_2$-human serum albumin.

4. The method of claim 2, wherein said levuglandin-carrier protein-bound pyrrole adduct is levuglandin $E_2$-bovine serum albumin.

5. The method of claim 2, wherein said levuglandin-carrier protein-bound pyrrole adduct is levuglandin $E_2$-keyhole limpet hemocyanin.

6. The method of claim 1, wherein said antibodies are capable of detecting a levuglandin-specific protein adduct.

7. The method of claim 6, wherein said levuglandin-specific protein adduct is levuglandin $E_2$-apolipoprotein B.

8. The method of claim 1, wherein said animal is a rabbit.

9. The method of claim 1, further comprising the step, after step c), of purifying said antibodies.

10. The method of claim 9, wherein said purifying step comprises contacting said antibodies with Protein A.

11. A method of detecting levuglandin-carrier protein-bound pyrrole adducts in a patient having a disease associated with oxidative injury, comprising:
   a) providing:
      (i) antibodies to a levuglandin-carrier protein-bound pyrrole adduct, said adduct containing a levuglandin component and a protein component,
      (ii) a patient sample to be tested for the presence of antigens reactive with said antibodies;
   b) combining said sample and said antibodies to from a reaction solution; and
   c) screening said reaction solution for the presence of a reaction between said antigens and said antibodies.

12. The method of claim 11, wherein said antibodies are capable of detecting a levuglandin-specific protein adduct.

13. The method of claim 12, wherein said levuglandin-specific protein adduct is levuglandin $E_2$-low-density lipoprotein.

14. The method of claim 12, wherein said levuglandin-specific protein adduct is levuglandin $E_2$-lipoprotein (a).

15. The method of claim 11, wherein said sample is human plasma.

16. The method of claim 15, wherein said plasma is dialyzed plasma.

17. The method of claim 11, wherein said sample is cerebrospinal fluid.

18. The method of claim 11, wherein said sample is synovial fluid.

19. The method of claim 11, wherein said sample is the fluid resulting from peritoneal dialysis.

20. The method of claim 11, wherein said antibodies are polyclonal.

* * * * *

UNITED STATES PATENT AND TRADEMARK OFFICE
CERTIFICATE OF CORRECTION

PATENT NO. : 5,686,250
DATED : 11/11/97
INVENTOR(S) : Robert G. Salomon

It is certified that error appears in the above-indentified patent and that said Letters Patent is hereby corrected as shown below:

Column 1, line 5, please insert --This invention has been made with government support under Grant No. NIH-GM21249 from the National Institutes of Health. The government has certain rights in the invention.--

Signed and Sealed this

Twenty-seventh Day of April, 1999

Attest:

Q. TODD DICKINSON

Attesting Officer

Acting Commissioner of Patents and Trademarks